US010492660B2

(12) United States Patent
Kanamori et al.

(10) Patent No.: US 10,492,660 B2
(45) Date of Patent: Dec. 3, 2019

(54) IMAGE PROCESSING APPARATUS AND ENDOSCOPE

(71) Applicant: Panasonic Intellectual Property Management Co., Ltd., Osaka (JP)

(72) Inventors: Katsuhiro Kanamori, Osaka (JP); Norihiro Imamura, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 45 days.

(21) Appl. No.: 15/960,438

(22) Filed: Apr. 23, 2018

(65) Prior Publication Data

US 2018/0235438 A1 Aug. 23, 2018

Related U.S. Application Data

(63) Continuation of application No. 14/467,316, filed on Aug. 25, 2014, now abandoned, which is a (Continued)

(30) Foreign Application Priority Data

Nov. 9, 2012 (JP) .................................. 2012-247178

(51) Int. Cl.
*A61B 1/00* (2006.01)
*A61B 1/06* (2006.01)
(Continued)

(52) U.S. Cl.
CPC ...... *A61B 1/00009* (2013.01); *A61B 1/00186* (2013.01); *A61B 1/05* (2013.01); (Continued)

(58) Field of Classification Search
None
See application file for complete search history.

(56) References Cited

U.S. PATENT DOCUMENTS 6,122,103 A * 9/2000 Perkins ................ G02B 5/3058
359/485.03
2002/0154215 A1* 10/2002 Schechterman ... A61B 1/00193
348/51
(Continued)

FOREIGN PATENT DOCUMENTS

JP 2002-095635 4/2002
JP 2002095635 A * 4/2002 ............. A61B 1/043
(Continued)

OTHER PUBLICATIONS

Viktor Gruev et al., "CCD polarization imaging sensor with aluminum nanowire optical filters", Aug. 30, 2010/vol. 18, No. 18/ Optics Express pp. 19087-19094.
(Continued)

*Primary Examiner* — Mohammed S Rahaman
(74) *Attorney, Agent, or Firm* — Renner, Otto, Boisselle & Sklar, LLP

(57) ABSTRACT

An embodiment of an image processing apparatus includes: an illuminating section which sequentially irradiates an object with a first and second illuminating light beams polarized in different directions. The section emits the polarized light beams sequentially so that the wavelength ranges of the light beams do not overlap with each other. The apparatus further includes: a polarization image sensor; a polarization mosaic processing section which obtains a first polarization image while the object is being irradiated with the first illuminating light beam and a second polarization image while the object is being irradiated with the second illuminating light beam; a depressed area detecting section which detects a depressed area on the surface of the object based on the polarization images; and an image forming section which forms an image representing the depressed area in an enhanced form.

17 Claims, 46 Drawing Sheets

Related U.S. Application Data continuation of application No. PCT/JP2013/005385, filed on Sep. 11, 2013.

(51) Int. Cl.
    *A61B 1/05*     (2006.01)
    *G02B 3/00*     (2006.01)
    *G02B 5/20*     (2006.01)
    *G02B 5/30*     (2006.01)

(52) U.S. Cl.
    CPC .......... *A61B 1/0638* (2013.01); *A61B 1/0646* (2013.01); *G02B 3/0037* (2013.01); *G02B 5/201* (2013.01); *G02B 5/3025* (2013.01)

(56) References Cited

U.S. PATENT DOCUMENTS

| | | |
|---|---|---|
| 2003/0040668 A1 | 2/2003 | Kaneko et al. |
| 2008/0063998 A1* | 3/2008 | Liang .................. A61B 1/0638 433/29 |
| 2009/0225156 A1 | 9/2009 | Akiyama et al. |
| 2010/0026785 A1 | 2/2010 | Soto-Thompson |
| 2010/0079757 A1 | 4/2010 | Murooka et al. |
| 2010/0092055 A1* | 4/2010 | Matsuda ............ A61B 1/00009 382/128 |
| 2010/0102211 A1 | 4/2010 | Murooka et al. |
| 2010/0183200 A1* | 7/2010 | Wu .................. G06K 9/00046 382/127 |
| 2013/0135453 A1 | 5/2013 | Kanamori |

FOREIGN PATENT DOCUMENTS

| | | | |
|---|---|---|---|
| JP | 2003-47588 | 3/2003 | |
| JP | 2009-210780 | 9/2009 | |
| JP | 2009-246770 | 10/2009 | |
| JP | 2010-104421 | 5/2010 | |
| JP | 2010-130655 | 6/2010 | |
| JP | 2012-024283 | 2/2012 | |
| JP | 2012-045029 | 3/2012 | |
| WO | 2012/039086 | 3/2012 | |
| WO | WO2012039086 A1 * | 3/2012 | ......... A61B 1/00009 |

OTHER PUBLICATIONS

International Search Report for corresponding International Application No. PCT/JP2013/005385, dated Nov. 25, 2013.

Extended European Search Report for corresponding European Application No. 13853498.7 dated Jan. 21, 2016.

Office Action dated Jun. 23, 2016 for parent U.S. Appl. No. 14/467,316, filed Aug. 25, 2014.

Final Office Action dated Nov. 21, 2016 for parent U.S. Appl. No. 14/467,316, filed Aug. 25, 2014.

Office Action dated Jul. 12, 2017 for parent U.S. Appl. No. 14/467,316, filed Aug. 25, 2014.

Final Office Action dated Nov. 28, 2017 for parent U.S. Appl. No. 14/467,316, filed Aug. 25, 2014.

Advisory Action dated Mar. 9, 2018 for parent U.S. Appl. No. 14/467,316, filed Aug. 25, 2014.

\* cited by examiner (a)         (b)

【SPECULAR REFLECTION】

(a)

【INTERNAL DIFFUSE REFLECTION】

(b)

DIRECTION IN WHICH GROOVES RUN
ON LENTICULAR PLATE (a)             (b)

| (A) PARALLEL NICOLS IMAGE (P∥) | |
|---|---|
| (B) CROSSED NICOLS IMAGE (P⊥) | (C) MICRO-GEOMETRIC SURFACE TEXTURE IMAGE |

(A)

(B)

(A)

(B)     (C)

IMAGE PROCESSING APPARATUS AND ENDOSCOPE

This is a continuation of U.S. application Ser. No. 14/467,316, filed on Aug. 24, 2014, which is a continuation of International Application No. PCT/JP2013/005385, with an international filing date of Sep. 11, 2013, which claims priority of Japanese Patent Application No. 2012-247178, filed on Nov. 9, 2012, the contents of which are hereby incorporated by reference.

BACKGROUND

1. Technical Field

The present disclosure relates to an image processing apparatus and an endoscope for use in the image processing apparatus.

2. Description of the Related Art

In the field of an endoscope which captures an image by illuminating the wall surface of an organism's organ which is covered with a mucosa with light, not only a variation in the surface color of the object but also its micro-geometric surface texture need to be inspected. Such a surface texture is a translucent micro-geometry with an average size of approximately 0.5 to 1.0 mm and a depth of approximately 0.1 to 0.2 mm as in a gastric area in a stomach, for example. It is very difficult to capture such a micro-geometric surface texture of the object based on the shades of the light intensity when the object is observed through an endoscope. For that reason, currently, some blue pigment liquid such as an indigo carmine solution is sprinkled onto a mucosa and the surface of the mucosa, of which the grooves are filled with such a liquid, is observed based on its light intensities.

According to such an observation method, however, some liquid needs to be sprinkled onto the mucosa, and therefore, the object may bleed, the mucosa may change its color, and many other problems will arise. Thus, to observe such a micro-geometric surface as closely as possible, some people have proposed a polarization endoscope which uses a polarized light source and a polarization image sensor (see Japanese Laid-Open Patent Publication No. 2009-246770, for example).

SUMMARY

According to the conventional technique that uses polarized light as disclosed in Japanese Laid-Open Patent Publication No. 2009-246770, an object is irradiated with illuminating light having a particular polarization component, two images are captured based on polarization components of the light returning from the object, which are respectively parallel and perpendicular to the illuminating light, and a variation in surface shape is calculated using those images captured.

An embodiment of an image processing apparatus according to the present disclosure detects a depressed area on the surface of the object in a polarization image capturing mode and captures a non-polarization image in a non-polarization image capturing mode, thereby obtaining both an image which represents the depressed area on the object's surface in an enhanced form and a non-polarization image.

In one general aspect, an embodiment of an image processing apparatus disclosed herein includes: an illuminating section which sequentially irradiates an object with a first illuminating light beam that is polarized in a first direction and with a second illuminating light beam that is polarized in a second direction that intersects with the first direction in a polarization image capturing mode and which irradiates the object with a non-polarized illuminating light beam in a non-polarization image capturing mode, the illuminating section emitting the first and second illuminating light beams sequentially so that the wavelength range of the first illuminating light beam does not overlap with the wavelength range of the second illuminating light beam somewhere; an image sensor including a polarization mosaic array in which a plurality of polarizers with mutually different polarization transmission axis directions are arranged and a photosensing element array which receives light that has been transmitted through each polarizer and which outputs a signal; a polarization mosaic processing section which obtains, in the polarization image capturing mode, a first polarization image to be generated based on a signal representing light that has been transmitted through a polarizer that has the polarization transmission axis in a direction intersecting with the first direction while the object is being irradiated with the first illuminating light beam and a second polarization image to be generated based on a signal representing light that has been transmitted through a polarizer that has the polarization transmission axis in a direction intersecting with the second direction while the object is being irradiated with the second illuminating light beam, and which obtains, in the non-polarization image capturing mode, a non-polarization image to be generated based on a signal representing light that has been transmitted through each polarizer while the object is being irradiated with the non-polarized illuminating light beam; a depressed area detecting section which detects a depressed area on the surface of the object based on at least one of the first and second polarization images; and an image forming section which forms an image that represents the depressed area on the object's surface in an enhanced form.

In another aspect, an image processing apparatus disclosed herein includes: an illuminating section which sequentially irradiates an object with a first white illuminating light beam that is polarized in a first direction and with a second white illuminating light beam that is polarized in a second direction that intersects with the first direction in a polarization image capturing mode and which irradiates the object with a non-polarized white illuminating light beam in a non-polarization image capturing mode; an image sensor including a polarization mosaic array in which a plurality of polarizers with mutually different polarization transmission axis directions are arranged, a color mosaic filter in which color filters with mutually different light transmission properties are arranged, and a photosensing element array which receives light that has been transmitted through each polarizer and each color filter and which outputs a signal; a polarization mosaic processing section which obtains, in the polarization image capturing mode, a first polarization image to be generated based on a signal representing light that has been transmitted through a polarizer that has the polarization transmission axis in a direction intersecting with the first direction while the object is being irradiated with the first white illuminating light beam and a second polarization image to be generated based on a signal representing light that has been transmitted through a polarizer that has the polarization transmission axis in a direction intersecting with the second direction while the object is being irradiated with the second white illuminating light beam, and which obtains, in the non-polarization image capturing mode, a non-polarization image to be generated based on a signal representing light that has been transmitted through each polarizer while the object is being irradiated with the non-polarized white illuminating light beam; a depressed area detecting section which detects a depressed area on the surface of the object based on at least one of the first and second polarization images; and an image forming section which forms an image that represents the depressed area on the object's surface in an enhanced form.

In another aspect, an image processing apparatus disclosed herein includes: an illuminating section which sequentially irradiates an object with a first white illuminating light beam that is polarized in a first direction and with a second white illuminating light beam that is polarized in a second direction that intersects with the first direction in a polarization image capturing mode and which irradiates the object with a non-polarized white illuminating light beam in a non-polarization image capturing mode; an image sensor including a plurality of polarizers with mutually different polarization transmission axis directions, an aperture area in which color filters with mutually different light transmission properties are arranged, a photosensing element array which receives light that has been transmitted through the aperture area and which outputs a signal, and a micro lens array which covers a plurality of photosensing elements; an image separating section which obtains, in the polarization image capturing mode, first and second polarization images based on signals supplied from selected ones of the plurality of photosensing elements that are covered with the micro lens array, the first polarization image being generated based on a signal representing light that has been transmitted through a polarizer that has the polarization transmission axis in a direction intersecting with the first direction while the object is being irradiated with the first white illuminating light beam, the second polarization image being generated based on a signal representing light that has been transmitted through a polarizer that has the polarization transmission axis in a direction intersecting with the second direction while the object is being irradiated with the second white illuminating light beam, the image separating section obtaining, in the non-polarization image capturing mode, a non-polarization image to be generated based on a signal representing light that has been transmitted through each polarizer while the object is being irradiated with the non-polarized white illuminating light beam; a depressed area detecting section which detects a depressed area on the surface of the object based on at least one of the first and second polarization images; and an image forming section which forms an image that represents the depressed area on the object's surface in an enhanced form.

In another aspect, an image processing apparatus disclosed herein includes: an illuminating section which sequentially irradiates an object with a first white illuminating light beam that is polarized in a first direction and with a second white illuminating light beam that is polarized in a second direction that intersects with the first direction in a polarization image capturing mode and which irradiates the object with a non-polarized white illuminating light beam in a non-polarization image capturing mode; an aperture area in which a plurality of polarizers with mutually different polarization transmission axis directions are arranged; an image sensor including a color mosaic filter in which color filters with mutually different light transmission properties are arranged, a photosensing element array which receives light that has been transmitted through each polarizer in the aperture area and then each color filter and which outputs a signal, and a micro lens array which covers a plurality of photosensing elements; an image separating section which obtains, in the polarization image capturing mode, first and second polarization images based on signals supplied from selected ones of the plurality of photosensing elements that are covered with the micro lens array, the first polarization image being generated based on a signal representing light that has been transmitted through a polarizer that has the polarization transmission axis in a direction intersecting with the first direction while the object is being irradiated with the first white illuminating light beam, the second polarization image being generated based on a signal representing light that has been transmitted through a polarizer that has the polarization transmission axis in a direction intersecting with the second direction while the object is being irradiated with the second white illuminating light beam, the image separating section obtaining, in the non-polarization image capturing mode, a non-polarization image to be generated based on a signal representing light that has been transmitted through each polarizer while the object is being irradiated with the non-polarized white illuminating light beam; a depressed area detecting section which detects a depressed area on the surface of the object based on at least one of the first and second polarization images; and an image forming section which forms an image that represents the depressed area on the object's surface in an enhanced form.

In one general aspect, an endoscope disclosed herein is designed to be used in an image processing apparatus according to any of the embodiments described above, and includes: an illuminating section which sequentially irradiates an object with a first illuminating light beam that is polarized in a first direction and with a second illuminating light beam that is polarized in a second direction that intersects with the first direction in a polarization image capturing mode and which irradiates the object with a non-polarized illuminating light beam in a non-polarization image capturing mode, the illuminating section emitting the first and second illuminating light beams sequentially so that the wavelength range of the first illuminating light beam does not overlap with the wavelength range of the second illuminating light beam somewhere; and an image sensor including a polarization mosaic array in which a plurality of polarizers with mutually different polarization transmission axis directions are arranged and a photosensing element array which receives light that has been transmitted through each polarizer and which outputs a signal.

In another aspect, an endoscope disclosed herein is designed to be used in an image processing apparatus according to any of the embodiments described above, and includes: an illuminating section which sequentially irradiates an object with a first white illuminating light beam that is polarized in a first direction and with a second white illuminating light beam that is polarized in a second direction that intersects with the first direction in a polarization image capturing mode and which irradiates the object with a non-polarized white illuminating light beam in a non-polarization image capturing mode; and an image sensor including a polarization mosaic array in which a plurality of polarizers with mutually different polarization transmission axis directions are arranged, a color mosaic filter in which color filters with mutually different light transmission properties are arranged, and a photosensing element array which receives light that has been transmitted through each polarizer and each color filter and which outputs a signal.

In another aspect, an endoscope disclosed herein is designed to be used in an image processing apparatus according to any of the embodiments described above, and includes: an illuminating section which sequentially irradiates an object with a first white illuminating light beam that is polarized in a first direction and with a second white illuminating light beam that is polarized in a second direction that intersects with the first direction in a polarization image capturing mode and which irradiates the object with a non-polarized white illuminating light beam in a non-polarization image capturing mode; and an image sensor including a plurality of polarizers with mutually different polarization transmission axis directions, an aperture area in which color filters with mutually different light transmission properties are arranged, a photosensing element array which receives light that has been transmitted through the aperture area and which outputs a signal, and a micro lens array which covers a plurality of photosensing elements;

In another aspect, an endoscope disclosed herein is designed to be used in an image processing apparatus according to any of the embodiments described above, and includes: an illuminating section which sequentially irradiates an object with a first white illuminating light beam that is polarized in a first direction and with a second white illuminating light beam that is polarized in a second direction that intersects with the first direction in a polarization image capturing mode and which irradiates the object with a non-polarized white illuminating light beam in a non-polarization image capturing mode; an aperture area in which a plurality of polarizers with mutually different polarization transmission axis directions are arranged; and an image sensor including a color mosaic filter in which color filters with mutually different light transmission properties are arranged, a photosensing element array which receives light that has been transmitted through each polarizer in the aperture area and then each color filter and which outputs a signal, and a micro lens array which covers a plurality of photosensing elements.

According to an embodiment of the present disclosure, the object is sequentially irradiated with a first illuminating light beam that is polarized in a first direction and with a second illuminating light beam that is polarized in a second direction that intersects with the first direction in a polarization image capturing mode, and irradiated with a non-polarized illuminating light beam in a non-polarization image capturing mode. Thus, information about the microgeometry and tilt of the object's surface can be obtained separately from an ordinary object image. As a result, an image similar to the one in which some blue pigment liquid such as an indigo carmine solution is sprinkled onto a mucosa (i.e., an image in which the depressed area is represented in an enhanced form) can be synthesized.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

BRIEF DESCRIPTION OF THE DRAWINGS

FIG. 17 shows exemplary differentiation processing masks to be used by the depressed area detecting section 204.

DETAILED DESCRIPTION

Figure 1:
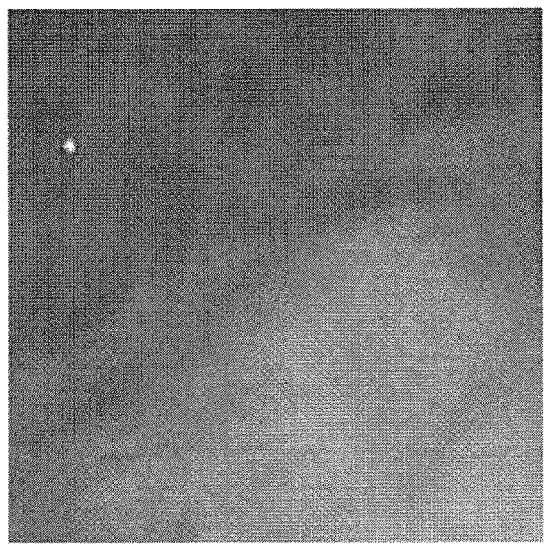
FIG. 1 shows images representing the mucosa of a stomach as observed through an endoscope.
Figure 1:
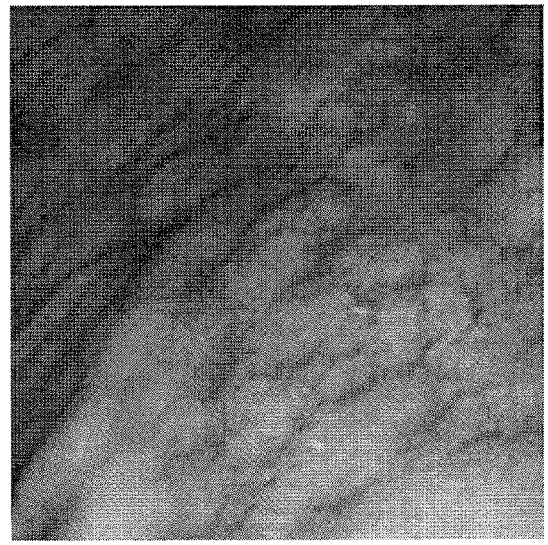

FIG. 1 is an image representing the surface mucosa of a human stomach as observed through an endoscope. Specifically, portion (a) of FIG. 1 shows a normal color image, in which the surface appears to have only gentle ups and downs. That is to say, according to ordinary color image processing, it is difficult to sense transparent or translucent micro-geometry on the surface of an organ through an endoscope which is designed to inspect digestive organs, for example. In this description, the "ordinary color image processing" refers herein to processing for obtaining a color light intensity image by irradiating the object with non-polarized white light. A color image thus obtained will be referred to herein as a "color light intensity image" and a shooting session for obtaining such a color light intensity image will be sometimes referred to herein as a "color light intensity shooting session".

On the other hand, FIG. 1(b) shows a color image that was obtained after an indigo carmine solution had been sprinkled. In this image, the micro-geometric surface texture (with a size of about 0.5 to 1.0 mm and a depth of about 0.1 to 0.2 mm) is sensible clearly.

Figure 2:
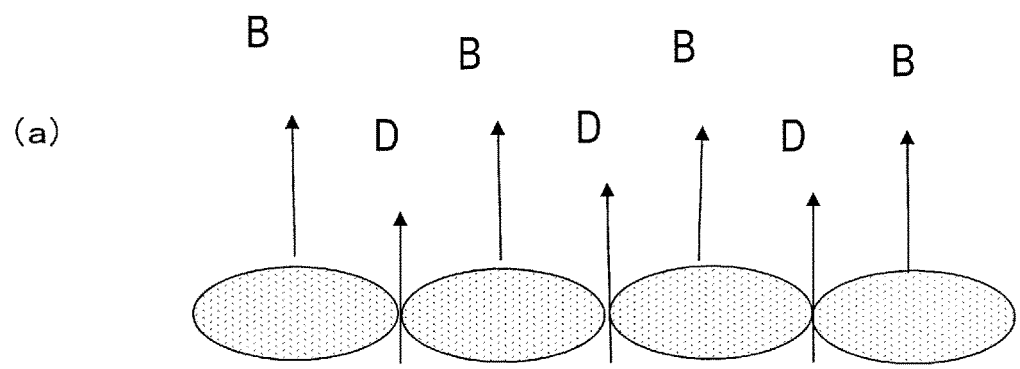
FIG. 2 illustrates how translucent depressions and projections are observed based on their light intensities.
Figure 2:
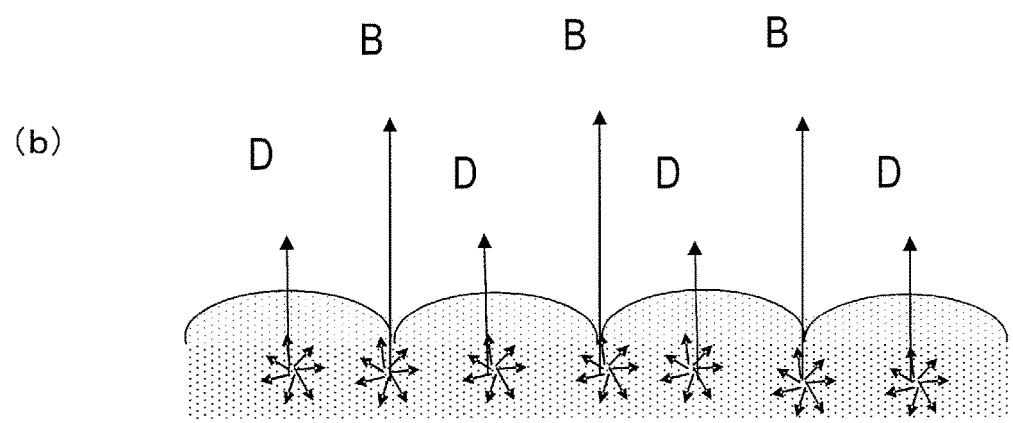

FIG. 2 schematically illustrates a cross section of a micro-geometric structure on the surface of an organ such as a stomach or bowels. In general, the micro-geometry on the surface of a stomach or bowels would be an iterative arrangement of semi-cylindrical upwardly projecting portions. A depressed area located between two adjacent projections is typically a tiny "groove" running in a certain direction. A number of such grooves may run in substantially the same direction locally but may form a complex curved pattern or any other pattern globally. The micro-geometry on the surface of an object may actually include dotted depressions or projections. In this description, those depressions of such a micro-geometry will be simply referred to herein as "grooves" or "groove areas". FIG. 2 schematically illustrates a cross section which crosses several grooves that are present within a narrow area on the surface of the object. In the following description, the depressions and projections shown in FIG. 2 may be supposed to run in the direction coming out of the paper for the sake of simplicity.

When observed through an endoscope, the object is illuminated with coaxial illumination (i.e., the light source is arranged in the vicinity of the shooting optical axis). That is to say, the object shown in FIG. 2 is irradiated with an illuminating light beam, and is shot, from substantially right over the object. There are roughly two types of reflected light beams to be observed by normal color light intensity shooting using such coaxial illumination. One of the two types is specular reflected light which is reflected from the surface as shown in portion (a) of FIG. 2. The other type is internally diffused light which penetrates through the medium, gets reflected from a deeper layer, and then returns toward the source through the surface as shown in (b) portion of FIG. 2. The specular reflected light is produced only when the direction of the irradiating light and the image capturing optical axis almost satisfy the condition of regular reflection, and therefore, is produced only locally when a scene is shot through an endoscope. The color of the specular reflected light is the color of the illumination, i.e., the color white, and has very high intensity. According to the regular reflection condition described above, the object image under the specular reflected light is generally intense and bright at projections of the object's micro-geometric surface but is weak and dark at its depressions. On the other hand, the internally diffused light is observed all over the scene shot. The color of the internally diffused light is the color of the medium itself, and its intensity is not so high. When irradiated with the internally diffused light, the entire medium tends to shine. In an object image produced by the internally diffused light, projections that are thick portions of the medium tend to look dark, and depressions that are thin portions of the medium tend to look bright. That is to say, the specular reflected light and the internally diffused light will behave in mutually opposite ways in terms of the light intensity level and the micro-geometric pattern on the object's surface.

In a normal shooting session, those two types of reflected light beams are superposed one upon the other to form a single light intensity image (i.e., a scene shot). That is why in a region of the scene shot where the difference in light intensity between those two types of light beams reflected from depressions is almost equal to the difference in light intensity between those two types of light beams reflected from projections, there is substantially no difference in light intensity level between the depressions and projections. As a result, in a normal light intensity image, there is almost no difference in light intensity on the object's micro-geometric surface. Or even if there is some difference in light intensity level between the depressions and projections but if processing was carried out by reference to that information so that a pixel with a lower light intensity than surrounding pixels is detected as a depression, then the relative positions of those regions with relatively intense specular reflected light and those regions with relatively intense internally diffused and reflected light would be different from the relative positions of the depressions and projections, which is a serious problem that makes it very difficult to get the light intensity image processing done as intended.

Figure 3:
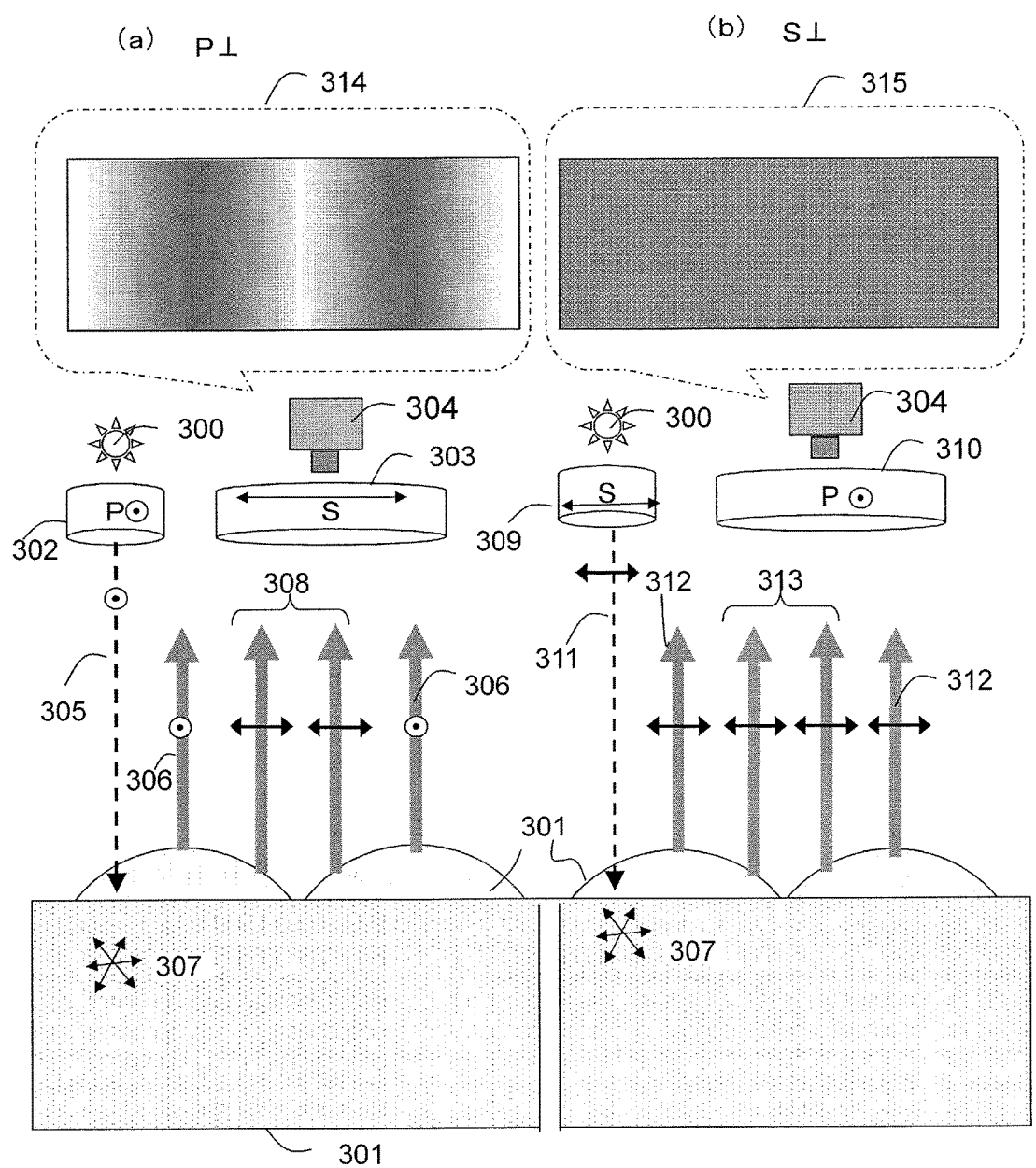
FIG. 3 illustrates how to observe an object using a polarized light beam.

Portions (a) and (b) of FIG. 3 illustrate how to observe an object using a polarized light beam. Specifically, in the example illustrated in portion (a) of FIG. 3, a polarization image in a crossed Nicols state is obtained by irradiating the object with a polarized illuminating light beam, of which the polarization direction is parallel to the depressions and projections of the object's surface. On the other hand, in the example illustrated in portion (b) of FIG. 3, a polarization image in a crossed Nicols state is obtained by irradiating the object with a polarized illuminating light beam, of which the polarization direction is perpendicular to the depressions and projections of the object's surface.

According to the setting shown in portion (a) of FIG. 3, an illuminating light source 300 and a P polarization filter 302 are arranged with respect to a schematic model 301 representing a micro-geometric cross section of the surface of an organ. Thus, the model 301 is irradiated with light (which is either P-polarized light or a P wave and) which is polarized parallel to the direction in which the depressions and projections run in the model 301 (i.e., the direction coming out of the paper on which FIG. 3 is drawn). Meanwhile, an observer side polarization filter 303(S) is arranged so as to define the crossed Nicols state, and an image capture device 304 captures an image.

On the other hand, according to the setting shown in portion (b) of FIG. 3, a polarization filter 309(S) is arranged for an S polarized illuminating light source, and an observer side polarization filter 310(P) is arranged so as to define the crossed Nicols state. In the example illustrated in FIG. 3, polarized light when the polarization transmission axis of the polarization filter is perpendicular to the paper is supposed to be P-polarized light, while polarized light when the polarization transmission axis of the polarization filter is parallel to the paper is supposed to be S-polarized light (i.e., S wave).

There are roughly two kinds of reflected light beams to be observed when a shooting session is carried out using a linearly polarized light source 305, 311. One of the two kinds is a specular reflected component 306, 312 produced by getting the incoming light specular-reflected from a projection. The other kind is an internally diffused polarized light beam 308, 313 which has penetrated into the medium to turn into non-polarized scattered light 307 at a deeper layer and then goes out of the surface again through a slope which is tilted with respect to the image capturing system. Such an internally diffused light beam gets polarized significantly if the angle of emittance that is the tilt angle defined between a normal to the boundary plane and the line of sight is large.

Next, the polarization direction of reflected light will be described qualitatively.

First of all, the specular reflected component 306, 312 has been specular-reflected under coaxial illumination, and therefore, maintains the polarization state of the light that has irradiated the object. That is why the specular reflected component 306 becomes a polarized light beam, of which the polarization direction is the direction coming out of the paper, and the specular reflected component 312 becomes a polarized light beam, of which the polarization direction is parallel to the paper.

Figure 4:
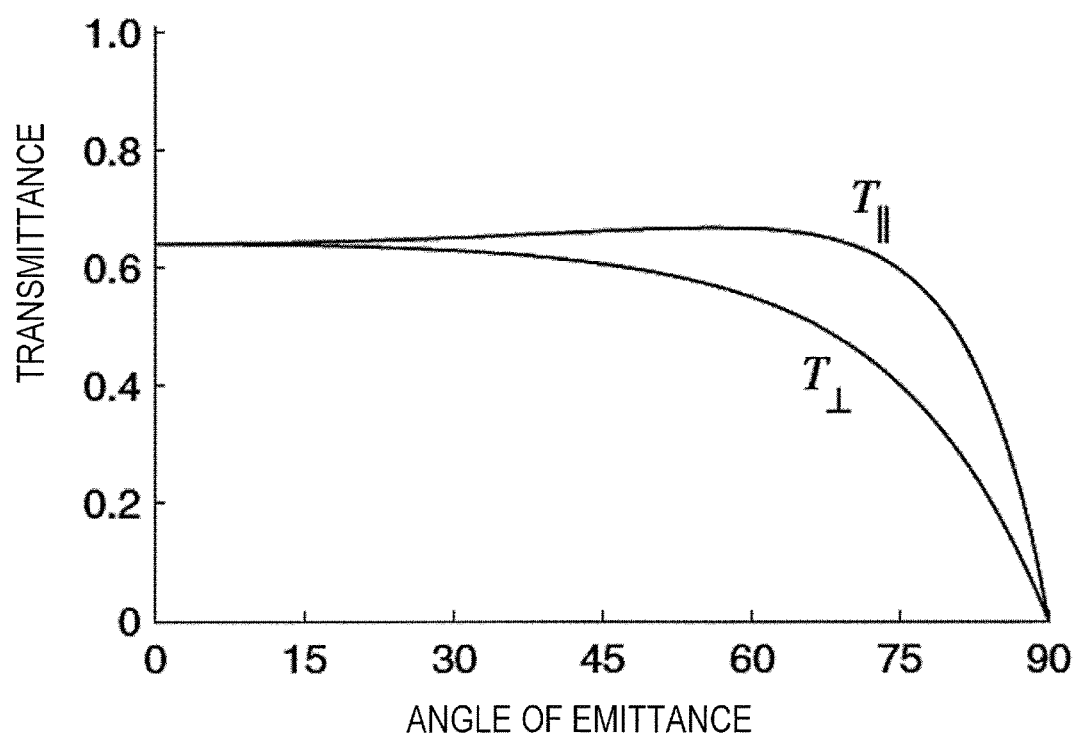
FIG. 4 shows a graph showing a relation between the angle of emittance of a light beam which is going out of a medium and the transmittance.

On the other hand, the polarization direction of the internally diffused polarized light beam 308, 313 is determined by applying the Fresnel theory to a polarized light beam which is going out of a medium, of which the refractive index is greater than one, into the air. FIG. 4 is a graph showing the state of a polarized light beam which is going out of a medium, of which the refractive index is greater than one, into the air. The curves shown in FIG. 4 were obtained based on the Fresnel theory. With respect to the angle of emittance represented by the abscissa, the transmittance always satisfies $T//>T\perp$ (i.e., P polarized light>S polarized light). Consequently, both of the internally diffused polarized light beams 308 and 313 get more P-polarized than S-polarized with respect to the surface tilt of the model 301.

Next, when these reflected light beams are observed at the image capture device 304, the reflected light beam 306 that is P-polarized (i.e., polarized in the direction coming out of the paper) and the reflected light beam 308 that is S-polarized (i.e., polarized in the direction parallel to the paper) are observed by the S-polarization filter 303 in portion (a) of FIG. 3. As a result, the reflected light beam 306 is cut off and looks dark, while the reflected light beam 308 is transmitted and looks bright. That is to say, if the semi-cylindrical portions of the model 301 are observed from right over them, then a striped pattern in which the image looks dark around the center axis but looks bright around the slopes as in the image 314 will be observed clearly. In portion (b) of FIG. 3, on the other hand, the reflected light beams 312 and 313 that are both S-polarized (i.e., polarized in the direction parallel to the paper) are observed by the P-polarization filter 310 of the image capture device 304. As a result, both of these reflected light beams 312 and 313 are cut off and look dark. That is to say, if the semi-cylindrical portions of the model 301 are observed from right over them, then the resultant image will look dark overall as in the image 315 and the micro-geometric pattern will not be sensible clearly.

Figure 5:
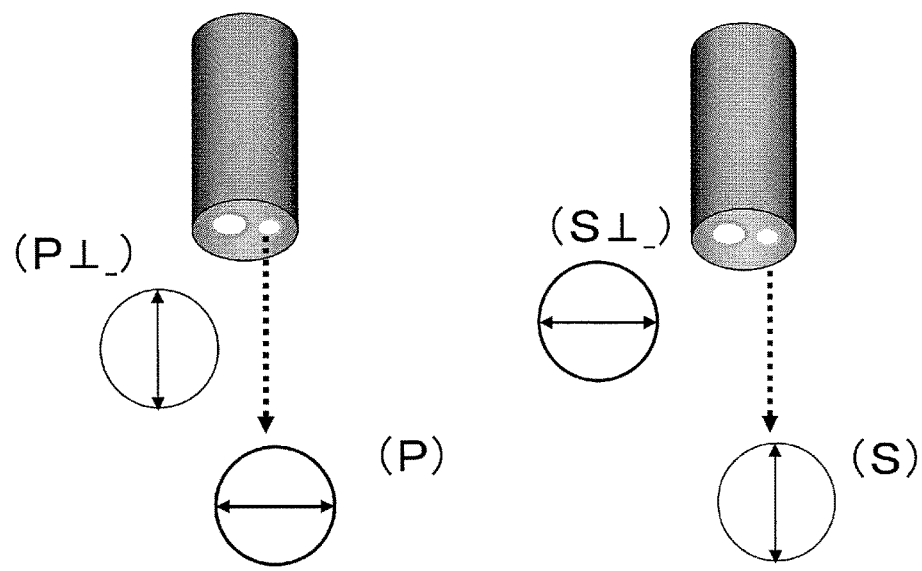
FIG. 5 shows a relation between grooves on an acrylic plate and the directivity of a polarized illuminating light beam when a crossed Nicols image is going to be captured through an acrylic lenticular plate.
Figure 5:
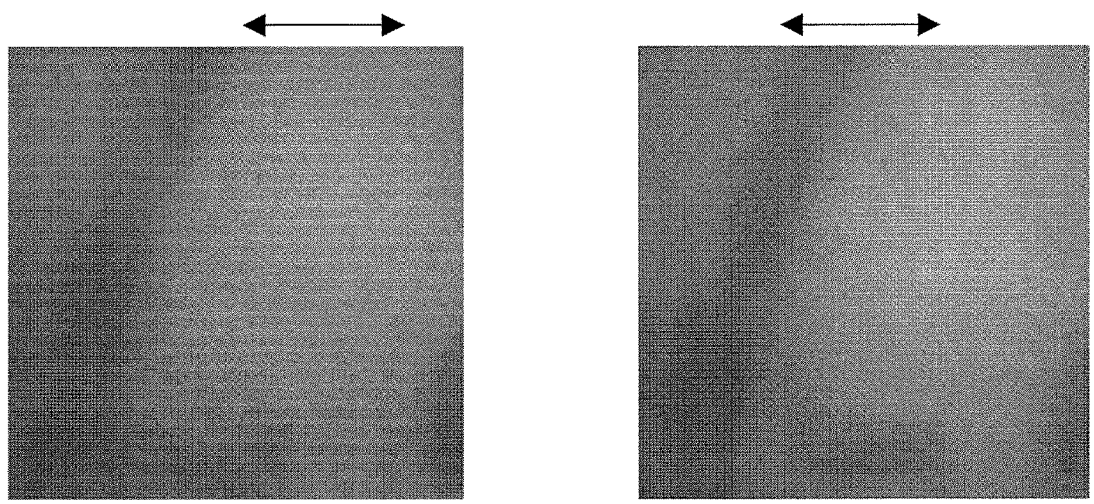

A lenticular plate was prepared by forming a striped micro-geometric pattern (comprised of a lot of grooves) on an acrylic plate and polarization images of the lenticular plate were actually captured. The results are shown in FIG. 5. In this case, the object was obtained by putting a transparent sheet simulating blood vessels on a perfect diffuser plate and then stacking a milky white acrylic lenticular plate with a thickness of 2 mm on the transparent sheet. This object was observed from right over it. The grooves of the lenticular plate were arranged parallel to each other in a zero-degree direction with respect to the horizontal direction on the paper. Portions (a) and (b) of FIG. 5 show images that were shot when the polarized light sources were P-polarized and S-polarized, respectively. That is to say, in portion (a) of FIG. 5, the polarization direction of the polarized light source was parallel to the direction in which the grooves ran on the surface of the object. On the other hand, in portion (b) of FIG. 5, the polarization direction of the polarized light source was perpendicular to the direction in which the grooves ran on the surface of the object. Both of these polarization images shown in portions (a) and (b) of FIG. 5 were captured in the crossed Nicols state. Comparing the crossed Nicols images that were captured then, it can be seen that a bright and dark striped pattern can be clearly observed in the P direction in portion (a) of FIG. 5 but such a bright and dark striped pattern cannot be observed clearly in portion (b) of FIG. 5.

As described above, if a polarized light in the crossed Nicols state is imaged in the polarization image capturing mode and if the polarization direction of the polarized light source is nearly parallel to the depressions (grooves) of the object, then the light intensity will be higher than in the surrounding region and the depressions can be sensed clearly. That is why if it is not known in what direction the depressions and projections of the object run, as long as at least two crossed Nicols images, of which the polarization directions intersect with each other at right angles, can be obtained under a polarized light source, the depressions on the surface can be detected by performing image processing such as differential filter processing. And if the depressions thus detected are colored in blue through color digital image processing, an image similar to the one obtained by sprinkling a blue pigment liquid such as an indigo carmine solution onto a mucosa can be reproduced.

The present inventors discovered and confirmed via experiments that under the coaxial illumination as in an endoscope, if the light intensity of a perfect diffuser plate is one, then the light intensity of a specular reflected light beam becomes as high as about 10 to about 100. That is why if a crossed Nicols image is captured with this high light intensity lowered to the range where the image sensor does not get saturated, a polarization filter with an extinction ratio of 100:1 or more can be used.

Hereinafter, embodiments of the present disclosure will be described.

(Embodiment 1)

Figure 6:
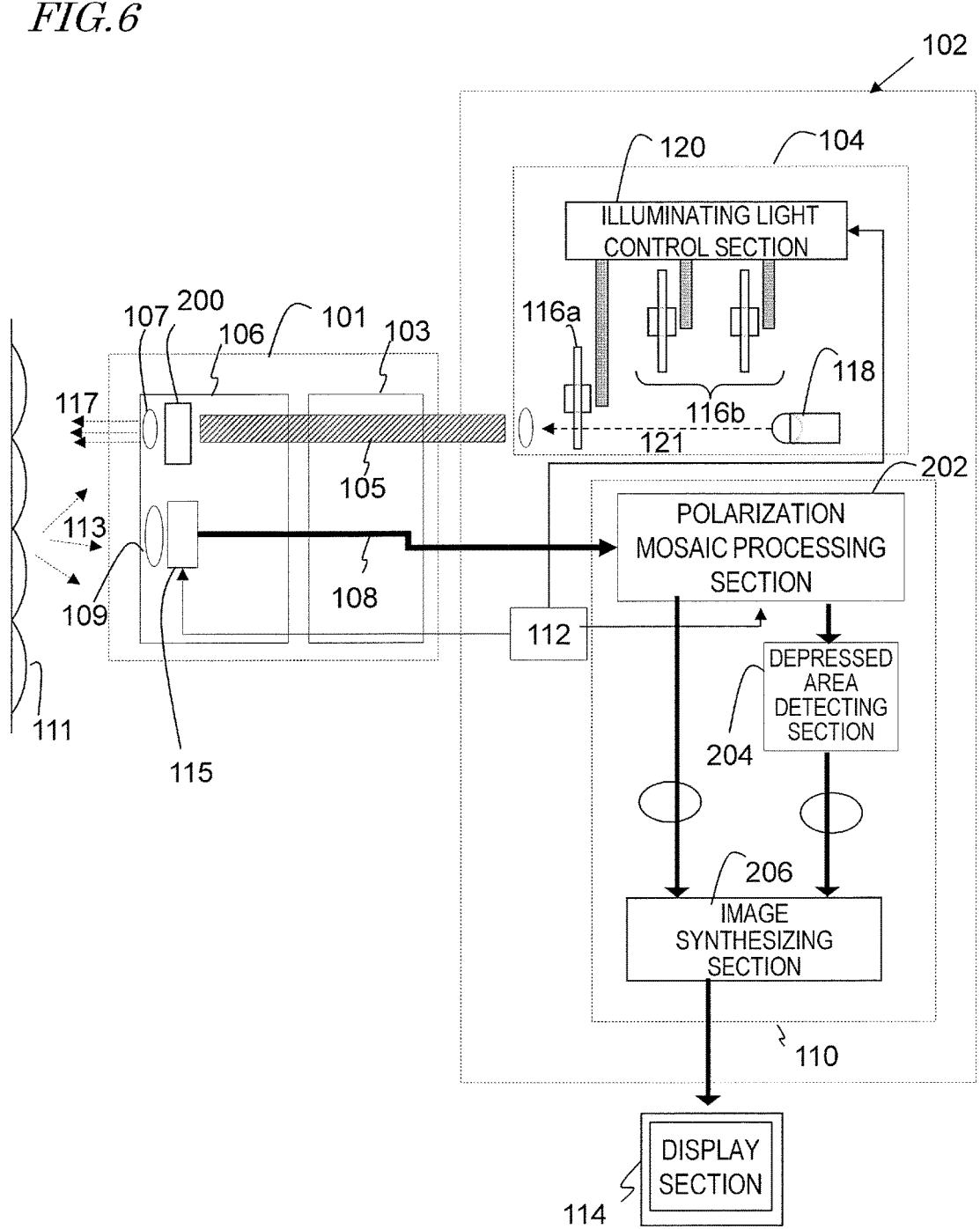
FIG. 6 shows a block diagram illustrating a configuration for a first embodiment of the present disclosure.

FIG. 6 schematically illustrates an overall configuration for an image processing apparatus as a first embodiment of the present disclosure. This image processing apparatus includes an endoscope 101, a controller 102, and a display section 114.

The endoscope 101 includes a tip portion 106 with a monochrome broadband polarization image sensor 115 and an inserting portion 103 with a light guide 105 and a video signal line 108. The inserting portion 103 of the endoscope 101 has a structure that is elongated horizontally as shown in FIG. 6 and that can be bent flexibly. Even when bent, the light guide 105 can also propagate light.

The controller 102 includes a light source unit 104 and an image processor 110. A light source 118 such as a xenon light source, a halogen light source, an LED light source or a laser light source is built in the light source unit 104. The non-polarized light emitted from the light source 118 passes through a color wheel 116a, 116b with turning RGB filters. As a result, red (R), green (G) and blue (B) light beams are produced and then guided to the tip portion 106 through the light guide 105. When transmitted through an illuminating filter 200, each of these light beams turns into either a polarized light beam or a non-polarized light beam. Then, the light beam is further transmitted through an illuminating lens 107 and irradiates the surface of a viscera mucosa 111 that is the object as a polarized or non-polarized illuminating light beam 117. The light 113 reflected from the object is imaged onto the monochrome broadband polarization image sensor 115 through an objective lens 109.

Synchronously with the turn of the color wheel 106a, a synchronizer 112 sends a shooting start signal to the monochrome broadband polarization image sensor 115, thereby getting video based on the reflected light. The video signal thus obtained by capturing the image reaches an image processor 110 through the video signal line 108.

By performing these series of processing by the frame sequential method in which the colors are changed from one of RGB into another, a color image and a polarization image are captured. In the following description, a mode to capture a normal color image will be sometimes referred to herein as either a "non-polarization image capturing mode" or a "normal image capturing mode", while a mode to capture a polarization image will be sometimes referred to herein as a "polarization image capturing mode".

On receiving a signal indicating whether the endoscope should operate in the normal image capturing mode or the polarization image capturing mode from an external device, an illuminating light control section 120 inserts an associated color wheel into the optical path 121 of the illuminating light in response to that signal. In this manner, the spectral property of the illuminating light to irradiate the object frame-sequentially is changed.

If the signal indicates that the endoscope should operate in the normal image capturing mode, color images which have been processed by a polarization mosaic processing section 202 are synthesized together by an image synthesizing section 206 into a full-color moving picture, which is then presented as a movie, for example, on the display section 114. On the other hand, if the signal indicates that the endoscope should operate in the polarization image capturing mode, those images that have been processed by the polarization mosaic processing section 202 have their depressed area detected from their surface by a depressed area detecting section 204, have their color blue portions enhanced by the image synthesizing section 206 and then are presented as a movie, for example, on the display section.

Figure 7:
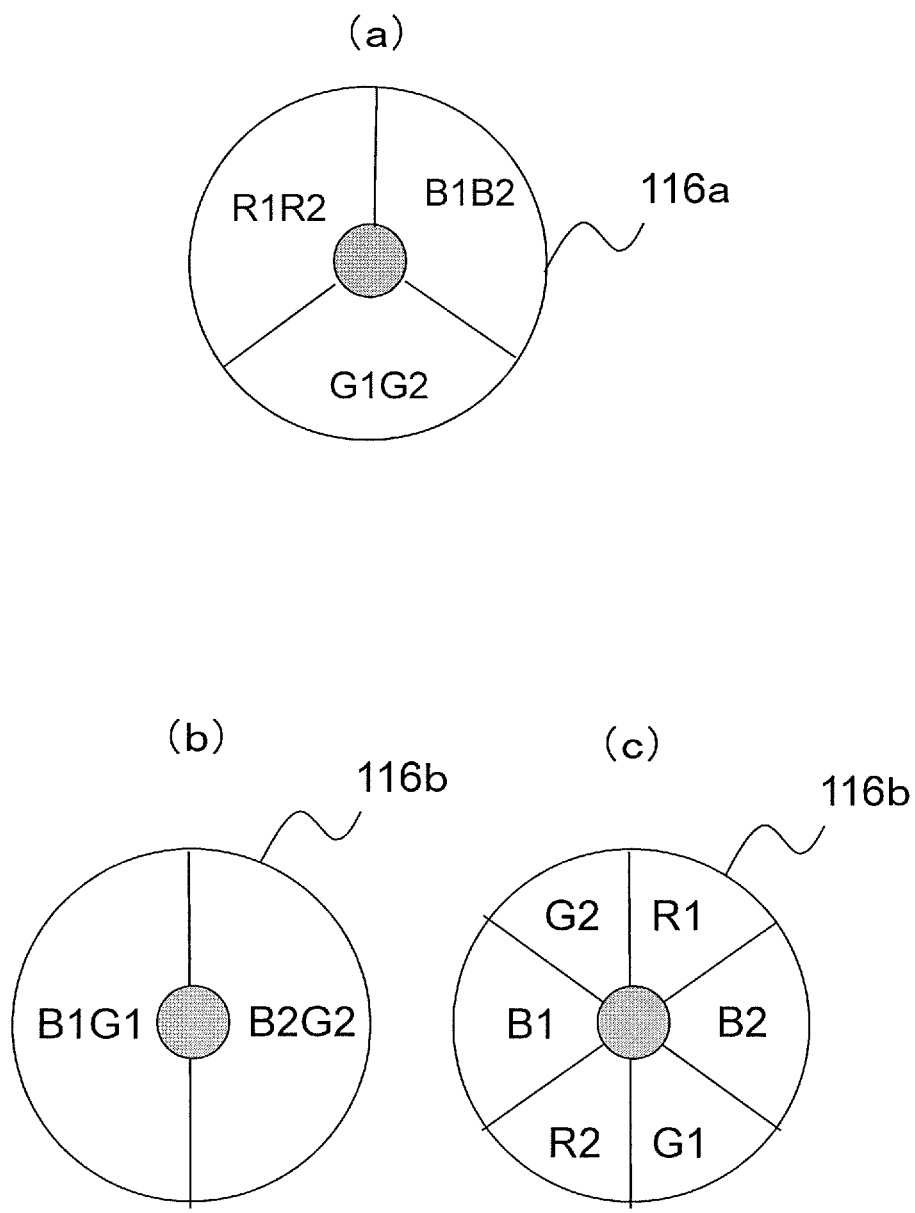
FIG. 7 illustrates color wheels for use in the first embodiment of the present disclosure.

FIG. 7 illustrates examples of color wheels which may be used to filter an illuminating light beam portion (a) of FIG. 7 illustrates a color wheel 116a for use in the normal image capturing mode, which has three fan areas that are arranged around the axis of rotation. These three fan areas are comprised of a red filter which transmits light beams falling within substantially the same color red wavelength ranges R1R2 simultaneously, a green filter which transmits light beams falling within substantially the same color green wavelength ranges G1G2 simultaneously, and a blue filter which transmits light beams falling within substantially the same color blue wavelength ranges B1B2 simultaneously. In this case, R1 and R2 of R1R2 respectively indicate the shorter-wave half and the longer-wave half of the color red (R) wavelength range of 600 to 700 nm, for example. In the color filter 116a shown in portion (a) of FIG. 7, the fan area R1R2 can transmit both a light beam falling within the wavelength range R1 and a light beam falling within the wavelength range R2, and may be identified simply by "R". The same can be said about the other signs "G1G2" and "B1B2", too. In this description, the sign such as R1 is sometimes used to indicate a particular wavelength range and sometimes used to indicate a filter which selectively transmits a light beam falling within such a wavelength range.

A color wheel 116b for use in the polarization image capturing mode may have any of various configurations depending on in what wavelength range a polarization image is going to be captured. FIG. 7(b) illustrates an example of a color wheel 116b which sequentially transmits two light beams falling within two different wavelength ranges where colors green and blue are mixed together. For this color wheel 116b, a wavelength range which can be used effectively to detect a micro-geometric surface texture may be selected. On the other hand, portion (c) of FIG. 7 illustrates another exemplary color wheel 116b which sequentially transmits light beams falling within six different wavelength ranges. The color wheel 116b with such a configuration is suitably used to capture a full-color crossed Nicols image. It should be noted that either the color wheel 116a shown in portion (a) of FIG. 7 or the color wheel 116b shown in portion (b) of FIG. 7 or portion (c) of 7(c) is specified and selectively used in response to a signal supplied from an external device. More specifically, the color wheel 116a is used in the non-polarization image capturing mode or normal image capturing mode, and the color wheel 116b is used in the polarization image capturing mode.

Figure 8:
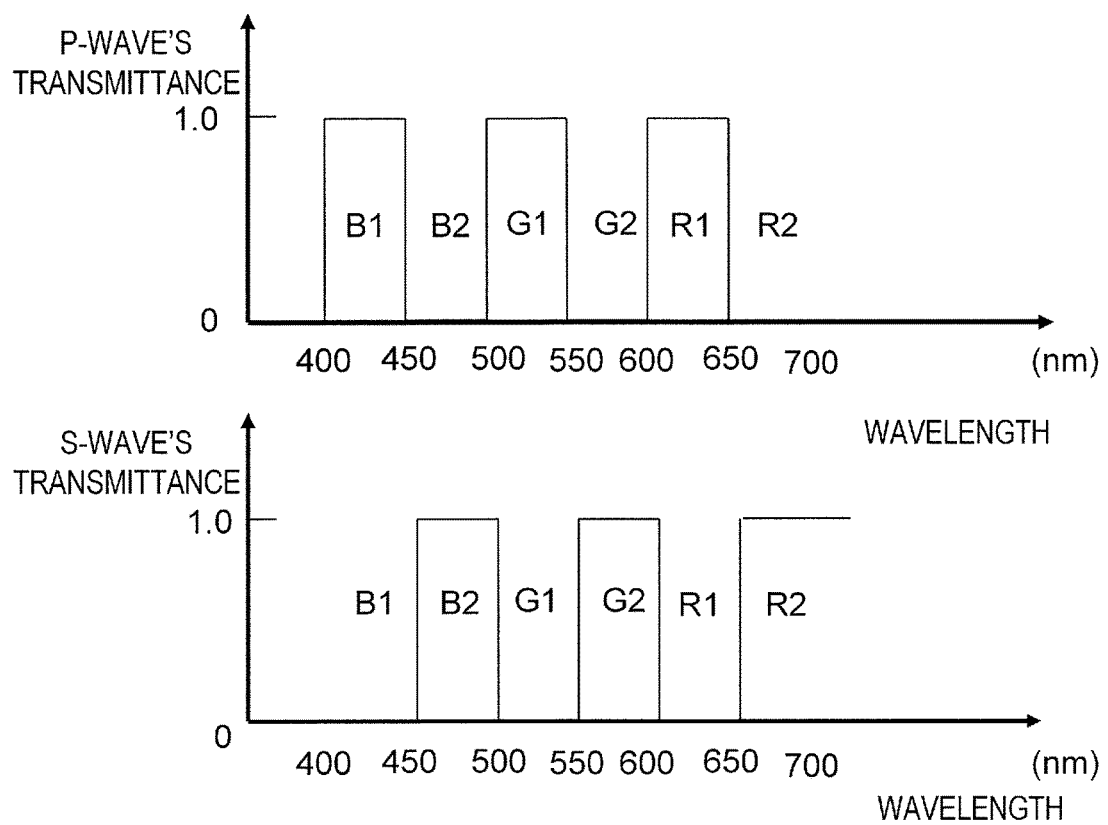
FIG. 8 shows the characteristic of an illuminating filter according to the first embodiment of the present disclosure.

FIG. 8 shows the transmission characteristic of the illuminating filter 200. This filter has a comb transmission characteristic in which P- and S-polarized light beams are transmitted alternately in the respective visible light wavelength ranges of B, G and R. For instance, in the example illustrated in FIG. 8, only a P-polarized light beam is transmitted in the wavelength range B1 (of 400 to 450 nm), and only an S-polarized light beam is transmitted in the wavelength range B2 (of 450 to 500 nm). That is why if the wavelength of the incoming light that has come from the light source through the light guide falls within the wavelength range B1, that incoming light is transformed by the illuminating filter 200 into a P-polarized illuminating light beam. Likewise, if the wavelength of the incoming light that has come from the light source through the light guide falls within the wavelength range B2, that incoming light is transformed by the illuminating filter 200 into an S-polarized illuminating light beam. It should be noted that if the wavelength of the incoming light that has come from the light source through the light guide covers the entire wavelength range B1B2 in the normal image capturing mode, then P- and S-polarized light beams are mixed together, and therefore, a non-polarized illuminating light beam is obtained.

A filter having the characteristic shown in FIG. 8 may be implemented as a multilayer film polarizer as disclosed in Japanese Laid-Open Patent Publication No. 2009-210780, for example.

Figure 9:
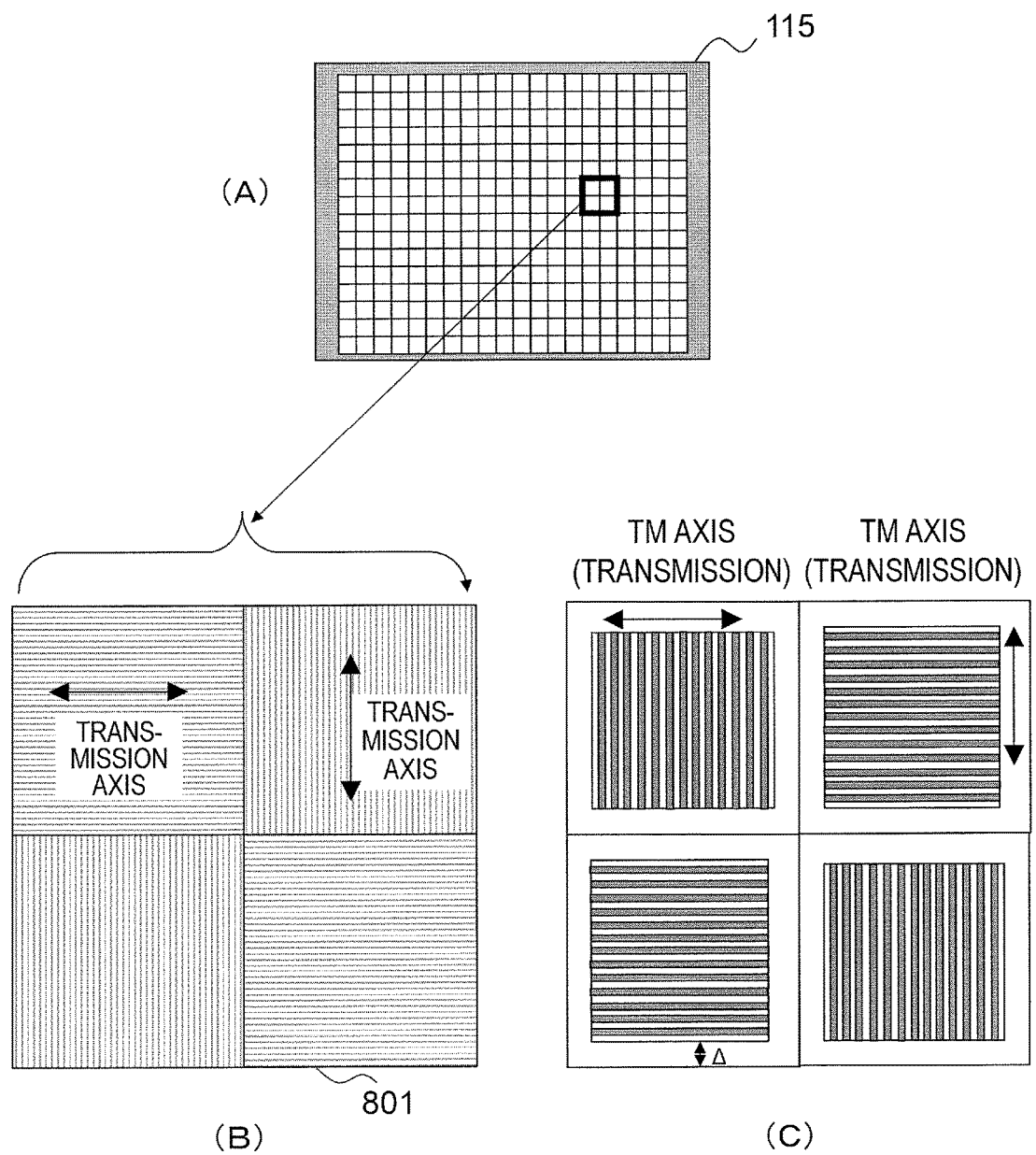
FIG. 9 illustrates the planar structure and transmission axis directions of wire grids which form a monochrome broadband polarization image sensor according to the first embodiment of the present disclosure.

FIG. 9 schematically illustrates an exemplary structure for a patterned polarizer (which is either a polarization mosaic or a polarization mosaic array) on the image capturing plane of the monochrome broadband polarization image sensor 115. As shown in portion (A) of FIG. 9, pixels are arranged regularly in columns and rows (i.e., in the X-Y directions) on the image capturing plane.

Since this image sensor 115 is used in the frame sequential method in which the colors of the illuminating light are changed sequentially from one of RGB into another, no color mosaic filters are arranged on the image capturing plane. That is why the image sensor 115 itself is a monochrome image sensor, and the polarizer is arranged in each pixel. Since light beams falling within visible light wavelength ranges are sequentially incident on the respective pixels, the polarization selection characteristic of the polarizers for use in this embodiment is realized within the visible light wavelength range. Specifically, in the wavelength range of 400 nm to 800 nm, the extinction ratio indicating the polarized light obtaining ability of the polarizers of this embodiment is 100 to 1 or more. For that reason, in this embodiment, polarizers which exhibit polarization properties only at particular wavelengths that form only a narrow part of the visible light wavelength range are not used, but metallic wire grid polarizers which can exhibit high polarized light obtaining ability in a broad wavelength range are adopted instead.

Portion (B) of FIG. 9 illustrates a single unit 801 of the polarization filter which is associated with four pixels that are arranged in two rows and two columns (and which will be sometimes referred to herein as a "2×2 block"). In this single unit 801, four polarization filters (i.e., four polarizers) are arranged by rotating each of these polarization filters 90 degrees within the plane from the adjacent one. In portion (B) of FIG. 9, a number of lines drawn on each polarization filter indicate its polarization transmission axis direction.

Portion (C) of FIG. 9 illustrates an exemplary arrangement of wires in a situation where the polarization filters are implemented as metallic wire grids to have the arrangement shown in portion (B) of FIG. 9. In general, in a wire grid, the direction that intersects at right angles with the direction in which metallic wires run (and which will be referred to herein as a "TM axis") defines the polarization transmission axis. That is why if those wires are represented by straight lines in a schematic representation, then each of the polarization transmission axis directions shown in portion (B) of FIG. 9 is different by 90 degrees from the direction in which an associated set of metallic wires runs in portion (C) of FIG. 9. Thus, to avoid such confusion, when indicating the transmission axis directions of polarization filters for use in an embodiment of the present disclosure, the straight lines (that are parallel to the polarization transmission axes) shown in portion (B) of FIG. 9 will always be used and a plan view illustrating directly the directions in which the wires of the wire grids actually run will not be used.

As will be described later, the arrangement plane of these metallic wire grids may be located at any of various levels from the top through the bottom of the image sensor. In a plan view, these wire grids are arranged in respective inner parts of their areas with some margin A left with respect to the outer periphery of the pixel unit regions to avoid interference with other pixels. If a single pixel region is a square, of which each side has a length D of 3 to 4 µm, the margin Δ may be set to be equal to or greater than 0.2 µm (=200 nm), for example. A tradeoff is inevitable between the transmittance, the extinction ratio and the duty ratio of the width L of each of multiple metallic wires that form these wire grids to their spacing S. In an embodiment of the present disclosure, the width L and spacing S are supposed to be equal to each other. If L=S=0.1 µm=100 nm as will be described later, and if Δ=0.2 µm=200 µm is satisfied and if the directions in which the metallic wires run define angles of 0 and 90 degrees with respect to either the vertical axis or the horizontal axis within the image capturing plane, the number of the metallic wires that form each of these wire grids is 17.

An exemplary conventional polarization image sensor which was actually made using wire grid polarizers of aluminum and which had its performance evaluated in term of the extinction ratio is disclosed in "CCD Polarization Imaging Sensor with Aluminum Nanowire Optical Filters", 30 Aug. 2010/Vol. 18, No. 18/OPTICS EXPRESS pp. 19087-19094 by Viktor Gruev, Rob Perkins, and Timothy York. According to this article, very small wire grid polarizers which were arranged at a pitch P of 140 nm and with a height H of 70 nm within a pixel region with a size of 7.4 µm square had extinction ratios of about 30 to 1, about 45 to 1, and about 60 to 1 at wavelengths of 450 nm, 580 nm and 700 nm, respectively. These results of the actual example reveal that it would be difficult to achieve an extinction ratio of 100 to 1 even if wire grid polarizers of a significantly reduced size were introduced into an image sensor. That is why according to this embodiment, a structure for achieving a high extinction ratio by stacking two wire grid layers one upon the other is adopted instead.

Figure 10:
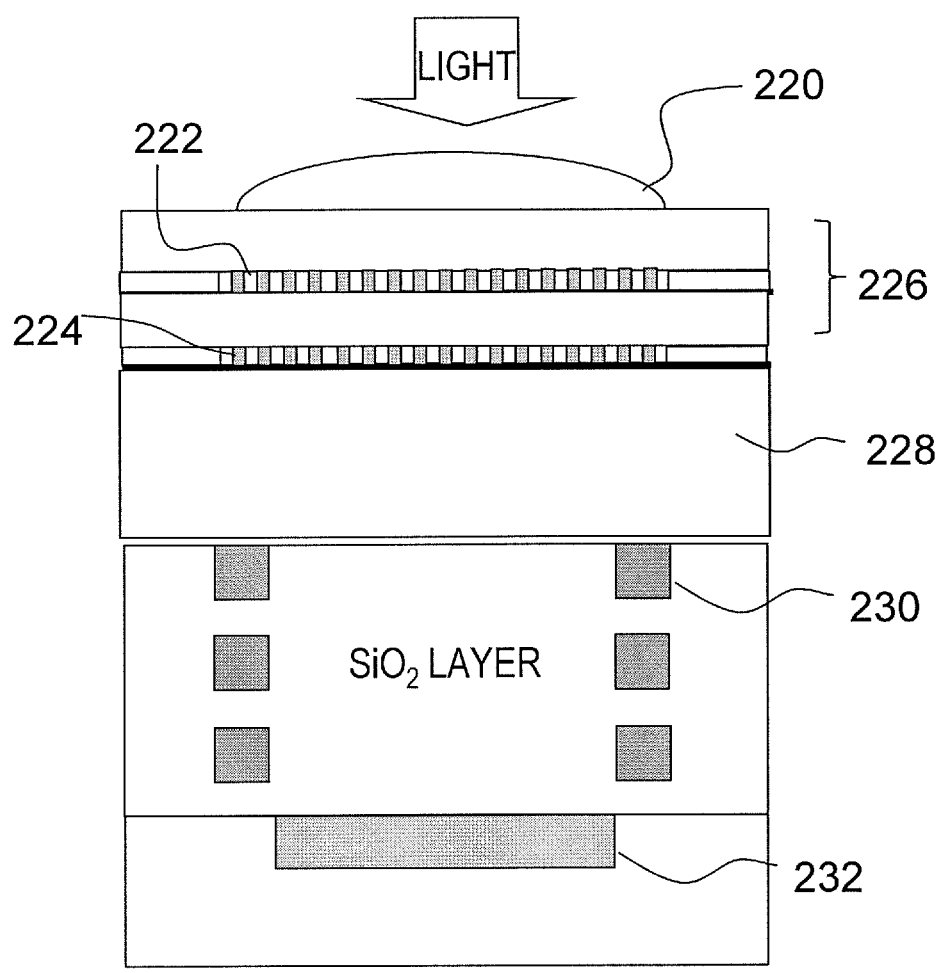
FIG. 10 illustrates a cross-sectional structure of a monochrome broadband polarization image sensor according to the first embodiment of the present disclosure.

Next, an exemplary cross-sectional structure for the image sensor 115 will be described with reference to FIG. 10.

The incoming light reaches the image capturing plane through an objective lens 109 which is arranged over the image sensor 115. In this image sensor 115, the incoming light sequentially reaches its members in the following order. First of all, a micro lens 220 is arranged on the top surface. In this case, the micro lens 220 plays the role of condensing the incoming light efficiently onto the PD (photodiode) 232 but also refracts the optical path of an obliquely incident light beam so that its angle of incidence is almost 90 degrees with respect to the image capturing plane. That is why the micro lens 220 can be used particularly effectively when shooting is often carried out at a wide angle as in an endoscope, for example. In addition, the micro lens 220 can make light incident onto the wire grid layers 222, 224 from substantially right over them, and therefore, can also check the decrease in TM transmittance and extinction ratio. Under the micro lens 220, arranged is a planarizing layer 226, under which the first wire grid layer 222 is arranged to transmit only polarized light beams that are polarized in particular directions (of which the plane of polarization is rotated 90 degrees apiece within the image capturing plane) and to reflect or absorb the other light beams.

In this embodiment, the first wire grid layer 222 has a hollow structure which is defined by the gaps between the metallic wires. Since these metallic wires can keep contact with the air, a decrease in extinction ratio can be avoided effectively.

Under the first wire grid layer 222, arranged is the second wire grid layer 224, which has basically the same arrangement directions, same size, and same hollow structure, and is made of the same material, as the first wire grid layer 222.

By using this stack of the first and second wire grid layers 222 and 224, even if each of these grids is a fine-line wire grid that has had its extinction ratio decreased to about 10 to 1, the overall extinction ratio of these two layers can be increased to approximately 100 to 1. Under the second wire grid layer 224, arranged in this order are a planarizing layer 228 and an interconnection layer 230. In this case, since no interconnects 230 are arranged in the region that should transmit the incoming light, the incoming light can reach the underlying PDs (photodiodes) 232 without being cut by any of those interconnects 230. In the image capturing plane, a lot of PDs 232 are arranged in columns and rows to form a photosensitive cell array.

In general, in an image sensor, it is important to shorten the distance from the micro lens 220 to the PD 232 as much as possible and reduce its overall height. The same can be said about a polarization image sensor according to this embodiment. That is to say, if the distance from the micro lens 220 to the PD 232 is too long, a crosstalk will be produced between pixels to deteriorate the polarization property (e.g., cause a decrease in extinction ratio, in particular). According to this embodiment, the distance from the wire grids to the PD is set to be approximately 2 to 3 µm in order to reduce the overall height. Also, the wire grid polarizer reflects a TE wave, of which the polarization direction intersects at right angles with that of a TM wave to be transmitted, and the reflected TE wave becomes stray light to cause deterioration in performance. Thus, to avoid such a situation, it is effective to form the wire grids 222, 224 as a stack of multiple layers, not a single layer, so that the reflected light is absorbed into those layers stacked. Hereinafter, it will be described how the image processing apparatus of this embodiment performs an image capturing operation.

First of all, it will be described with reference to FIGS. 11A and 11B how the image processing apparatus of this embodiment operates in a normal image capturing mode.

Figure 11A:
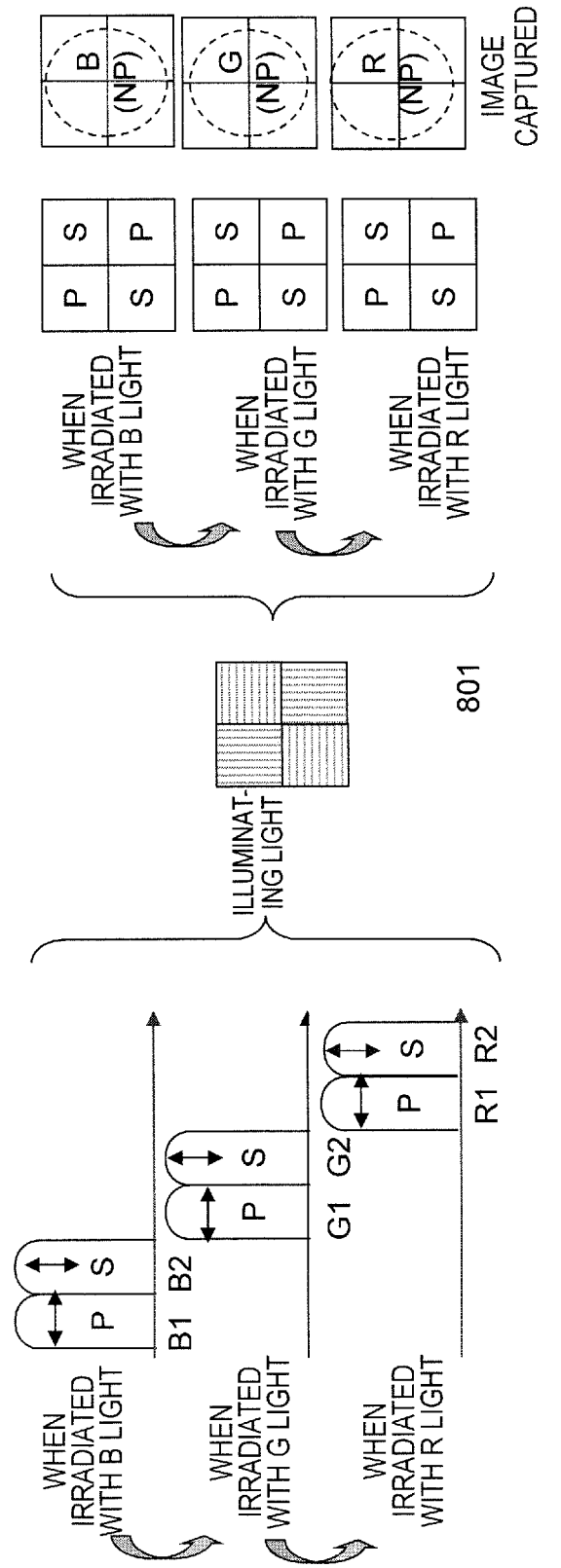
FIG. 11A illustrates how the image processing apparatus according to the first embodiment of the present disclosure operates in a normal image capturing mode.
Figure 11B:
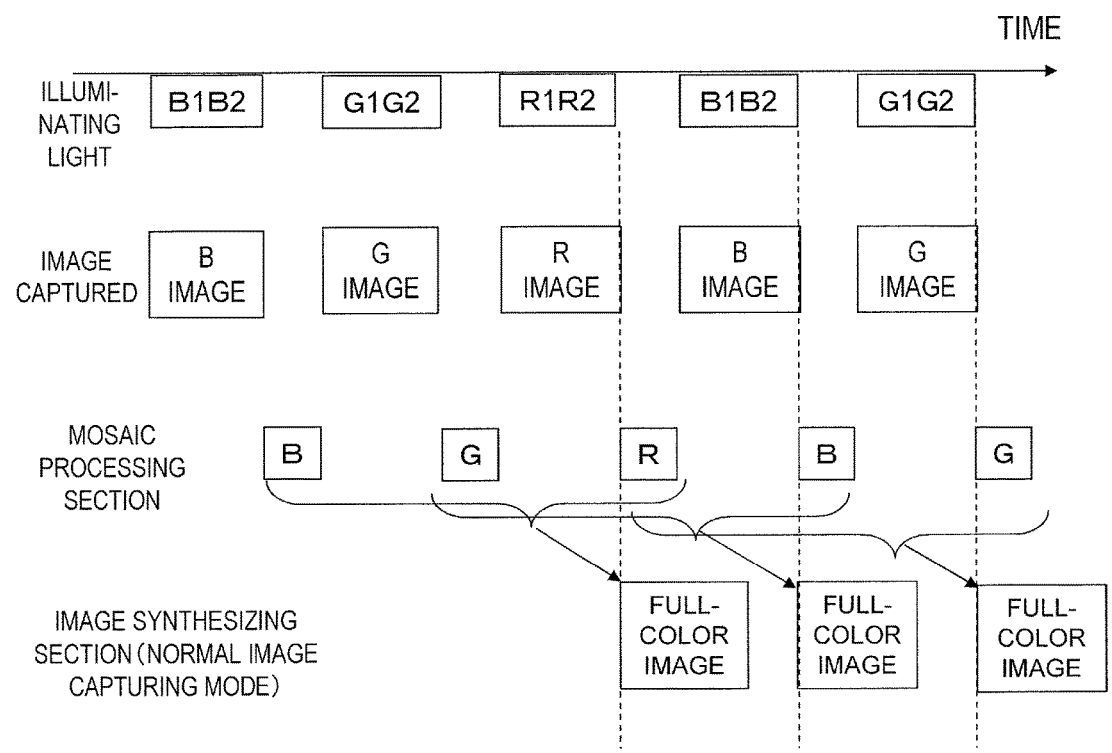
FIG. 11B shows a timing chart showing how the apparatus according to the first embodiment of the present disclosure operates in the normal image capturing mode.

FIG. 11A illustrates how to perform an image capturing operation using respective illuminating light beams in a normal image capturing mode, and FIG. 11B is a timing chart showing the sequence of the image capturing operations. Specifically, the optical spectrum of a frame sequential illumination source is shown on the left-hand side of FIG. 11A. Strictly speaking, a color B illuminating light beam is a mixture of two polarized light beams representing mutually different colors and having mutually different polarization directions (i.e., B1 (P-polarized) and B2 (S-polarized) light beams). The same can be said about the other colors G and R illuminating light beams. When radiated, these illuminating light beams can be regarded as B, G and R non-polarized light beams, respectively. That is why this frame sequential illumination source becomes virtually no different from a known one.

When the object is irradiated with an illuminating light beam, the returning light beam that has been reflected from the object is observed by the monochrome broadband polarization image sensor 105. In FIG. 11A, shown is only a fundamental unit 801 of the polarization mosaic that the polarization image sensor 105 has. Among the four polarizers included in this fundamental unit 801, the two polarizers that are located at the upper left and lower right corners (i.e., P polarization filters) transmit a P-polarized light beam which is polarized horizontally within the image capturing plane. On the other hand, the two polarizers that are located at the upper right and lower left corners (i.e., S polarization filters) transmit an S-polarized light beam which is polarized vertically within the image capturing plane.

The monochrome broadband polarization image sensor 115 performs a polarization operation in the wavelength range of 400 nm to 800 nm, which corresponds to the entire visible light wavelength range. That is why no matter which of the color B, G and R illuminating light beams the object is irradiated with, only a single image sensor can deal with the polarization operation.

The captured image is obtained by getting the light beam that has returned from the object being irradiated with a non-polarized illuminating light beam received via either a P-polarization filter or an S-polarization filter. That is why by averaging the pixel values obtained in a 2×2 pixel region (i.e., consisting of four pixels), a non-polarization image can be obtained. The averaged pixel value is virtually located at the center of the 2×2 (i.e., four) pixels. Thus, on the right-hand side of FIG. 11A, each of the pixel regions indicated by the dotted circles says NP (non-polarization). By shifting the 2×2 (i.e., four) pixels on a pixel-by-pixel basis, the resolution will not decrease substantially.

In this manner, non-polarization images can be captured under the frame sequential non-polarized B, G and R illuminating light beams. By sequentially storing the images in the three primary colors in color image buffer memories and by synthesizing these images together when three-primary-color images are obtained, a full-color moving picture can be generated. This processing will be referred to herein as "polarization mosaic pixel averaging processing", which is carried out by the polarization mosaic processing section 202 shown in FIG. 6. On the other hand, a full-color moving picture is generated by the image synthesizing section 206.

FIG. 11B is a timing chart showing the sequence of these operations. Specifically, the operation of emitting illuminating light beams, the image capturing operation, and the color component images processed by the polarization mosaic processing section 202 are shown in this order from top to bottom of FIG. 11B. The respective operations are performed at these timings by making the synchronizer 112 control the illuminating light control section 120, the monochrome broadband polarization image sensor 115 and the polarization mosaic processing section 202.

Next, it will be described with reference to FIGS. and 13 how the image processing apparatus of this embodiment operates in the polarization image capturing mode.

Figure 12:
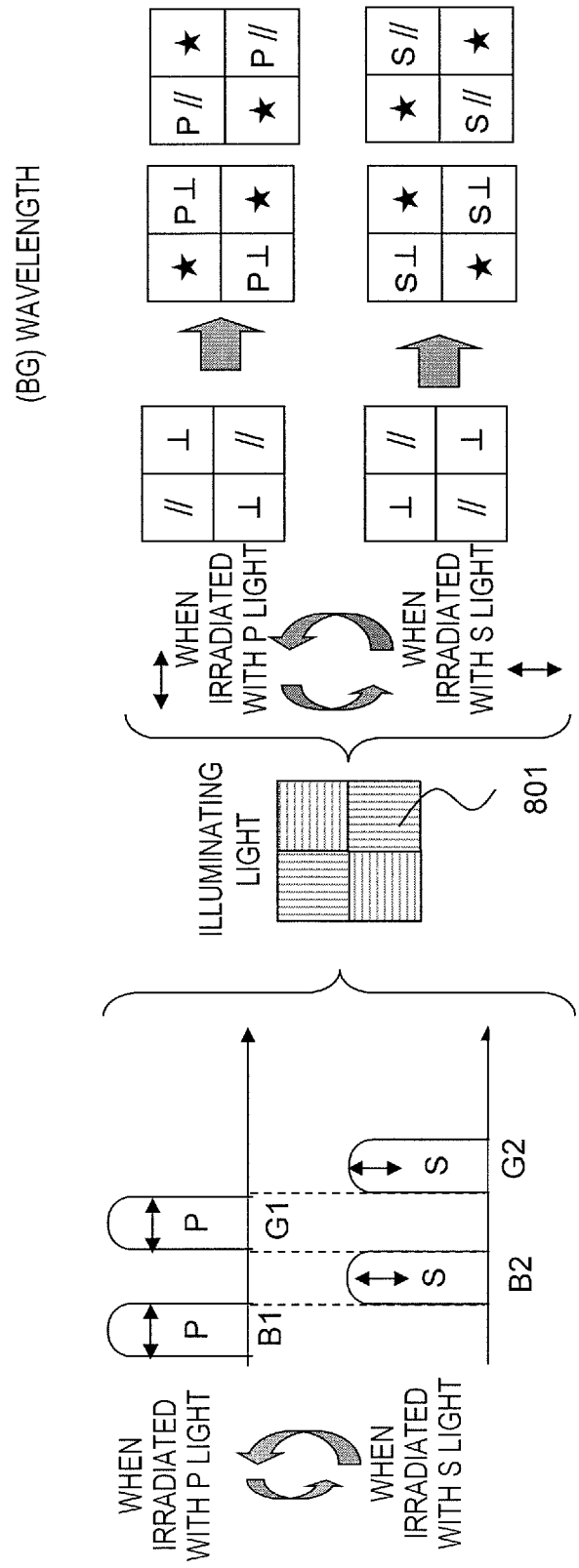
FIG. 12 illustrates how a polarization mosaic processing section 202 operates in a polarization image capturing mode according to the first embodiment of the present disclosure.
Figure 13:
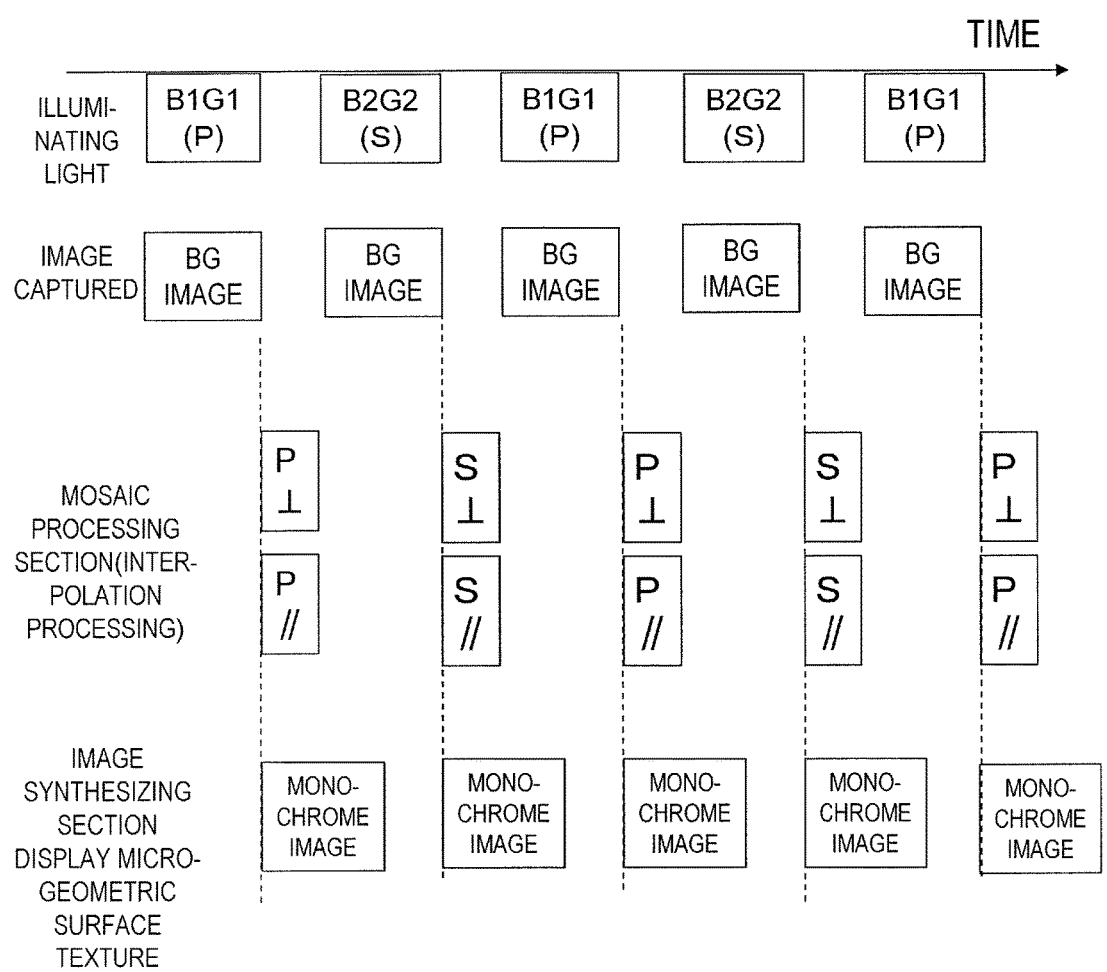
FIG. 13 shows a timing chart showing how the apparatus according to the first embodiment of the present disclosure operates in the polarization image capturing mode.

FIG. 12 illustrates generally how to perform an image capturing operation using respective illuminating light beams in a polarization image capturing mode, and FIG. 13 is a timing chart showing the sequence of the image capturing operation. In this example, the polarization image capturing color wheel shown in portion (a) of FIG. 7 is used.

The optical spectrum of a frame sequential illumination source is shown on the left-hand side of FIG. 12. These colors B and G illuminating light beams are determined in view of the mucosa property of the object such as a digestive organ. The B and G wavelength ranges are shorter than the R wavelength range, and therefore, will cause surface scattering more easily and are suited to observing the light scattered from the surface texture. In addition, in the B and G wavelength ranges, the light reflected from the organism's mucosa is absorbed so deeply that the contrast ratio becomes high enough to observe the micro-geometric surface texture.

In this embodiment, by turning the polarization image capturing color wheel, the object is irradiated alternately with B1G1 which is a P-polarized light beam and B2G2 which is an S-polarized light beam. When the object is irradiated with an illuminating light beam, the returning light beam that has been reflected from the object is observed by the monochrome broadband polarization image sensor 105. At the fundamental unit 801 of the polarization mosaic, multiple different polarization components are measured. Specifically, four kinds of pixel information about a crossed-Nicols pixel (P⊥) and a parallel-Nicols pixel (P//) under a P-polarized illuminating light beam and about a crossed-Nicols pixel (S⊥) and a parallel-Nicols pixel (S//) under an S-polarized illuminating light beam are obtained. Nevertheless, a pixel value which is spatially missing as a piece of pixel information and which is indicated by the solid star ★ needs to be obtained by making interpolation using the values of the surrounding pixels. This interpolation processing may be carried out as simple averaging processing on the four surrounding pixels.

FIG. 13 is a timing chart showing the sequence of these operations. Specifically, the operation of emitting illuminating light beams, the image capturing operation, and the color component images processed by the mosaic processing section are shown in this order from top to bottom of FIG. 13. The respective operations are performed at these timings under the control of the synchronizer 112. When the object is alternately irradiated with a P-polarized light beam and an S-polarized light beam, their corresponding crossed-Nicols images (P⊥) (S⊥) and parallel-Nicols images (P//) (S//) are output as monochrome images. In this description, the "monochrome image" refers herein to a light intensity image providing polarization information in the B and G wavelength ranges. By displaying the crossed-Nicols images (P⊥) (S⊥) alternately and continuously, an image which allows the viewer to sense clearly even the invisible surface micro-geometry such as the one shown in FIG. 5 can be obtained.

Figure 14:
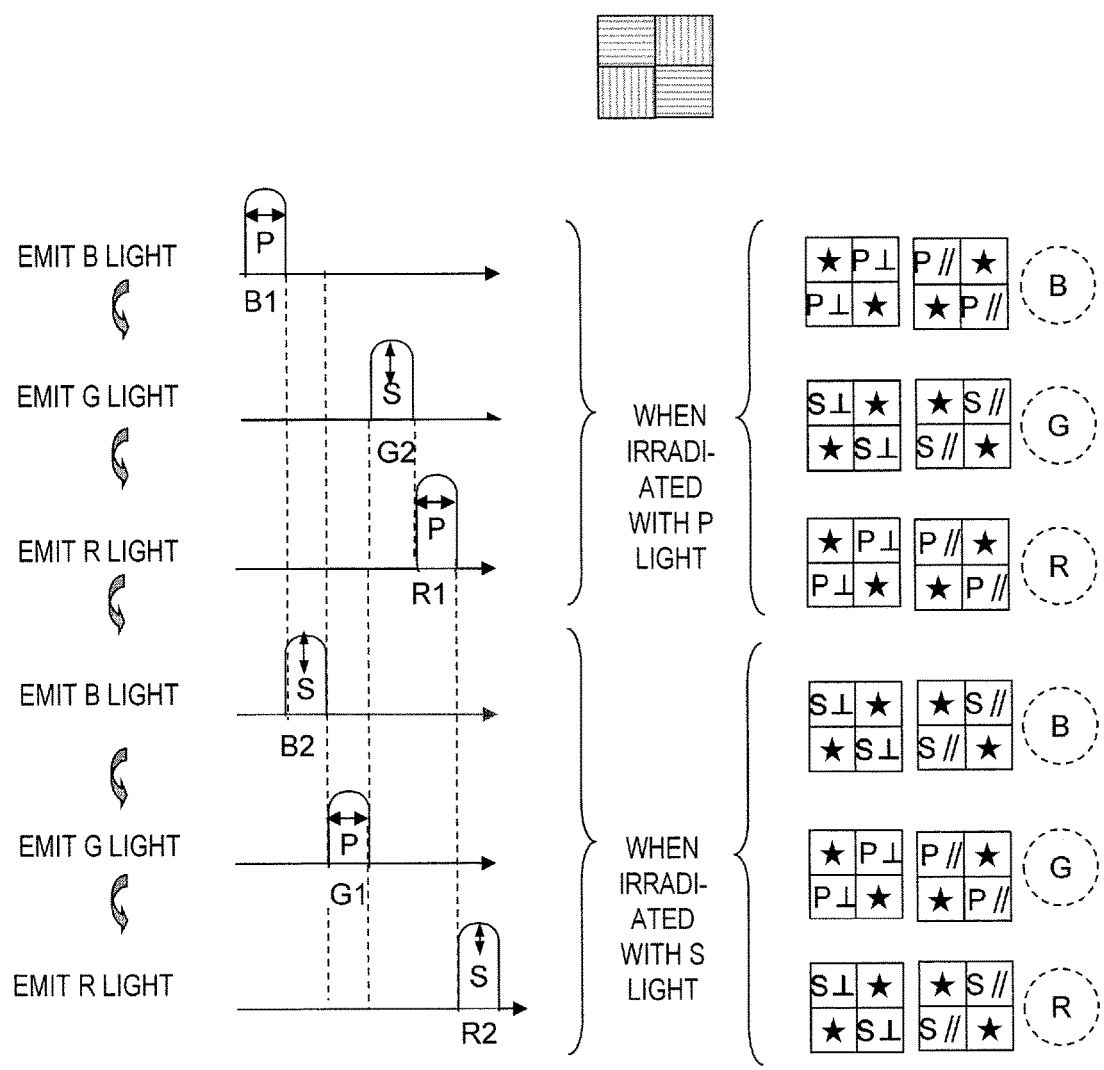
FIG. 14 illustrates how the polarization mosaic processing section 202 operates in the polarization image capturing mode according to the first embodiment of the present disclosure.
Figure 15:
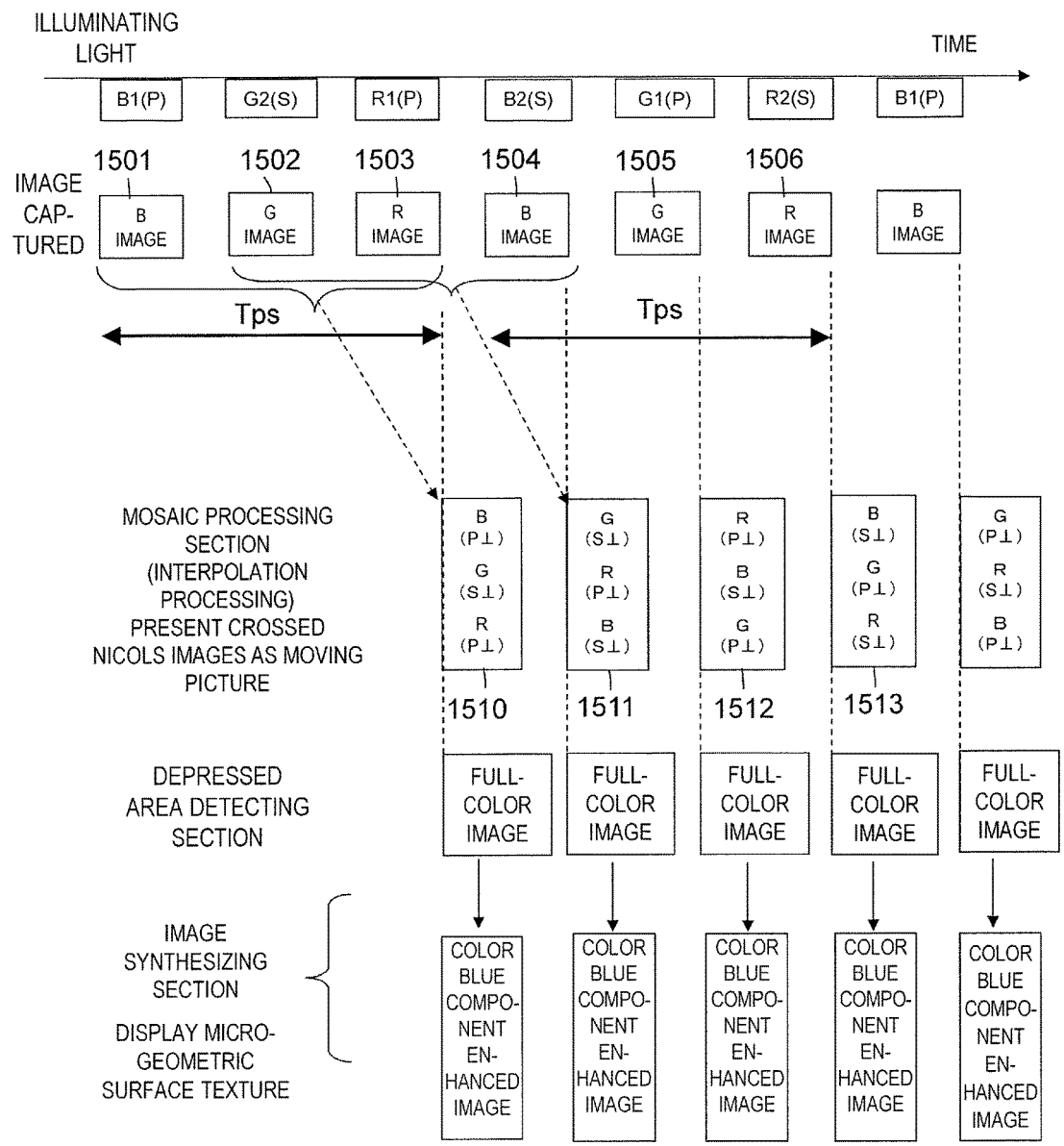
FIG. 15 shows a timing chart showing how the apparatus according to the first embodiment of the present disclosure operates in the polarization image capturing mode.

FIG. 14 illustrates generally how to perform an image capturing operation using respective illuminating light beams in the polarization image capturing mode when the polarization image capturing color wheel shown in portion (c) of FIG. 7 is used, and FIG. 15 is a timing chart showing the sequence of the image capturing operations. In this example, BGR frame sequential color illuminating light beams are used. Such an image capturing technique is applicable particularly effectively to a situation where the surface of a mucosa needs to be observed with the naked eye with specular reflection eliminated. This technique can also be used effectively when the polarization property inside an organism's mucosa should be observed within a narrow wavelength range.

By turning the polarization image capturing color wheel shown in portion (c) of FIG. 7, the object is sequentially irradiated with B1, G1 and R1 which are P-polarized light beams and B2, G2 and R2 which are S-polarized light beams. The returning light beam that has been reflected from the object is observed by the monochrome broadband polarization image sensor 105. And at the fundamental unit 801 of the polarization mosaic, multiple different components are captured. The image thus captured becomes image information comprised of twelve different components that are crossed-Nicols (P⊥) and parallel-Nicols (P//) RGB full-color components under a P-polarized illuminating light beam and crossed-Nicols (S⊥) and parallel-Nicols (S//) components falling within the RGB wavelength ranges under an S-polarized illuminating light beam. In this case, since some portions of the pixel information are also missing, pixel values indicated by the solid star ★ need to be obtained by making interpolation using the values of the surrounding pixels. By adopting such a configuration, when the object is observed in real time through an endoscope, the state of the mucosa can be observed easily with specular reflected components removed from the surface of the mucosa. In this example, in order to reproduce a moving picture quickly, the filters on the circumference of the wheel are arranged in the order of B1-G2-R1-B2-G1-R2, thereby making the colors RGB and P- and S-polarizations alternate with each other.

FIG. 15 is a timing chart showing the sequence of these operations. Specifically, the operation of emitting illuminating light beams, the image capturing operation, and the color component images processed by the mosaic processing section are shown in this order from top to bottom of FIG. 15. The respective operations are performed at these timings under the control of the synchronizer 112. When the object is alternately irradiated with a P-polarized light beam and an S-polarized light beam, their corresponding crossed-Nicols images (P⊥) (S⊥) and parallel-Nicols images (P//) (S//) are output. However, to obtain crossed-Nicols (P⊥) or (S⊥) RGB full-color images, it takes a period of time Tps in which the object is irradiated with B, G and R frame sequential light beams with the polarized illuminating light sources fixed. That is why no moving picture can be displayed during this period of time. The reason is that polarized illuminating light beams and color illuminating light beams are both radiated frame sequentially, and therefore, it takes some time to get every kind of illuminating light beam radiated. In observing the object through an endoscope, however, the operation should be reproduced in real time. For that reason, according to this embodiment, in order to present crossed-Nicols images as a moving picture, images in which (P⊥) and (S⊥) have been mixed together as much as possible are processed and displayed by the pipeline method. For example, the RGB full-color crossed-Nicols image 1510 shown in FIG. 15 is a crossed-Nicols image in which an image 1501 under a B1 (P) illuminating light beam, an image 1502 under a G2 (S) illuminating light beam, and an image 1503 under an R1 (P) illuminating light beam are mixed together under P- and S-polarized light beams. Likewise, the image 1511 to be processed and displayed at the next timing is a crossed-Nicols image in which the image 1502 under the G2 (S) illuminating light beam, the image 1503 under the R1 (P) illuminating light beam, and an image 1504 under a B2 (S) illuminating light beam are mixed together under P- and S-polarized light beams.

If such processing is carried out, P⊥ and S⊥ included in illuminating light beams for crossed Nicols images can be well balanced, which will work fine when a depressed area needs to be detected after that. In addition, by making the BGR color frame sequential light beams change more quickly than the polarized light beams, when the series of images is observed as a moving picture by a human viewer, he or she can still find the moving picture to be a series of color images.

Figure 16:
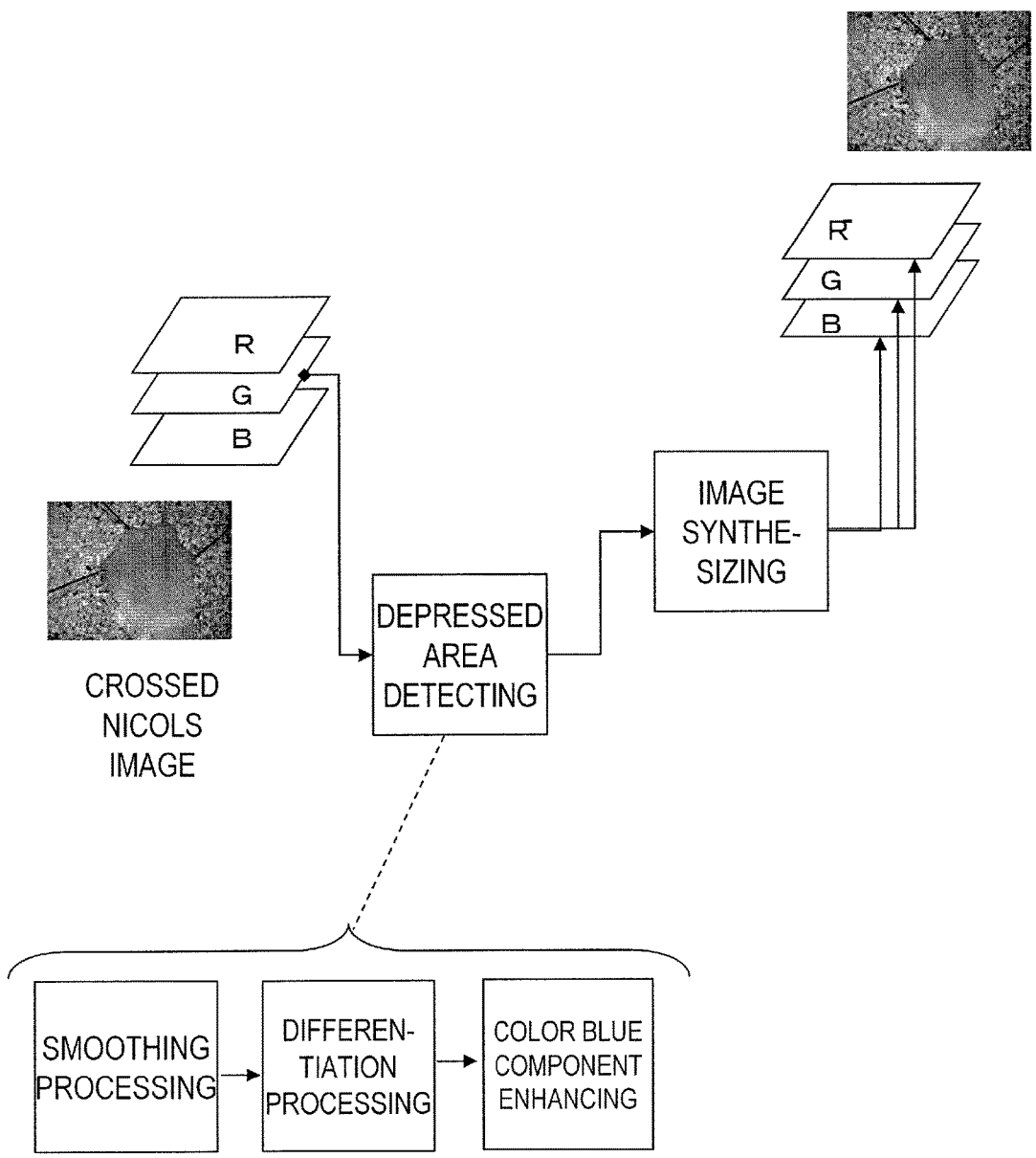
FIG. 16 shows a block diagram illustrating how a depressed area detecting section 204 and an image synthesizing section 206 perform their processing in the first embodiment of the present disclosure.
Figure 17:
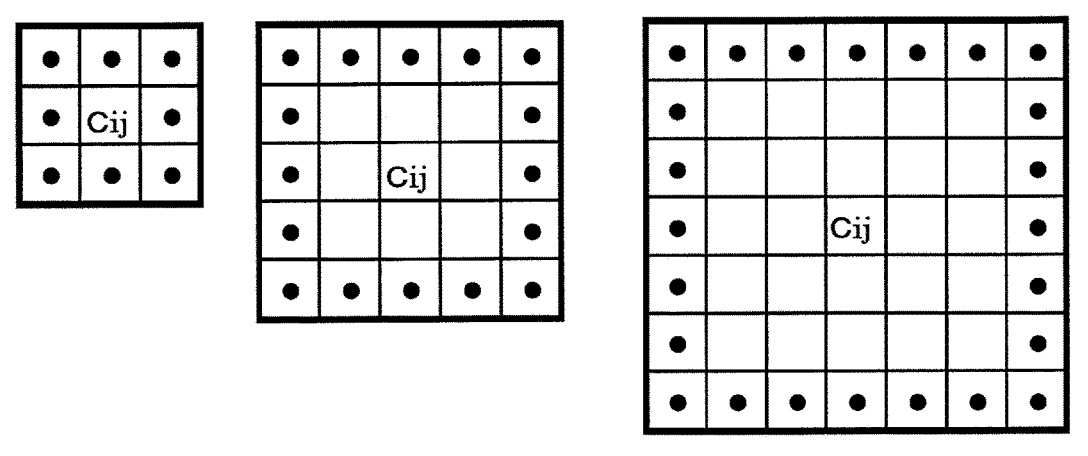

FIG. 16 illustrates how the depressed area detecting section 204 and the image synthesizing section 206 perform their processing. FIG. 17 illustrates exemplary patterns to mask peripheral pixel locations which are used to calculate the difference between the center pixel value and the average of surrounding pixel values. The depressed area detecting section 204 receives the crossed-Nicols images generated by the processing described above.

Hereinafter, it will be described, just as an example, what processing may be carried out in a situation where the full-color crossed-Nicols images that have already been described with reference to FIGS. 14 and 15 are obtained every frame. In this example, a G component is extracted from each of the crossed-Nicols images that are made up of full-color RGB components, and subjected to the smoothing processing, differentiation processing and color blue enhancement processing shown in FIG. 16 in this order.

(1) Smoothing Processing

Before being subjected to the differentiation processing on the next stage, the input image has its noise components, of which the frequencies are higher than the frequency of the texture to be enhanced, removed. Specifically, to remove such noise components, smoothing filter processing is carried out. In this embodiment, a general Gaussian filter is used for that purpose. If the mask size of the filter is set to be the same as the mask size of a differentiation mask filter to be described later, it is possible to avoid enhancing fine granular noise.

(2) Differentiation Processing

To detect a pixel region which is brighter than the surrounding area with respect to the G component image that has been subjected to the smoothing filter processing, the following differentiation mask processing is carried out. Such a pixel region that is brighter than the surrounding area needs to be detected because as already described with reference to FIGS. 3 through 5, if the polarization direction of a polarized illuminating light beam is nearly parallel to the grooves on the surface of the object, the light intensity becomes higher than in the surrounding area. Actually, the directions in which the depressions and projections run on the surface of the object are unknown. However, this is not a problem because according to an embodiment of the present disclosure, the polarization direction of a polarized illuminating light source alternately changes from one of two orthogonal directions into the other, and two kinds of crossed-Nicols images (P⊥) and (S⊥) can be obtained alternately. This differentiation processing is carried out by setting a mask that specifies a center pixel and surrounding pixels such as any of the ones shown in FIG. 17 (in which examples of 3×3 pixels, 5×5 pixels and 7×7 pixels are shown) with respect to the image that has gone through the smoothing processing and by calculating the differential value Δ between the average of the pixel values Vkl of surrounding N=8 pixels, N=16 pixels, or N=24 pixels and the center pixel value Cij. The differential value Δ thus obtained is represented by the following Equation (1):

$$\Delta = C_{ij} - \frac{1}{N} \sum_{kl} (V_{kl}) \quad (1)$$

If the center pixel value indicates that the pixel is brighter than the surrounding pixels, ΔC is set to be a value obtained by multiplying the differential value Δ by k. On the other hand, if the center pixel is darker than the surrounding pixels, ΔC is set to be zero, as indicated by the following Equations (2):

If (Δ>0) is satisfied, then ΔC=k*Δ

Otherwise, ΔC=0 (2)

(3) Color Blue Component Enhancement

By subtracting the ΔC value from R and G components, the color blue component is enhanced. In this case, if the R and G components become equal to or smaller than zero, then continuity is maintained by subtracting the deficit from other color components. That is why the hue changes according to the magnitude of Δ but smooth connection can still be made. Supposing one of the R and G components that has the smaller value is C1 and the other having the larger value is C2, the situations are classified into the following three cases.

Figure 18:
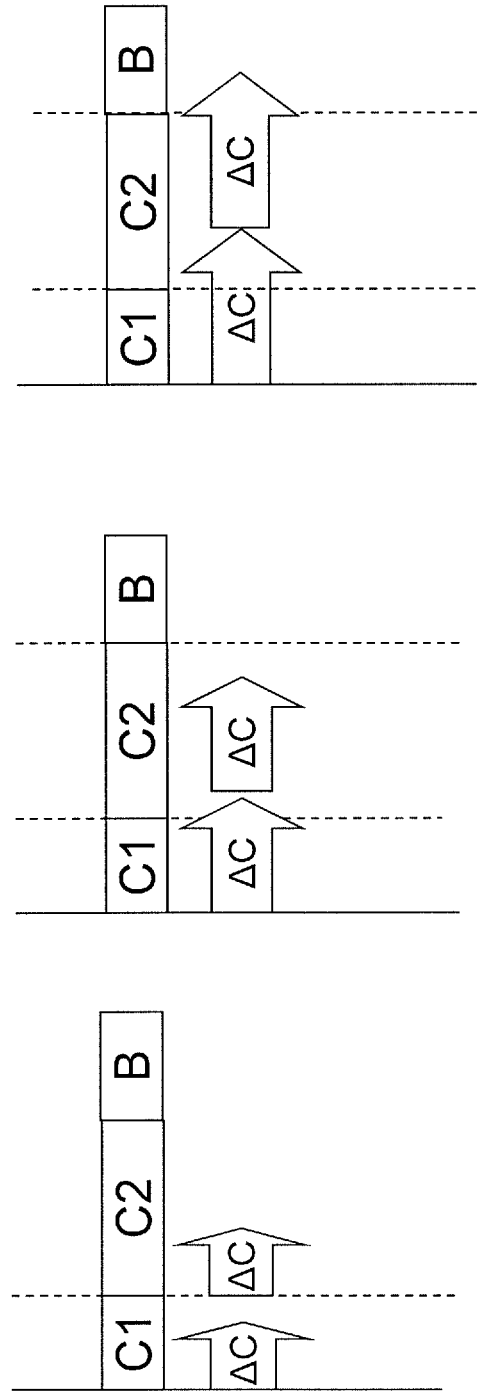
FIG. 18 shows how the depressed area detecting section 204 performs color blue enhancing processing.

FIG. 18 shows the following three cases.

First of all, 1) if ΔC is small, then the processing of subtracting ΔC from the R and G signals is carried out. Next, 2) if ΔC is a value that is greater than C1, then the smallest signal becomes equal to zero and the other signals are subtracted from an intermediate signal. Next, 3) if the result of the subtraction from the R and G signals becomes equal to zero, then the other signal is subtracted from the B signal. By performing these processing steps, a color signal in a pixel region in which the center pixel is brighter than the surrounding pixels has its color blue component enhanced according to its degree, thus generating a color image similar to the one obtained by sprinkling an indigo carmine solution.

1) If ΔC≤C1,
then C1=C1−ΔC, and
C2=C2−ΔC;

2) If $C1 < \Delta C \leq (C1+C2)/2$,
then $C1=0$, and $C2=(C1+C2)-(2\Delta C)$; and
3) If $(C1+C2)/2 < (\Delta C)$,
then $C1=0$ $C2=0$, and
$B=B-((2\Delta C)-C1-C2)$ (4) Image Synthesizing Section's Processing As shown in FIG. 15, the image synthesizing section 206 stores three images (RGB images) that have been obtained under the frame sequential illuminating light beams, and synthesizes together the RGB images on a frame-by-frame basis, thereby generating a full-color image to be displayed in real time. In addition, the image synthesizing section 206 also presents a full-color image, obtained by enhancing the depressions of the surface texture with the color blue component, at regular intervals of one frame period without a delay.

Figure 19:
FIG. 19 shows the results of experiments which were carried out on the mucosa of a rat's stomach.
Figure 19:
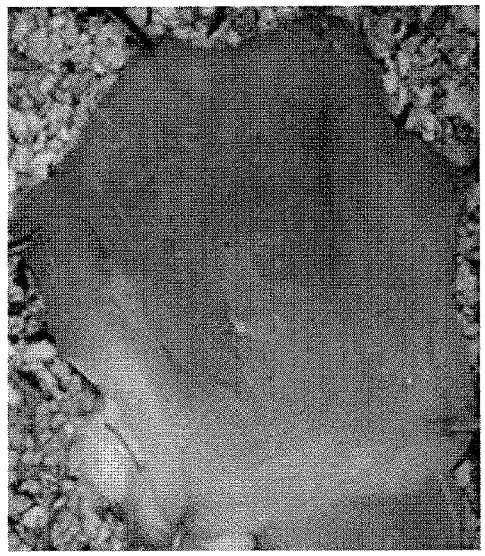
Figure 19:
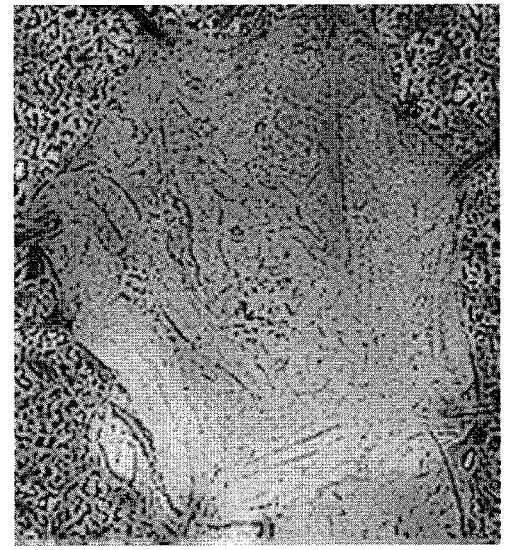

FIG. 19 shows exemplary images obtained by the image processing apparatus of this embodiment. In this case, the object was the mucosa of a rat's stomach which was obtained by dissecting the rat's stomach and then extending and fixing it on a cork board. Specifically, portions (A) and (B) of FIG. are respectively a parallel-Nicols image and a crossed-Nicols image of that object, and portion (C) of FIG. 19 is an image obtained by performing the depression sensing processing of this embodiment. Although a monochrome image is shown in portion (C) of FIG. 19, the image actually obtained was a full-color image in which the micro-geometric surface texture on the surface mucosa of the stomach had been detected and retouched as if the object were colored in blue.

(Embodiment 2)

Figure 20:
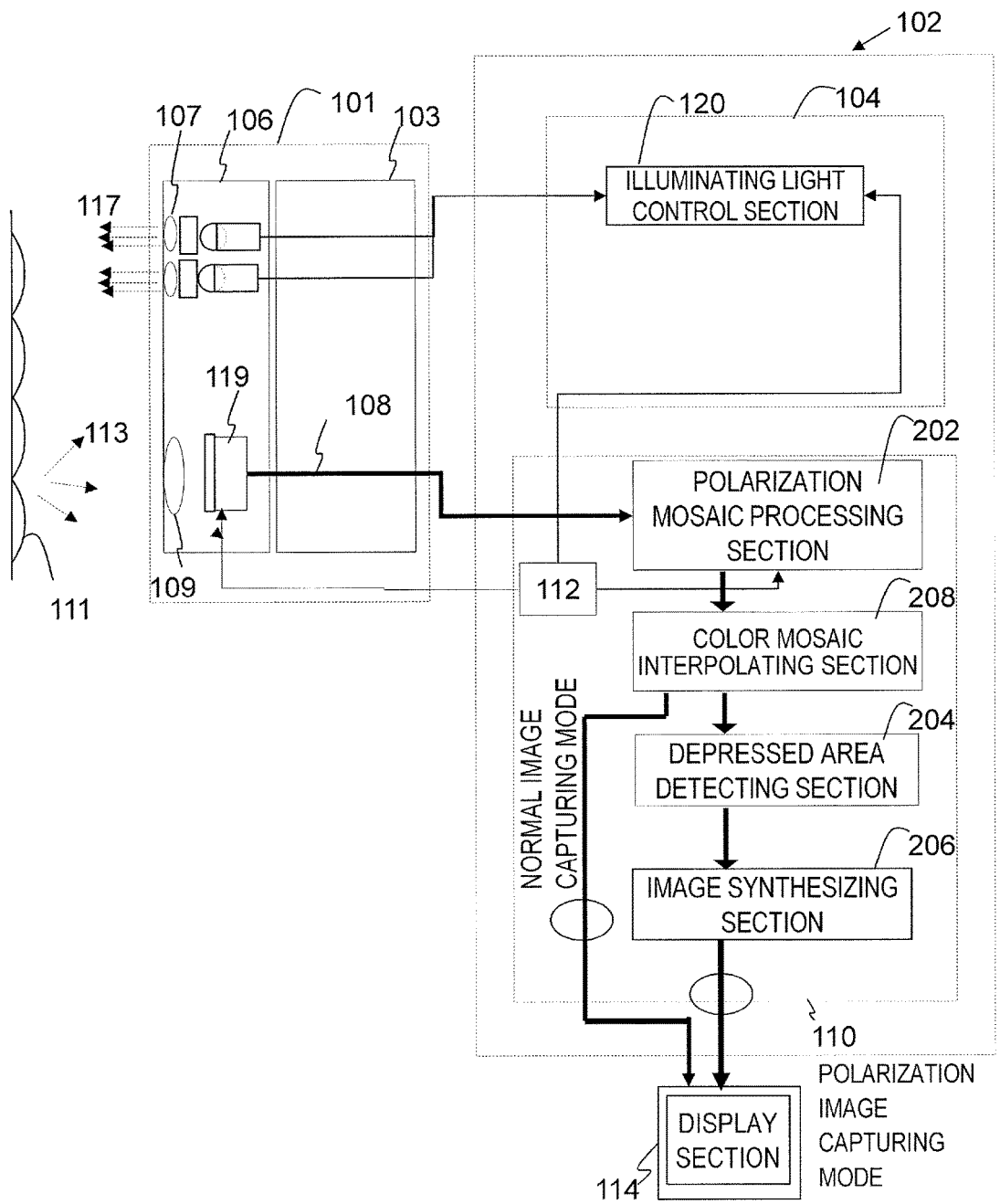
FIG. 20 shows a block diagram illustrating a configuration for a second embodiment of the present disclosure.

FIG. 20 schematically illustrates an overall configuration for an image processing apparatus as a second embodiment of the present disclosure. In this embodiment, the object is irradiated with white light and a color image is captured by a single-panel color image sensor 119. In this embodiment, when the object is irradiated with the white light, a spinning polarized illuminating light source should be used. For that purpose, according to this embodiment, only an illuminating light control section is arranged in the light source unit 104 and illuminating light is produced by either an LED which is arranged at the tip of the endoscope or an organic EL surface-emitting light source, for example.

Figure 21:
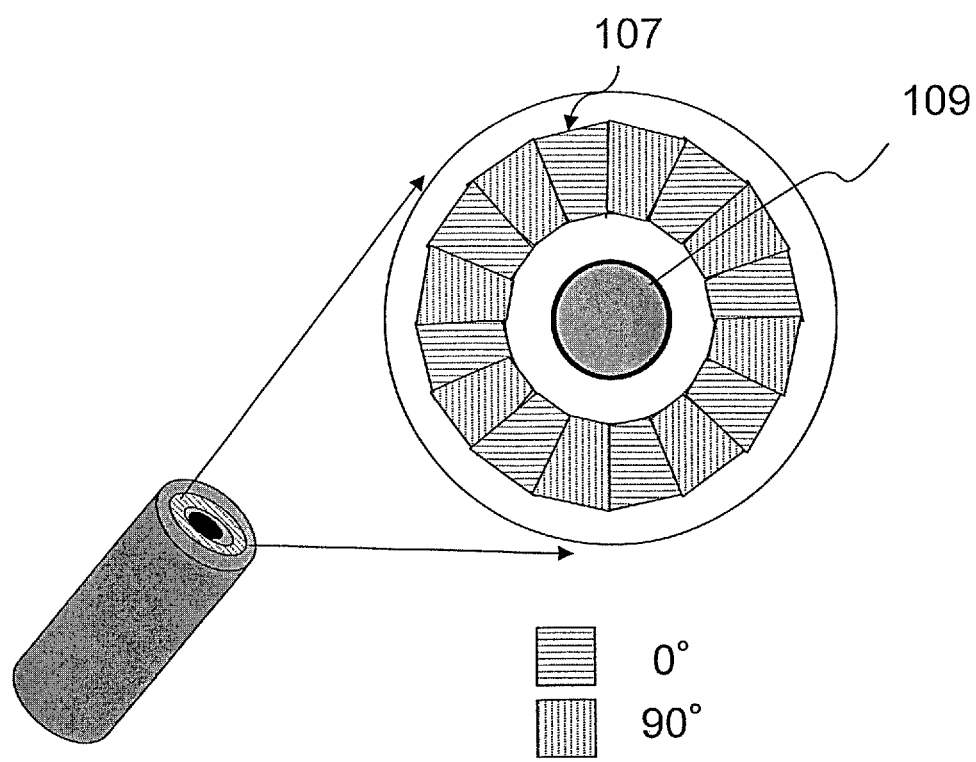
FIG. 21 illustrates the tip portion of an endoscope and a spinning polarized illuminating light source according to the second embodiment of the present disclosure.

In this embodiment, a number of (e.g., sixteen in this example) emission ports, through which an illuminating light beam, of which the polarization plane defines 0 degrees (i.e., P-polarized), and an illuminating light beam, of which the polarization plane defines 90 degrees (i.e., S-polarized), are emitted alternately, are arranged at the tip of the endoscope as shown in FIG. 21, for example. In this example, by lighting one of the two sets of LEDs, each consisting of non-adjacent eight LEDs of the same type, selectively and alternately, a polarized illuminating source which emits P- and S-polarized light beams alternately is realized.

Figure 22:
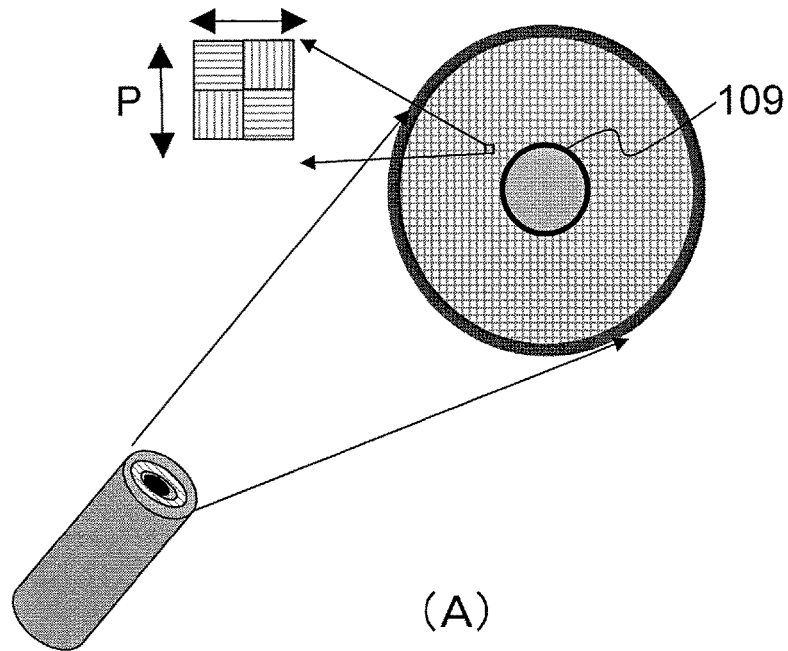
FIG. 22 illustrates another configuration for a rotating polarized illuminating light source according to the second embodiment of the present disclosure.
Figure 22:
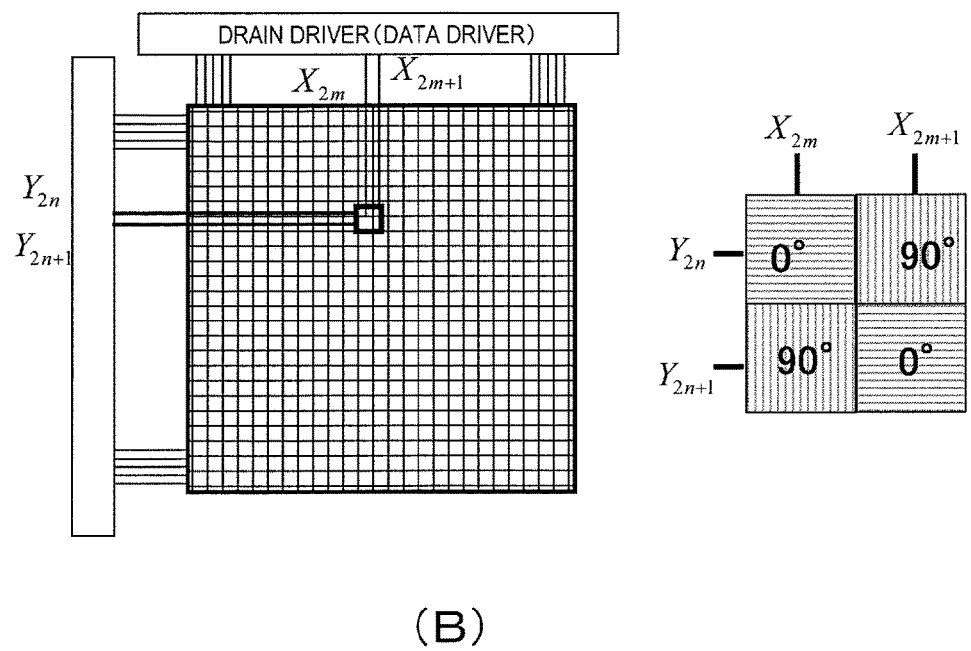

Portion (A) of FIG. 22 illustrates another exemplary spinning polarized illuminating light source. In this example, by providing a far larger number of sufficiently small illuminating pixel units to be sequentially turned ON, the variation in the position of the light source to be lit can be limited to within one pixel at the image sensor end. Portion (B) of FIG. 22 illustrates an overall configuration for such a plane illuminating light source. As shown in portion (A) of FIG. 22, a data driver for controlling the sequential lighting is arranged along each of the X and Y axes of the plane illuminating light source, and the pixels addressed on the X and Y axes are all turned ON simultaneously. For example, if all even-numbered pixels ($X_{2m}$ and $Y_{2m}$) on the X and Y axes are turned ON simultaneously, then an illuminating light beam, of which the polarization plane defines zero degrees, will be emitted. And by appropriately combining the even and odd numbers in the X- and Y-axis data drivers, an illuminating light beam, of which the polarization transmission plane defines 0 degrees (P), and an illuminating light beam, of which the polarization transmission plane defines 90 degrees (S), are obtained.

One of the advantages achieved by using such a plane illuminating light source is that only the polarization state of the illuminating light can be changed with the overall illuminance and light distribution state unchanged. By using a plane light source as the illuminating light source, the degree of uniformity of the illuminating light can be increased. As a result, the very high intensity of the light that has been specular-reflected from the surface mucosa of an organ can be lowered and the object can be shot just as intended.

Figure 23:
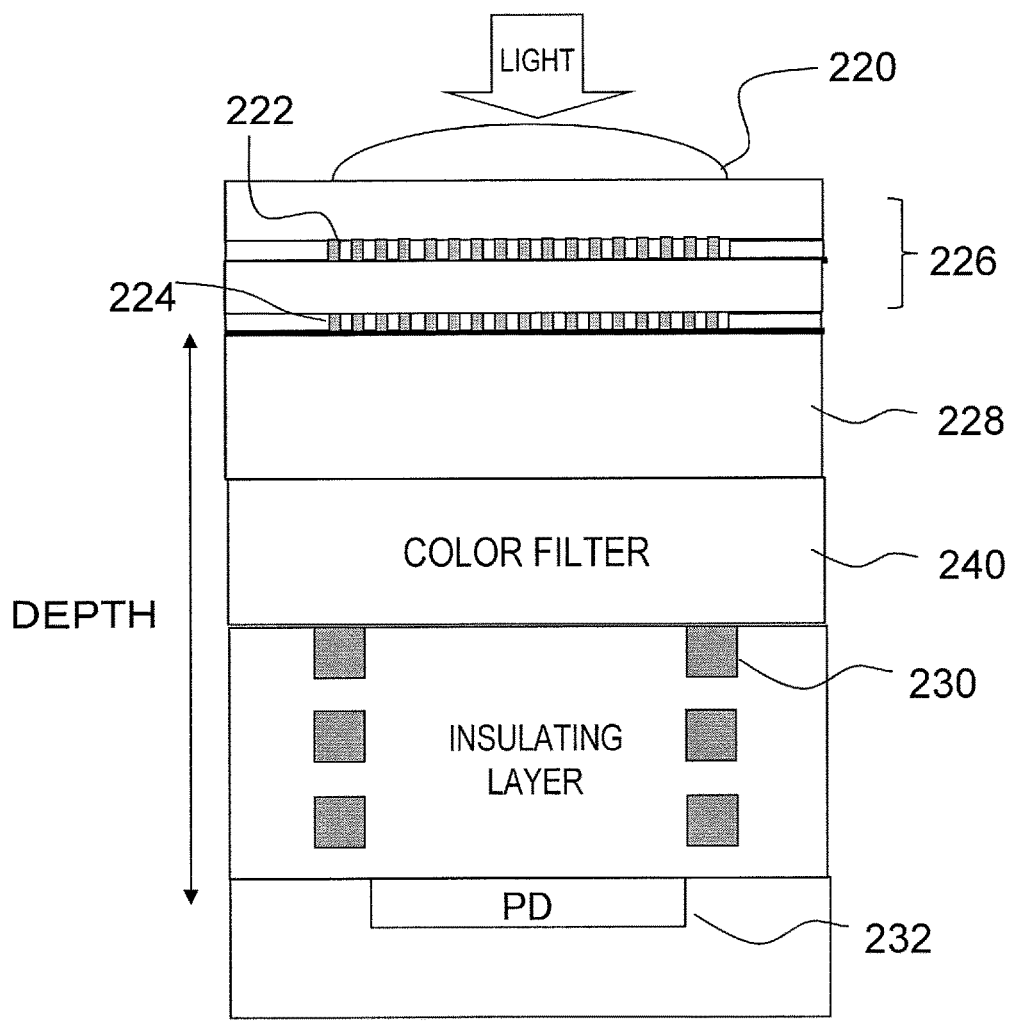
FIG. 23 illustrates a cross-sectional structure of a color polarization image sensor according to the second embodiment of the present disclosure.

FIG. 23 illustrates an exemplary cross-sectional structure for a color polarization image sensor 119 for use in this embodiment. In this color polarization image sensor 119, a color filter 240 is inserted between the wire grid layer 224 and the PD (photodiode) 232, which is a difference from the monochrome broadband polarization image sensor 115 shown in FIG. 10. This color filter 240 may be made of either an organic substance or a photonic crystal or a metal. When viewed in the direction in which the incoming light travels from the light source toward the PD 232, there are six different orders in which the micro lens 220, the first wire grid layer 222, the second wire grid layer 224, and the color filter 240 can be arranged and which have respectively different advantages. In this example, the distance DEPTH from the wire grid 224 to the PD 232 increases by the insertion of the color filter 240 and is typically in the range of 4 to 6 μm.

For example, in the configuration shown in FIG. 23 in which the micro lens 220, the first wire grid layer 222, the second wire grid layer 224, and the color filter 240 are stacked in this order from the top toward the bottom, the micro lens 220 forms the uppermost layer, and therefore, incoming light can be easily made incident perpendicularly to the wire grids.

Figure 24:
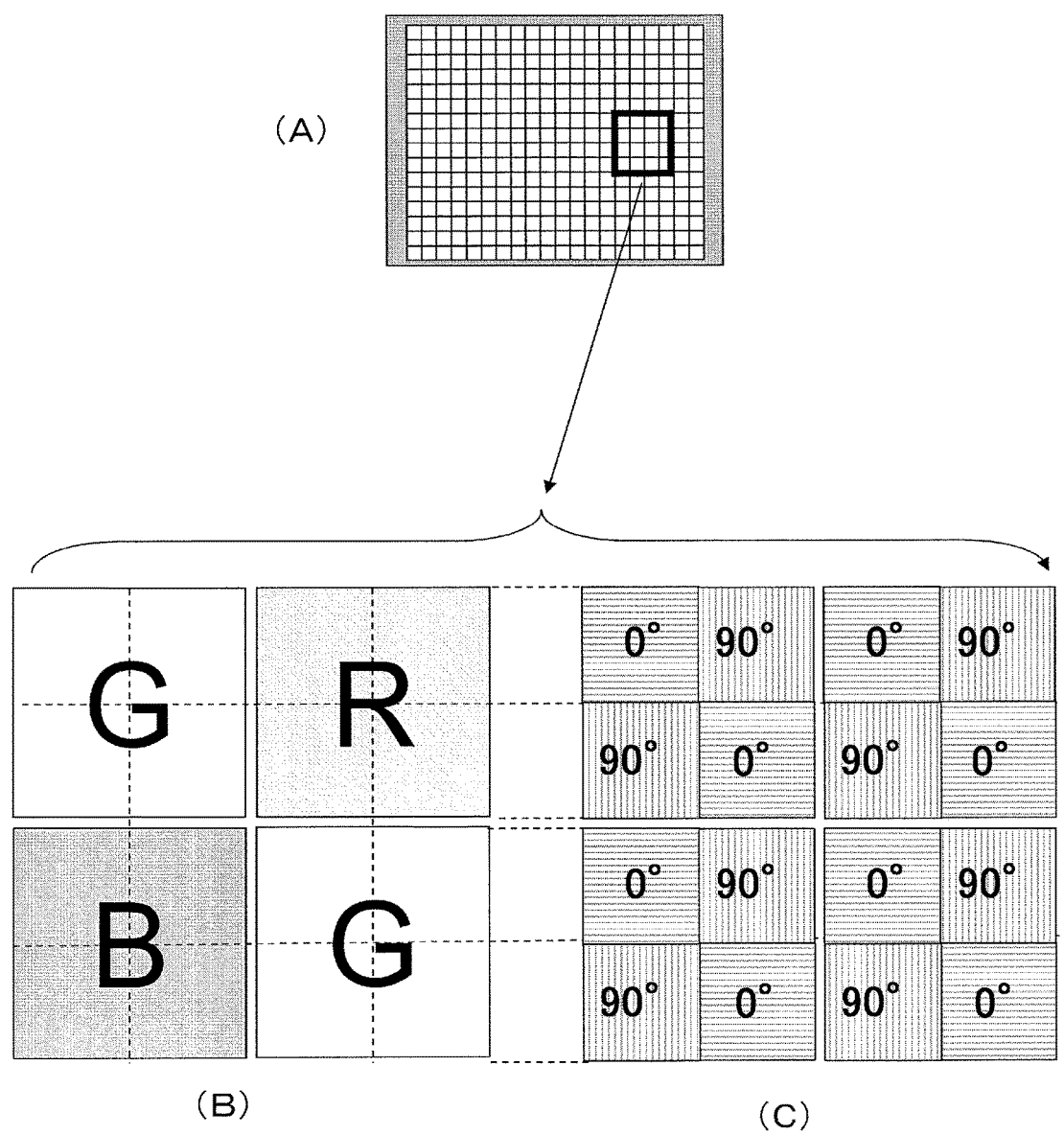
FIG. 24 illustrates planar arrangements of a color mosaic and a polarization mosaic according to the second embodiment of the present disclosure.

FIG. 24 illustrates a planar structure for the color polarization image sensor 119 shown in FIG. 23. Specifically, portion (A) of FIG. 24 illustrates the same planar structure as the single panel color image sensor. In the exemplary configuration shown in portion (A) of FIG. 24, if the 4×4 pixel region is expanded and when viewed from right over the image sensor 119, the color mosaic structure shown in portion (B) of FIG. 24 and the polarization mosaic structure shown in portion (C) of FIG. 24 are laid one upon the other on a pixel-by-pixel basis.

Portion (B) of FIG. 24 illustrates an exemplary color mosaic filter. That is to say, the color mosaic filter that can be used in an embodiment of the present disclosure does not have to be the one shown in portion (B) of FIG. 24. For example, the color mosaic filter does not have to have a Bayer mosaic arrangement but may also have any other mosaic structure. In this example, a filter in a single color included in the color mosaic covers the region in which four pixels (i.e., four photodiodes) are arranged in two columns and two rows. The 2×2 pixel region is associated with the four kinds of polarization mosaic regions shown in portion (C) of FIG. 24. That is to say, even though the resolution (or the number of pixels) of this image sensor is just a quarter (i.e., ½×½) of the original one when considered on a subpixel basis, the artifacts to be generated as a result of polarized light processing can be reduced by carrying out the polarized light processing within a single pixel.

Figure 25:
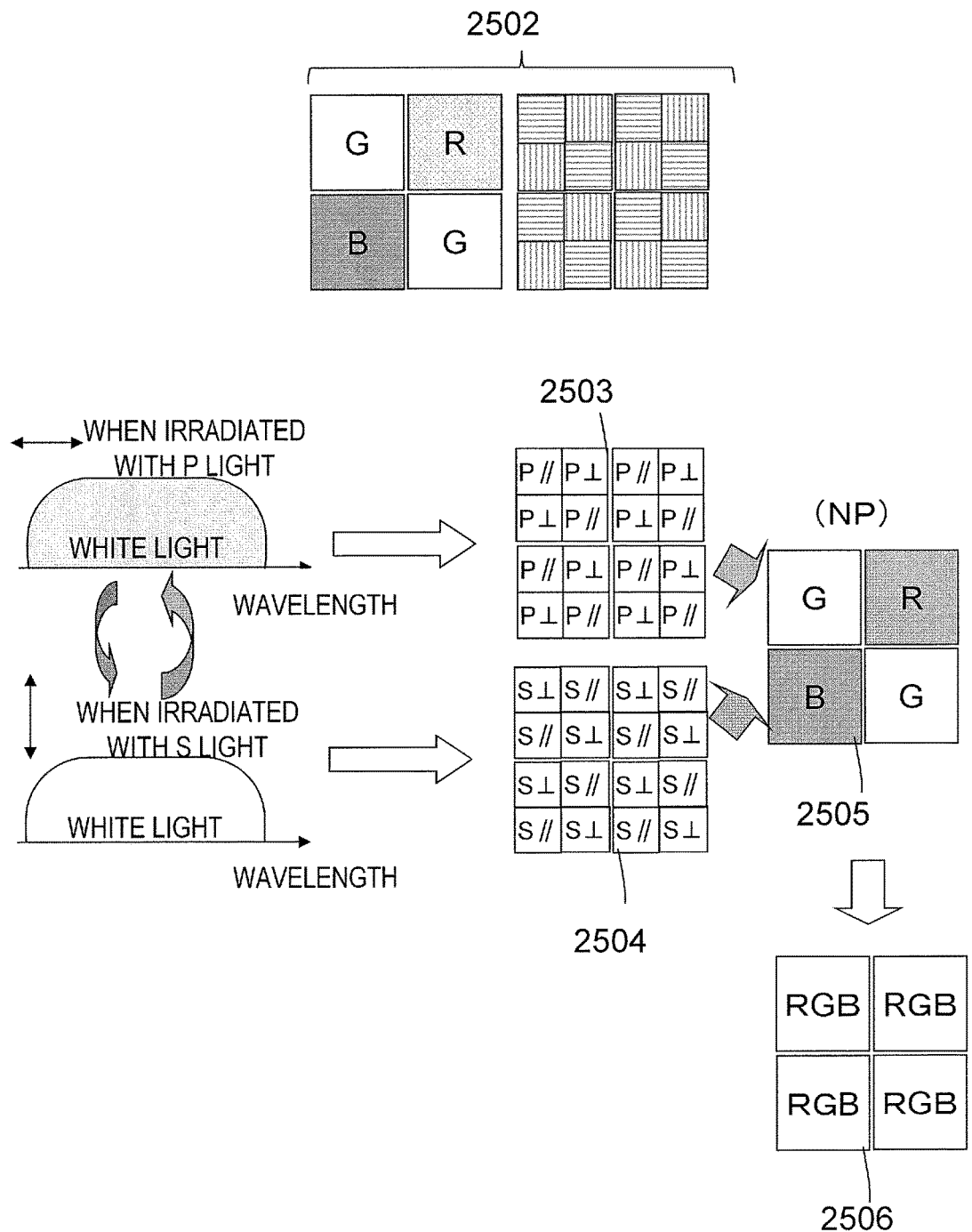
FIG. 25 illustrates how the polarization mosaic processing section 202 operates in the normal image capturing mode according to the second embodiment of the present disclosure.

Next, it will be described with reference to FIG. 25 how the image processing apparatus of this embodiment operates in the normal image capturing mode. The object is alternately irradiated with a white P-polarized light beam and a white S-polarized light beam. And every time the object is irradiated with a polarized light beam, a polarization color mosaic image is obtained. Specifically, when the object is irradiated with a P-polarized light beam, a polarization pixel pattern 2503 is obtained by the polarization mosaic 2502. On the other hand, when the object is irradiated with an S-polarized light beam, a polarization pixel pattern 2504 is obtained by the polarization mosaic 2502. In FIG. 25, P// indicates pixels in the parallel-Nicols state when irradiated with a P-polarized light beam, and P⊥ indicates pixels in the crossed-Nicols state when irradiated with a P-polarized light beam. Likewise, S// indicates pixels in the parallel-Nicols state when irradiated with an S-polarized light beam, and S⊥ indicates pixels in the crossed-Nicols state when irradiated with an S-polarized light beam. The polarization mosaic processing section 202 adds together the images with these polarization pixel patterns 2503 and 2504 and calculates their average on a pixel-by-pixel basis. If that adding and averaging processing is carried out on each color pixel based on the polarization pixel patterns 2503 and 2504, the values of pixels in the parallel-Nicols state and the values of pixels in the crossed-Nicols state can be uniformly mixed together as represented by the following Equation (4):

$$(NP)=(P//+P\perp+S//+S\perp)/4 \qquad (4)$$

As a result V of this adding and averaging processing, a non-polarization (NP) color mosaic image 2505, of which the resolution is just a quarter (=½×½) of the original one, is obtained. The processing of generating a full-color image based on this non-polarization color mosaic image 2505 may be carried out by ordinary color mosaic interpolation.

Figure 26:
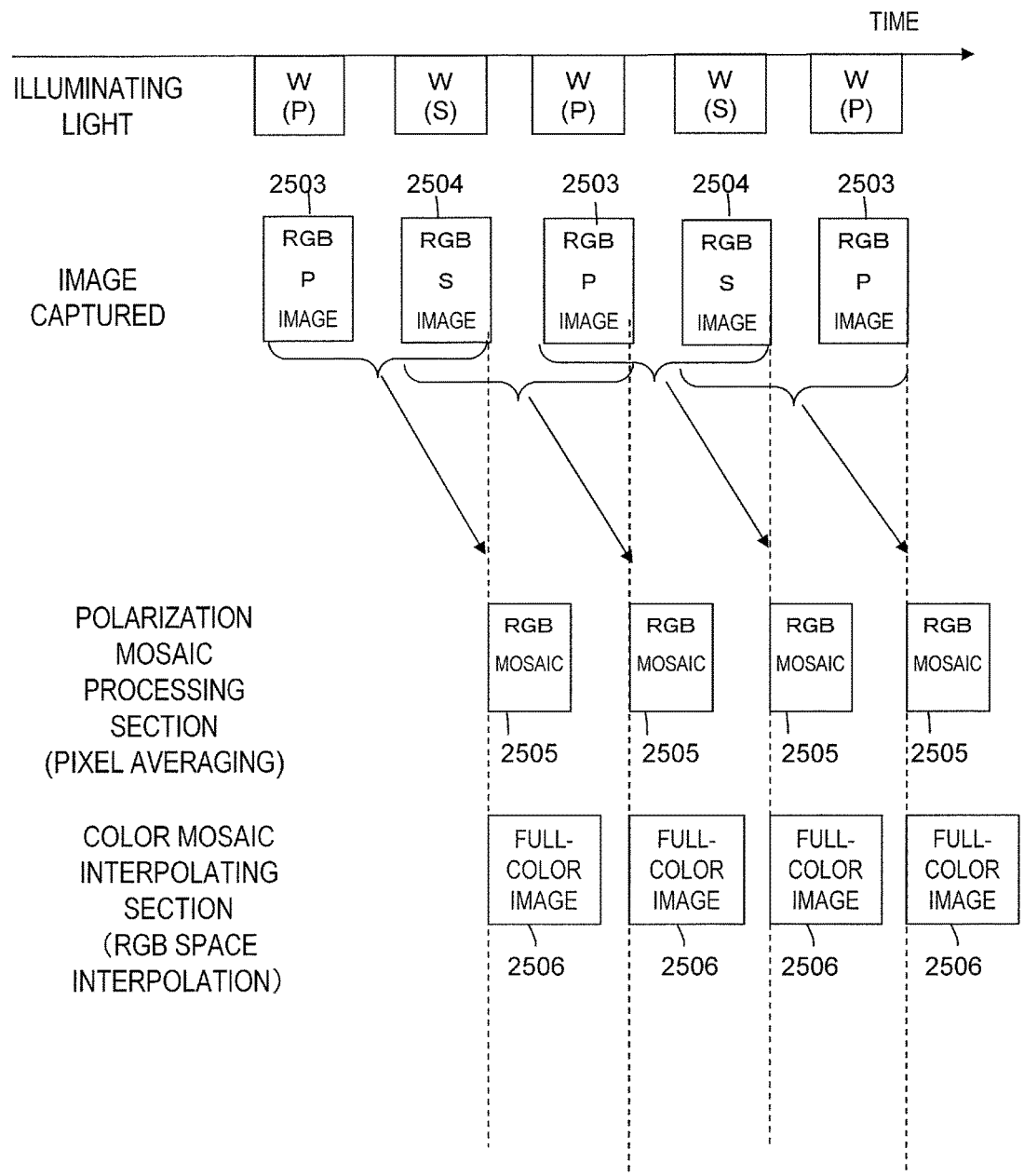
FIG. 26 shows a timing chart showing how the apparatus according to the second embodiment of the present disclosure operates in the normal image capturing mode.

FIG. 26 is a timing chart showing the sequence of these operations. Specifically, the operation of emitting illuminating light beams, the image capturing operation, and the color component images processed by the polarization mosaic processing section 202 are shown in this order from top to bottom of FIG. 26. The respective operations are performed at these timings under the control of the synchronizer 112. When the object is alternately irradiated with a P-polarized light beam and an S-polarized light beam, their associated polarization pixel patterns 2503 and 2504 are captured. The polarization mosaic processing section 202 carries out the adding and averaging processing on the polarization pixel patterns 2503 and 2504 shown in FIG. 25, thereby obtaining a non-polarization color mosaic image 2505. Next, by performing color mosaic interpolation processing, an RGB full-color image is obtained. Consequently, by irradiating the object with a P-polarized illuminating light beam and an S-polarized illuminating light beam, a single RGB full-color image can be obtained. Actually, by performing temporally adjacent P-polarized illuminating light processing and S-polarized illuminating light processing continuously as shown in FIG. 26, images can be generated as a moving picture at regular interval of one frame period without causing a delay.

Figure 27:
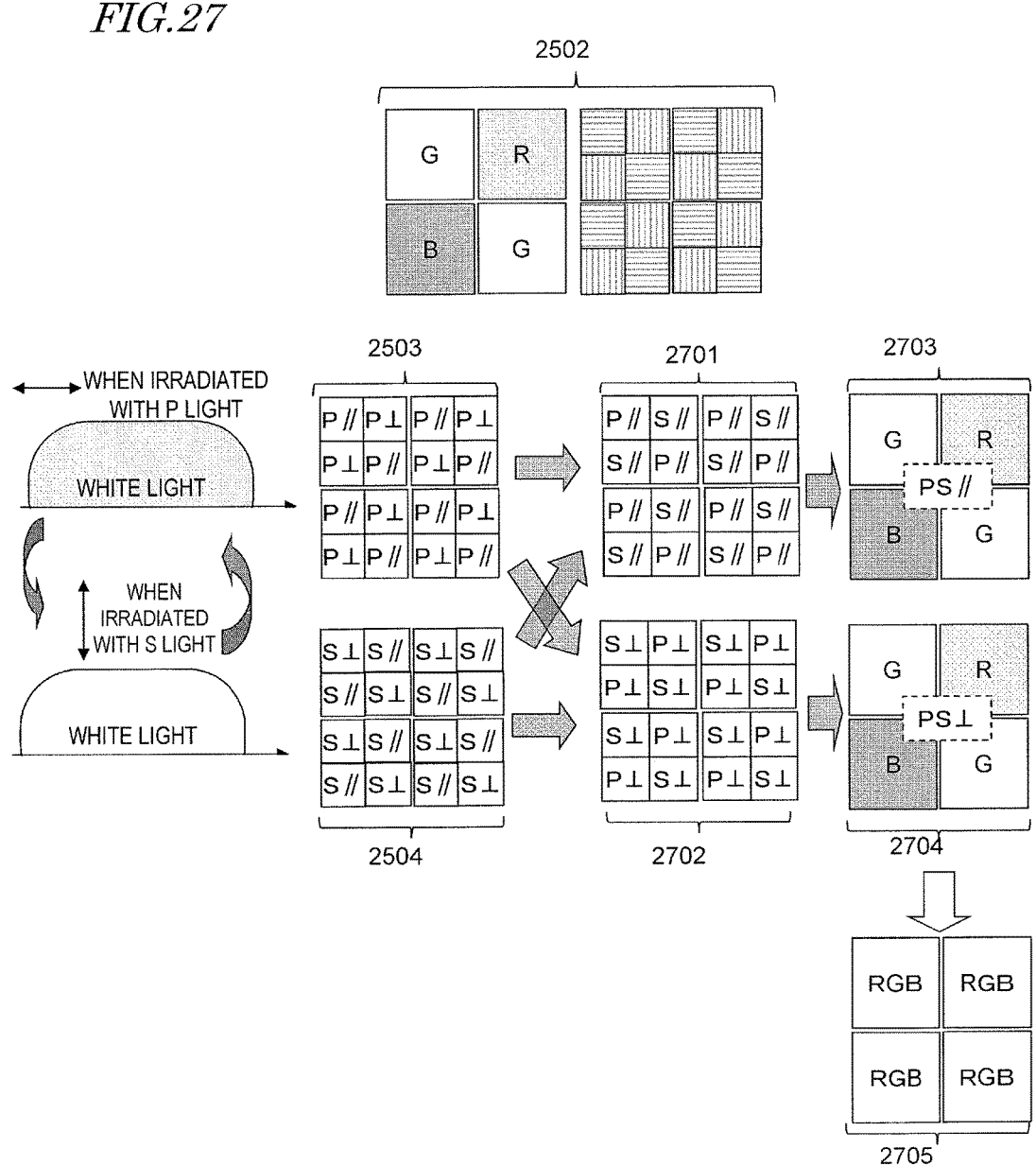
FIG. 27 illustrates how the polarization mosaic processing section 202 operates in the polarization image capturing mode according to the second embodiment of the present disclosure.

FIG. 27 illustrates how the image processing apparatus of this embodiment operates in the polarization image capturing mode, in which the object is alternately irradiated with a P-polarized light beam and an S-polarized light beam and a polarization color mosaic image is obtained every time the object is irradiated with such a polarized light beam. The polarization pixel patterns 2503 and 2504 obtained in this case are the same as the polarization pixel patterns 2503 and 2504 shown in FIG. 25. Using both of these polarization pixel patterns 2503 and 2504, the polarization mosaic processing section 202 selects and integrates together P// and S// and P⊥ and S⊥ for each pixel in question. In this manner, a P- and S-polarized mixed parallel Nicols image 2701 and a P- and S-polarized mixed crossed Nicols image 2702 are generated separately. Then, four pixels within the same color pixel are added together and have their average calculated as represented by the following Equations (5):

$$(PS//)=(P//+S//+P//+S//)/4$$

$$(PS\perp)=(P\perp+S\perp+P\perp+S\perp)/4 \qquad (5)$$

As a result of this processing, color mosaic images 2703 and 2704, of which the resolution is just a quarter (=½×½) of the original one, are obtained. The same color pixels within the color mosaic images 2703 and 2704 form a parallel Nicols image PS// and a crossed Nicols image PS⊥, each of which is irradiated with a P-polarized illuminating light beam and an S-polarized illuminating light beam uniformly. A color mosaic interpolation is carried out on the crossed Nicols image PS⊥, thereby generating a full-color crossed Nicols image, which is subjected to the same processing as what has already been described with respect to the first embodiment by the depressed area detecting section 204 and the image synthesizing section 206.

Figure 28:
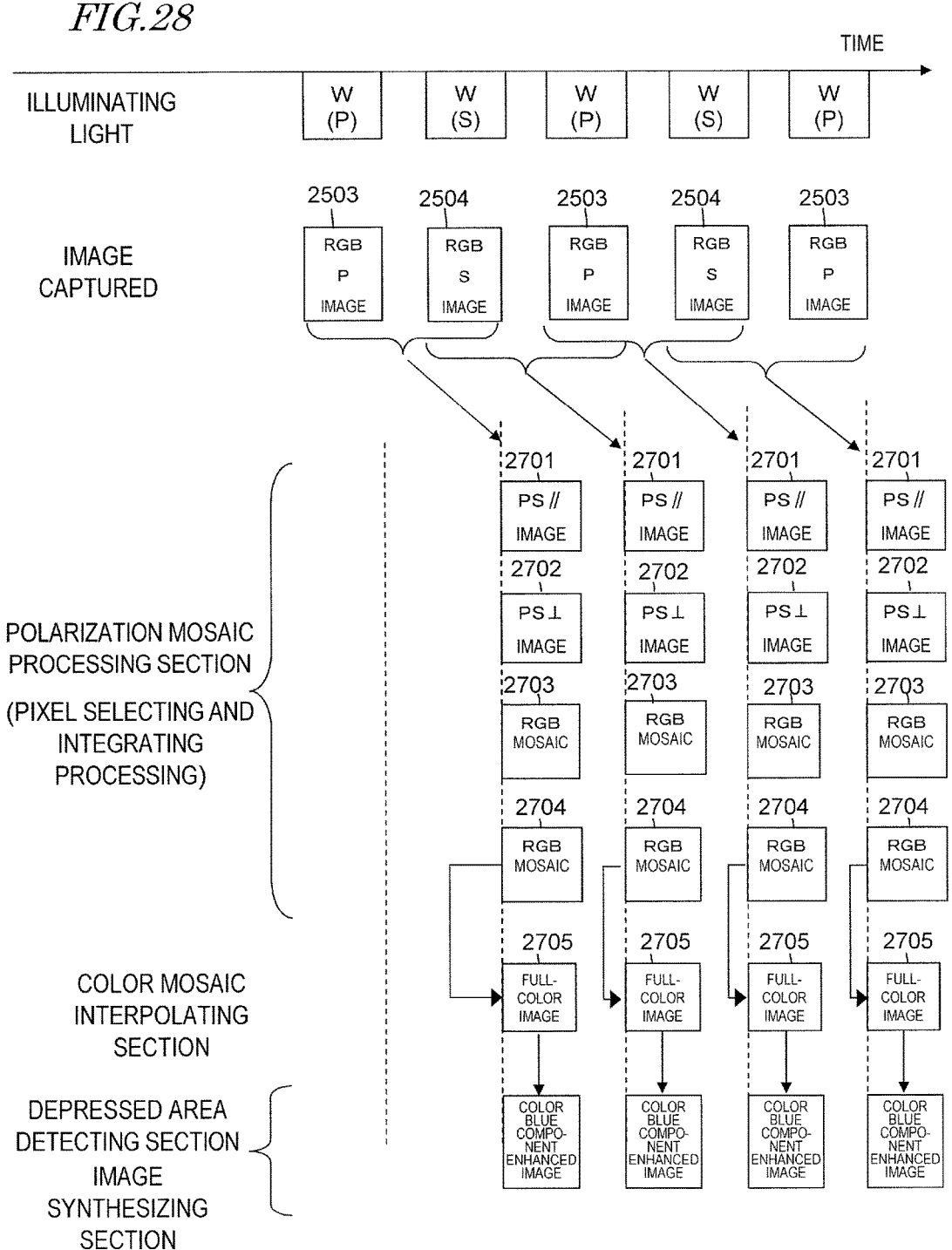
FIG. 28 shows a timing chart showing how the apparatus according to the second embodiment of the present disclosure operates in the polarization image capturing mode.

FIG. 28 is a timing chart showing the sequence of these operations. Specifically, the operation of emitting illuminating light beams, the image capturing operation, and the color images processed by the polarization mosaic processing section 202, the color mosaic interpolating section 208, the depressed area detecting section 204, and the image synthesizing section 206 are shown in this order from top to bottom of FIG. 28. The operation of emitting illuminating light beams and the image capturing operation are the same as in the normal image capturing mode timing chart shown in FIG. 26. The polarization mosaic processing section 202 operates so as to generate a P- and S-polarized illuminating light beam mixed parallel Nicols image 2701 and a P- and S-polarized illuminating light beam mixed crossed Nicols image 2702 by using an image captured under a P-polarized illuminating light beam and an image captured under an S-polarized illuminating light beam on a frame-by-frame basis. That is to say, two different kinds of polarization pixel patterns 2701 and 2702 are generated on a frame-by-frame basis. In addition, color mosaic images 2703 and 2704 are also generated simultaneously by adding those polarization pixel patterns together and calculating their average. The resolution of the color mosaic images 2703 and 2704 has decreased to a quarter (=½×½) of the original one. As already described for the first embodiment with reference to FIG. 16, the crossed Nicols image 2704 is presented every frame as a moving picture on the display section 114 as a full-color image, of which the color blue component has been enhanced at the depressions of the surface texture by the depressed area detecting section 204 and the image synthesizing section 206.

(Modified Example 1 of Embodiment 2)

Figure 29:
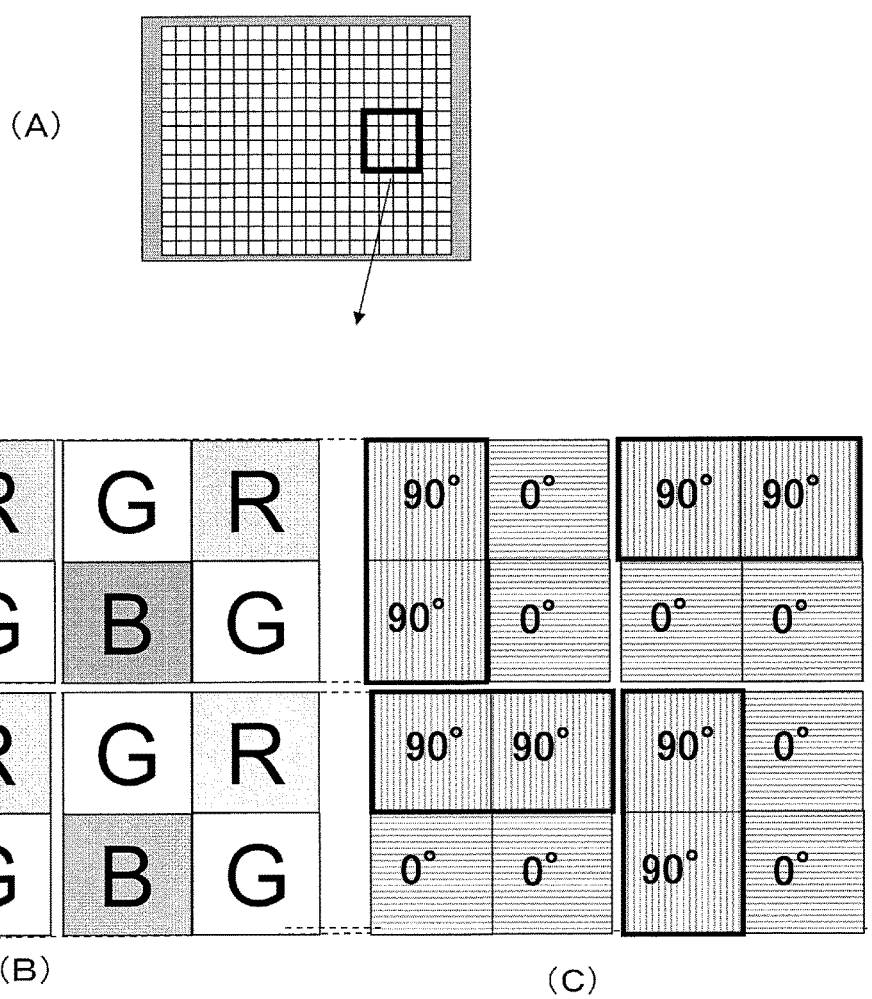
FIG. 29 illustrates planar arrangements of a color mosaic and a polarization mosaic according to a first modified example of the second embodiment of the present disclosure.

FIG. 29 illustrates a first modified example of the second embodiment of the present disclosure. Portion (A) of FIG. 29 illustrates a planar structure of the color polarization image sensor 119 of the second embodiment shown in FIG. 23. The planar structure shown in Portion (A) of FIG. 29 is the same as that of a color single-panel image sensor. Portion (B) of FIG. 29 illustrates an exemplary arrangement of 4×4 color filters in the color mosaic. And portion (C) of FIG. 29 illustrates an exemplary arrangement of eight polarizers in a polarization mosaic. These color and polarization mosaics are stacked one upon the other to cover 4×4 pixels (or PDs (photodiodes)).

In this embodiment, color filters in two colors of the color mosaic are associated with a single rectangular polarizer. In the other respects, this configuration is the same as that of the second embodiment.

The pixels over which polarizers indicated with an angle of 0 degrees in portion (C) of FIG. 29 are located are pixels which transmit a P-polarized light beam, and the pixels over which polarizers indicated with an angle of 90 degrees are located are pixels which transmit an S-polarized light beam. In this case, the 0 degree polarizers and the 90 degree polarizers do not form a checkerboard pattern. That is to say, this polarization mosaic is formed so that the same polarized light beam is incident on two pixels which are vertically or horizontally adjacent to each other within the image capturing plane. This arrangement is adopted so that a degree polarizer and a 90 degree polarizer are always allocated to two G pixels which form parts of the RGB pixels. In such a configuration, the 0 degree polarizer is allocated to the two pixels of RG and the two pixels of BG, and the 90 degree polarizer is allocated to the two pixels of GB and the two pixels of GR.

Figure 30:
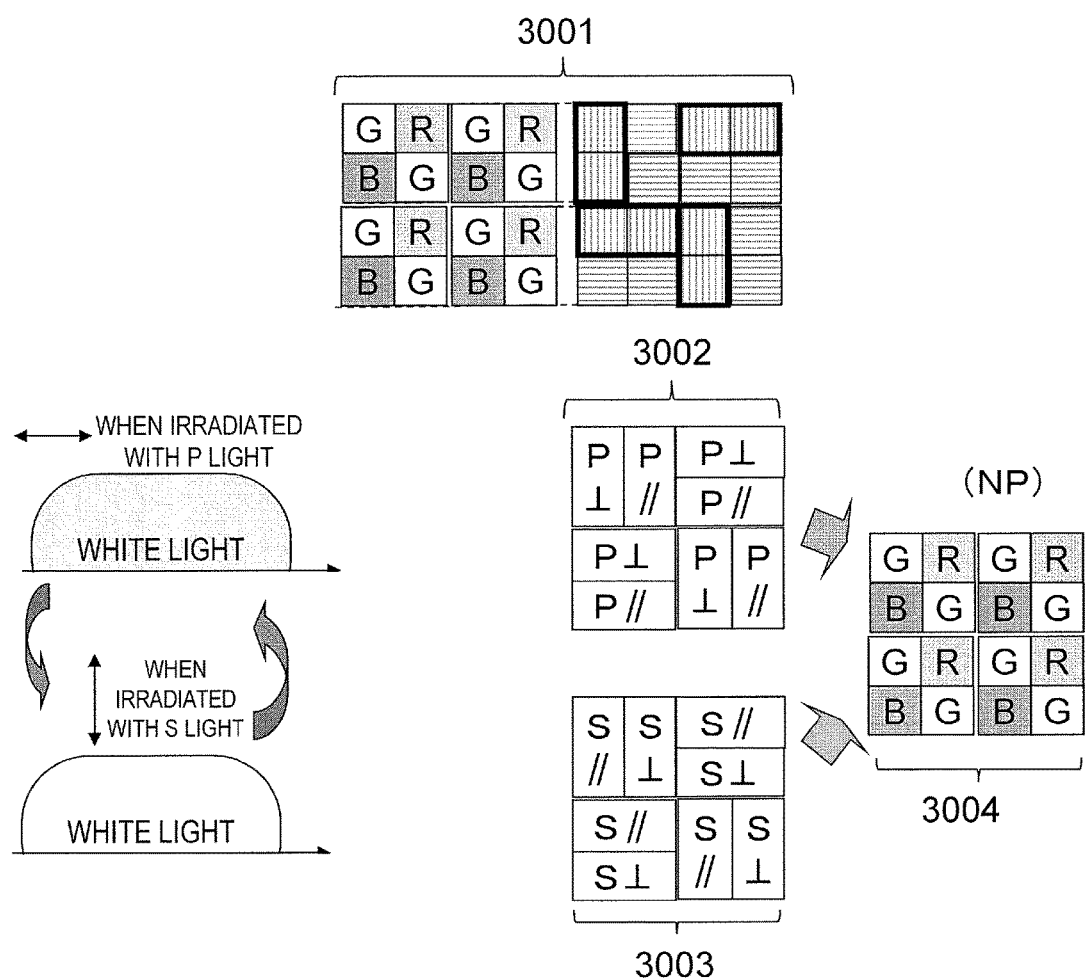
FIG. 30 illustrates how the polarization mosaic processing section 202 operates in the normal image capturing mode according to the first modified example of the second embodiment of the present disclosure.

FIG. 30 illustrates how the image processing apparatus of this embodiment operates in the normal image capturing mode, in which the object is irradiated with a white P-polarized light beam and a white S-polarized light beam alternately, an image is captured every time the object is irradiated with such a polarized light beam, and a polarization color mosaic image is obtained as a result. Since the polarization mosaic has the arrangement 3001, a polarization pixel pattern 3002 is obtained when the object is irradiated with a P-polarized light beam and a polarization pixel pattern 3003 is obtained when the object is irradiated with an S-polarized light beam. In FIG. 30, P// and P⊥ indicate pixels in the parallel Nicols state and pixels in the crossed Nicols state when the object is irradiated with a P-polarized light beam. Likewise, S// and S⊥ indicate pixels in the parallel Nicols state and pixels in the crossed Nicols state when the object is irradiated with an S-polarized light beam. The polarization mosaic processing section 202 adds together these polarization pixel patterns 3002 and 3003 and calculates their average on a pixel-by-pixel basis. In this adding and averaging processing, the pixels in the parallel Nicols state and the pixels in the crossed Nicols state would be mixed together uniformly in the following manner.

In that case, the resultant color mosaic image 3004 will include pixels in the crossed Nicols state as a combination of color pixels and pixels in the parallel Nicols state as a different combination of color pixels. However, this is not a serious problem. The reason is that as the illuminating angle and the image capturing angle with respect to the object are almost equal to each other in an endoscope, it is rare if any that a non-polarized illuminating light beam is reflected and significantly polarized, and there is almost no color difference when observed normally (except a situation where there is a micro-geometric surface).

$$(NP)=(P\perp+S//)/2$$

$$(NP)=(P//+S\perp)/2 \qquad (6)$$

As a result V of this adding and averaging processing, a non-polarization color mosaic image 3004 is obtained. In this case, the resolution does not decrease unlike the second embodiment. The processing of generating a full-color image based on this non-polarization color mosaic image 3004 may be carried out by normal color mosaic interpolation.

Figure 31:
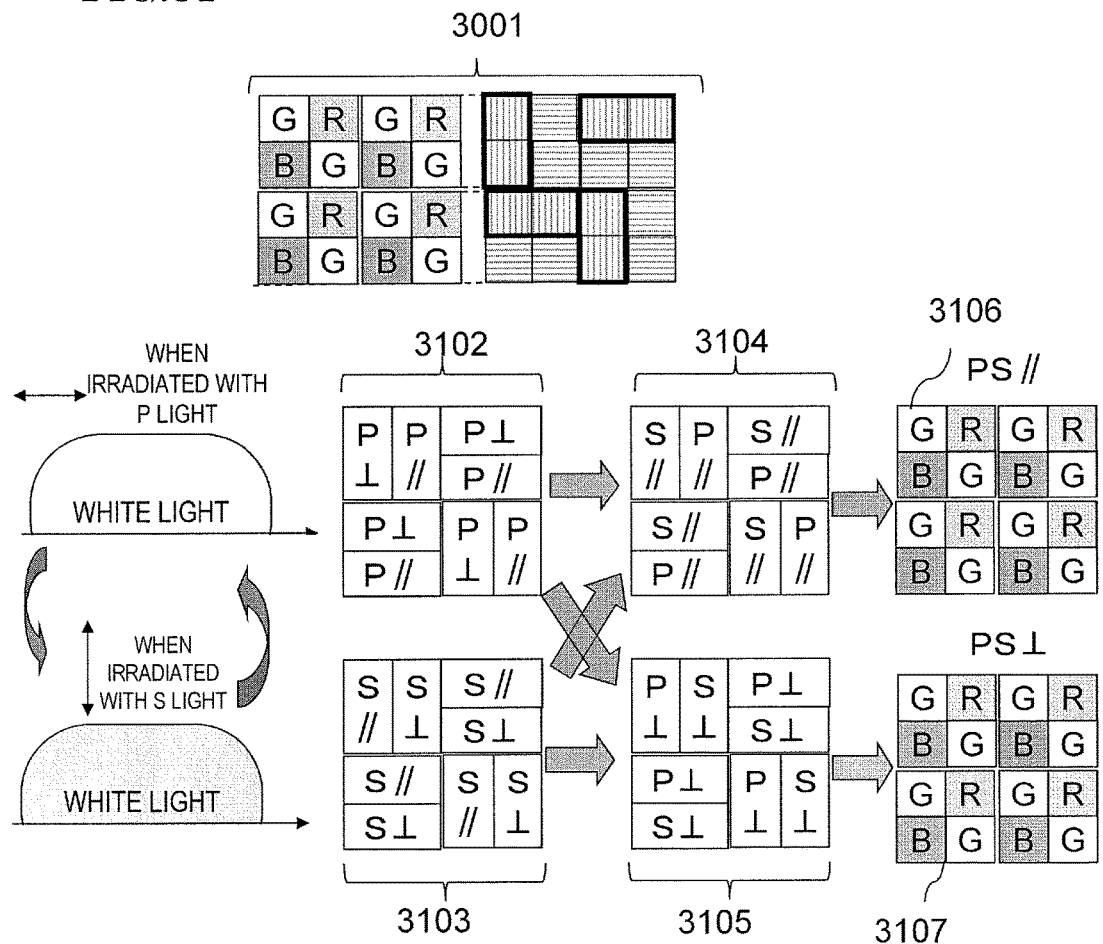
FIG. 31 illustrates how the polarization mosaic processing section 202 operates in the polarization image capturing mode according to the first modified example of the second embodiment of the present disclosure.

FIG. 31 illustrates how the image processing apparatus of this embodiment operates in the polarization image capturing mode, in which the object is alternately irradiated with a P-polarized light beam and an S-polarized light beam, and images are captured and polarization pixel patterns 3102 and 3103 are obtained every time the object is irradiated with such a polarized light beam. Using both of these polarization pixel patterns 3102 and 3103, the polarization mosaic processing section 202 collects and fills with P// and S// and P⊥ and S⊥ for each pixel in question. In this manner, a P- and S-polarized mixed parallel Nicols image 3104 and a P- and S-polarized mixed crossed Nicols image 3105 are generated separately. The polarization images obtained as a result of this processing are color mosaic images 3106 and 3107, which are respectively a parallel Nicols image PS// and a crossed Nicols image PS⊥, each of which is obtained by irradiating the object with a P-polarized illuminating light beam and an S-polarized illuminating light beam uniformly. A color mosaic interpolation is carried out on the crossed Nicols image PS⊥, thereby generating a full-color crossed Nicols image, which is subjected to the same processing by the depressed area detecting section 204 and the image synthesizing section 206 as what has already been described for the first embodiment. It should be noted that the timing chart for this embodiment is the same as the timing chart for the second embodiment.

(Modified Example 2 of Embodiment 2)

Figure 32:
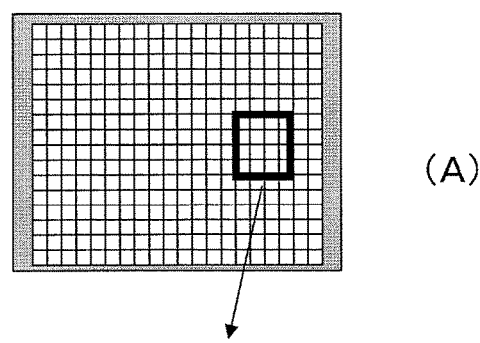
FIG. 32 illustrates planar arrangements of a color mosaic and a polarization mosaic according to a second modified example of the second embodiment of the present disclosure.
Figure 32:
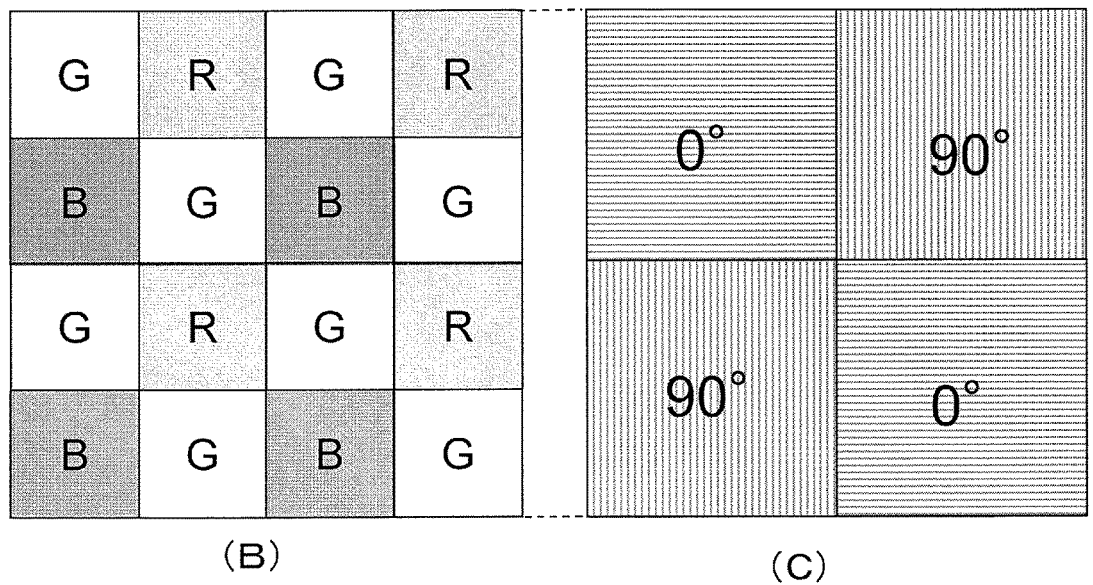

FIG. 32 illustrates a second modified example of the second embodiment of the present disclosure. Portion (A) of FIG. 32 illustrates a planar structure of the color polarization image sensor 119 shown in FIG. 23. Portion (B) of FIG. 32 illustrates an exemplary arrangement of 4×4 color filters in the color mosaic. And portion (C) of FIG. 32 illustrates an exemplary arrangement of four polarizers in a polarization mosaic. These color and polarization mosaics are stacked one upon the other to cover 4×4 pixels (or PDs (photodiodes)).

In this embodiment, four pixels that form a single unit of the color Bayer mosaic are associated with a single unit of the polarization mosaic. In the other respects, the configuration of this embodiment is the same as that of the second embodiment. The pixels over which polarizers indicated with an angle of 0 degrees in portion (C) of FIG. 32 are located are pixels which transmit a P-polarized light beam, and the pixels over which polarizers indicated with an angle of 90 degrees are located are pixels which transmit an S-polarized light beam. In this case, the 0 degree polarizers and the 90 degree polarizers of the polarization mosaic form a checkerboard pattern, and the same color Bayer mosaic is included in each of those polarizers.

Figure 33:
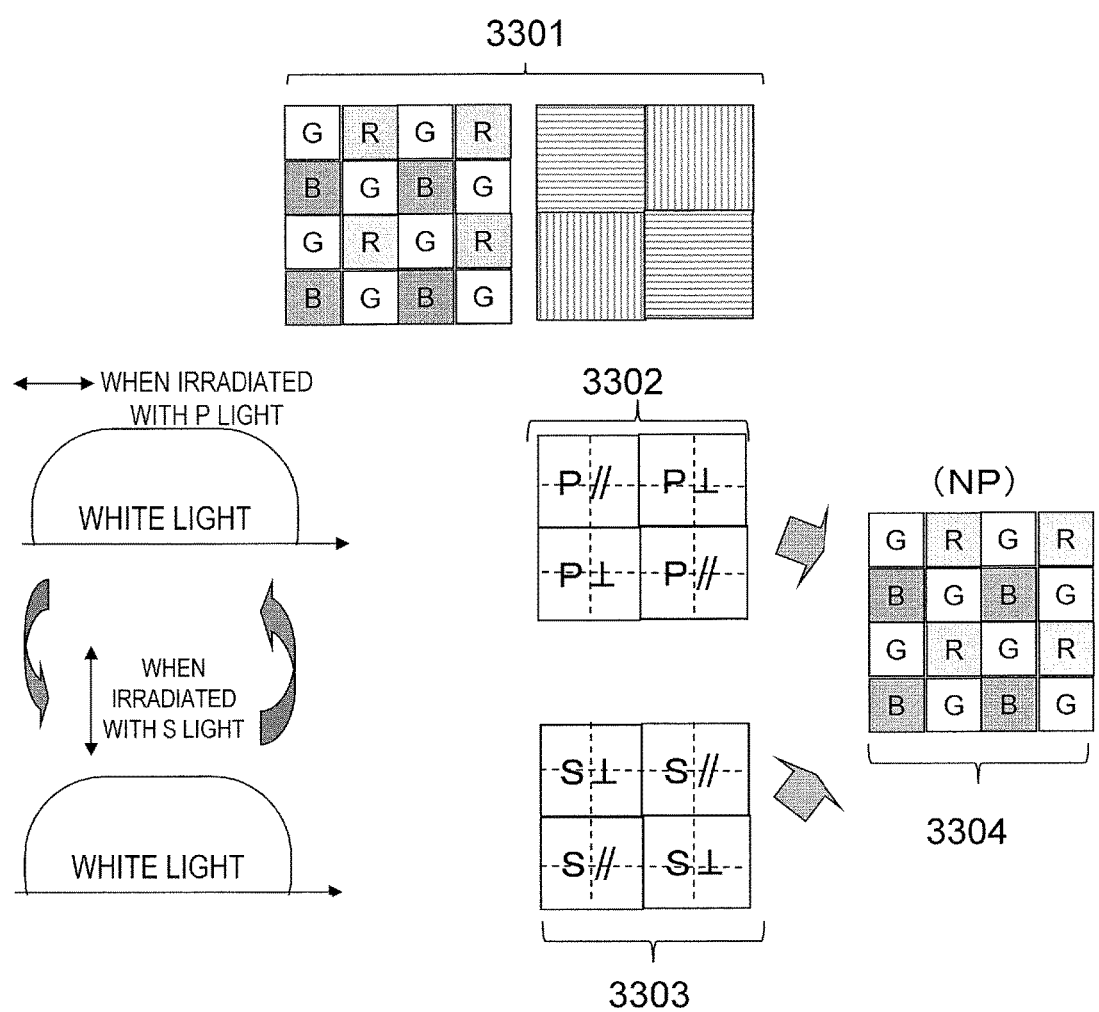
FIG. 33 illustrates how the polarization mosaic processing section 202 operates in the normal image capturing mode according to the second modified example of the second embodiment of the present disclosure.

FIG. 33 illustrates how the image processing apparatus of this embodiment operates in the normal image capturing mode, in which the object is irradiated with a white P-polarized light beam and a white S-polarized light beam alternately, an image is captured every time the object is irradiated with such a polarized light beam, and a polarization color mosaic image is obtained as a result. Since the polarization mosaic has the arrangement 3301, a polarization pixel pattern 3302 is obtained when the object is irradiated with a P-polarized light beam and a polarization pixel pattern 3303 is obtained when the object is irradiated with an S-polarized light beam. In FIG. 33, P//, P⊥, S// and S⊥ have the same meanings as what has already been described. The polarization mosaic processing section 202 adds together the images with these polarization pixel patterns 3302 and 3303 and calculates their average on a pixel-by-pixel basis. In this adding and averaging processing, the pixels in the parallel Nicols state and the pixels in the crossed Nicols state would be mixed together uniformly as represented by Equations (6).

As a result V of this adding and averaging processing, a non-polarization color mosaic image 3304 is obtained. In this case, unlike the second embodiment, the resolution does not decrease, which is a feature of this modified example. The processing of generating a full-color image based on this non-polarization color mosaic image may be carried out by normal color mosaic interpolation.

Figure 34:
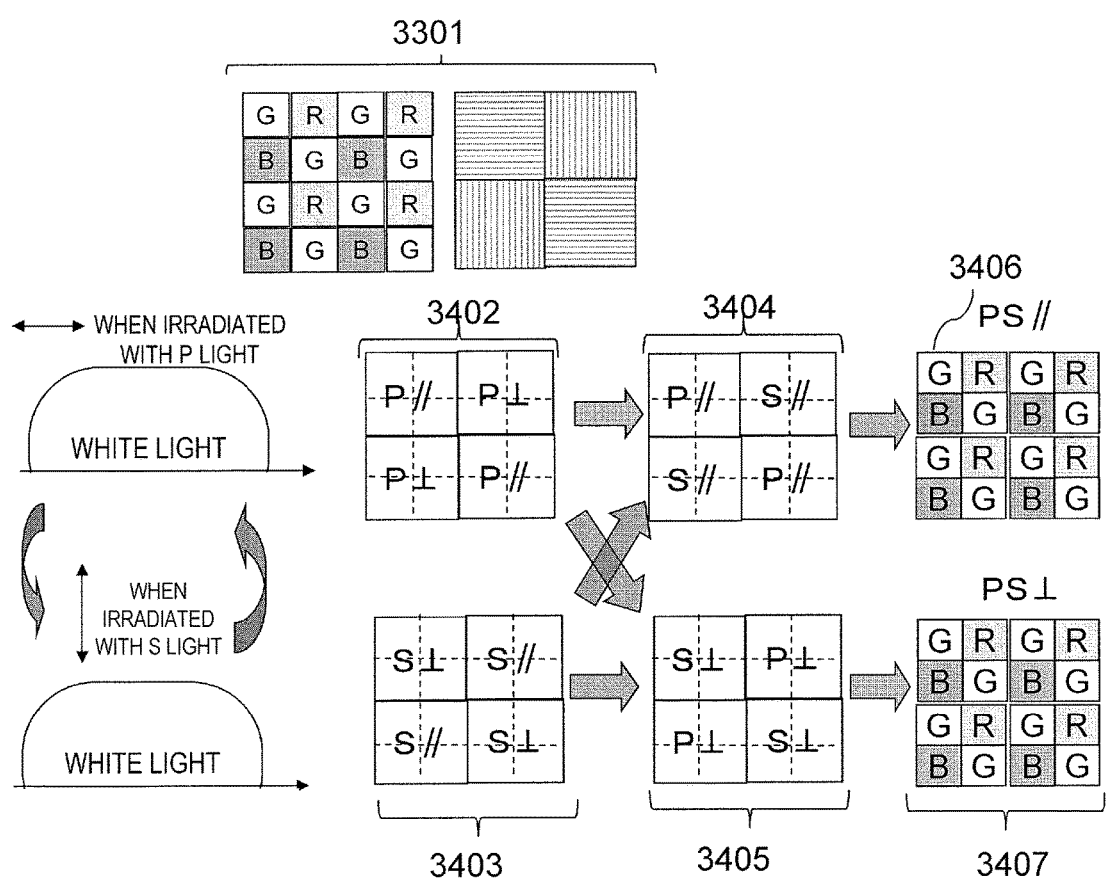
FIG. 34 illustrates how the polarization mosaic processing section 202 operates in the polarization image capturing mode according to the second modified example of the second embodiment of the present disclosure.

FIG. 34 illustrates how the image processing apparatus of this embodiment operates in the polarization image capturing mode, in which the object is alternately irradiated with a P-polarized light beam and an S-polarized light beam and images are captured and polarization pixel patterns 3402 and 3403 are obtained every time the object is irradiated with such a polarized light beam.

Using both of these polarization pixel patterns 3402 and 3403, the polarization mosaic processing section 202 collects and fills with P// and S// and P⊥ and S⊥ for each pixel in question. In this manner, a P- and S-polarized mixed parallel Nicols image 3404 and a P- and S-polarized mixed crossed Nicols image 3405 are generated separately. The polarization images obtained as a result of this processing are color mosaic images 3406 and 3407, which are respectively a parallel Nicols image PS// and a crossed Nicols image PS⊥, each of which is obtained by irradiating the object with a P-polarized illuminating light beam and an S-polarized illuminating light beam uniformly. A color mosaic interpolation is carried out on the crossed Nicols image PS⊥, thereby generating a full-color crossed Nicols image, which is subjected to the same processing by the depressed area detecting section 204 and the image synthesizing section 206 as what has already been described for the first embodiment. It should be noted that the timing chart for this embodiment is the same as the timing chart for the second embodiment.

(Embodiment 3)

Figure 35:
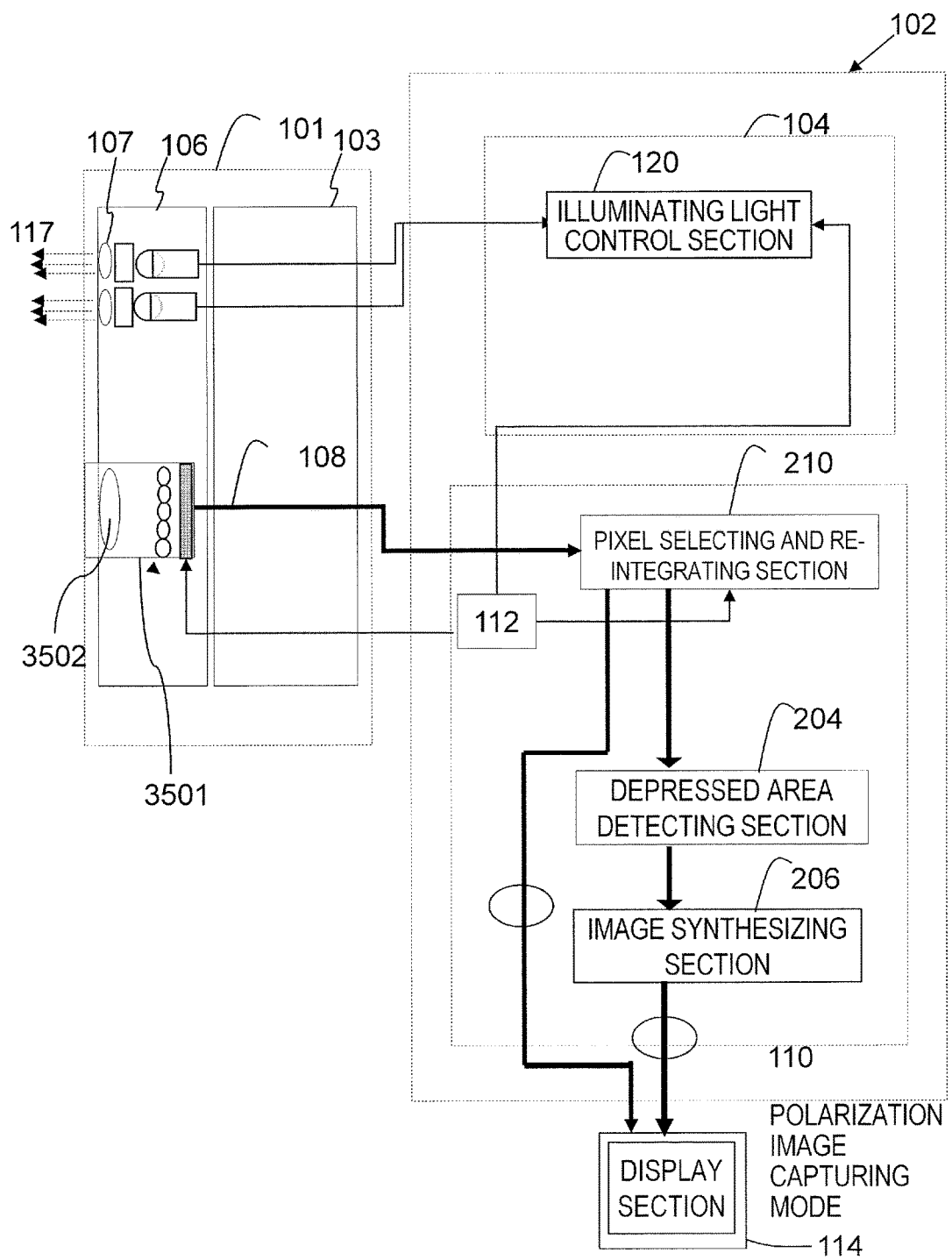
FIG. 35 shows a block diagram illustrating a configuration for a third embodiment of the present disclosure.

FIG. 35 illustrates a configuration for a third embodiment of the present invention. In this embodiment, a color image is captured by a single-panel color image sensor by irradiating the object with white light. Unlike the second embodiment, a polarizer and a color filter are arranged inside the aperture of a lens, a micro lens array type color polarization image capturing section 3501 is provided by arranging a micro lens array on the image capturing plane, and a pixel selecting and re-integrating section 210 is provided in order to perform image processing unique to a micro lens array type element.

Figure 36:
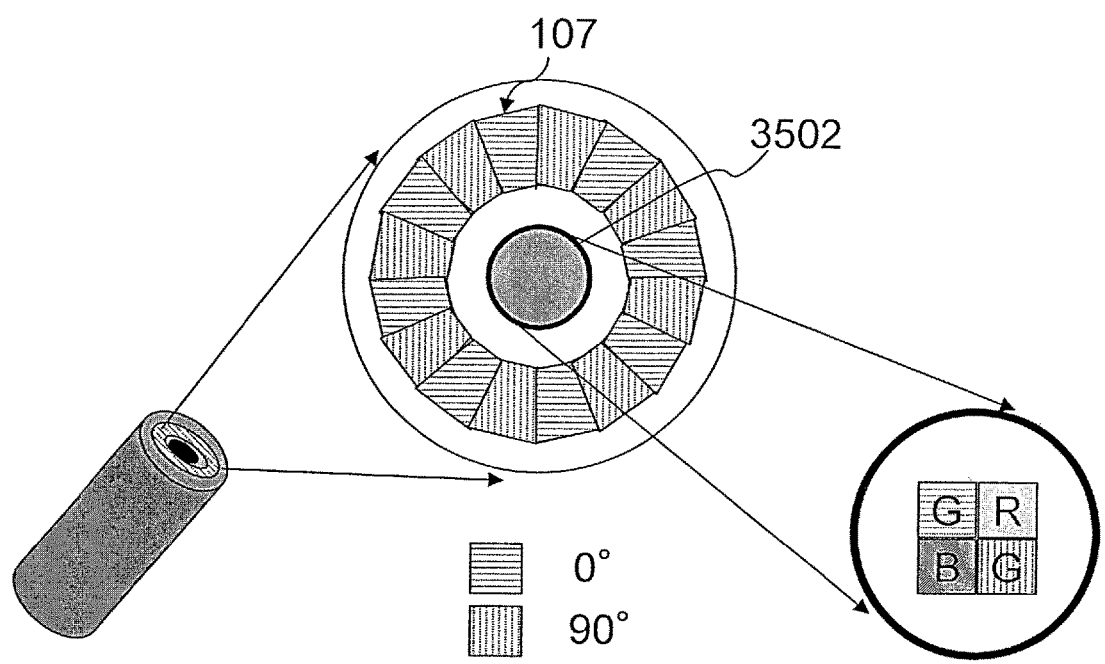
FIG. 36 illustrates the tip portion of an endoscope according to the third embodiment of the present disclosure.

FIG. 36 is an enlarged front view of the tip of an endoscope according to this embodiment. A number of (e.g., sixteen in this example) emission ports, through which an illuminating light beam, of which the polarization plane defines 0 degrees (i.e., P-polarized), and an illuminating light beam, of which the polarization plane defines 90 degrees (i.e., S-polarized), are emitted alternately, are arranged at the tip of the endoscope. In this example, by capturing images with one of the two sets of LEDs, each consisting of non-adjacent eight LEDs of the same type, lit selectively and alternately, a polarized illuminating source which emits P- and S-polarized light beams alternately is realized. As shown in FIG. 36, on the objective lens 3502 as the aperture, arranged is a composite filter region consisting of four (=2×2) color and polarization filters. This is a combination of the R and B non-polarization color filter regions and two kinds of G (0 degrees (P) and 90 degrees (S)) regions which are arranged to intersect with each other at right angles.

Figure 37:
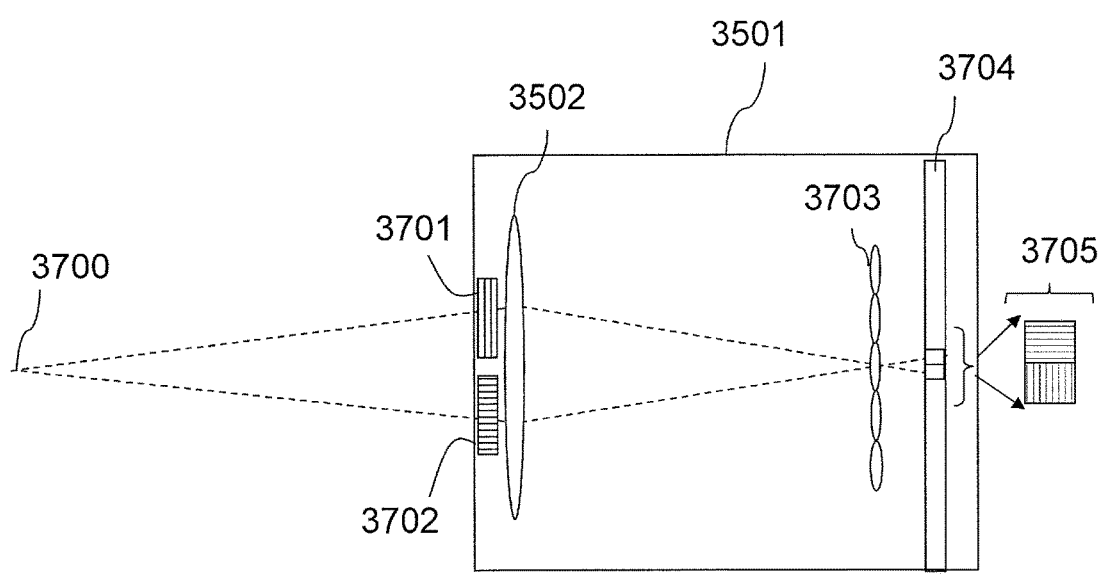
FIG. 37 illustrates a configuration for a micro lens array type color polarization image capturing section according to the third embodiment of the present disclosure.

FIG. 37 illustrates an exemplary configuration for this micro lens array type color polarization image capturing section 3501. In FIG. 37, only two of the four regions on the objective lens 3502, i.e., the two G filter regions shown in FIG. 36 that are the region 3701 where a G filter and a 0 degree (P) polarization filter are arranged and the region 3702 where a G filter and a 90 degree (S) polarization filter are arranged, are shown for convenience sake.

As shown in FIG. 37, the light that has diverged from a point 3700 on the object is transmitted through the two regions 3701 and 3702 on the objective lens 3502, passes through an array of optical elements 3703, and reaches the image capturing plane 3704 of a monochrome image sensor. In this case, the images that have been transmitted through the two regions on the objective lens reach two different pixels 3705. That is why the image produced on the image capturing plane 3704 generally looks an object image but is specifically comprised of two images that have come from two different regions. If digital image processing is carried out by selecting pixels from those images and integrating them together, images that have been transmitted through two regions can be generated separately and a color image can be obtained while using a monochrome image sensor at the same time.

Figure 38:
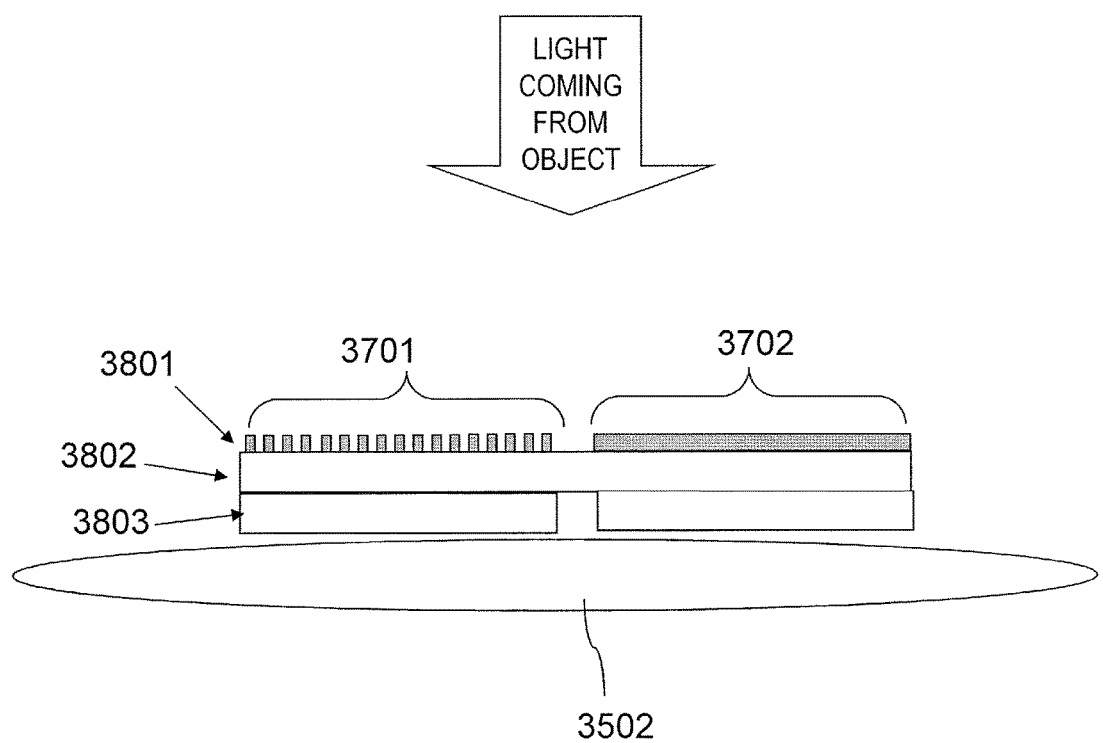
FIG. 38 illustrates a configuration for a color polarization filter area inside an aperture according to the third embodiment of the present disclosure.

FIG. 38 illustrates a cross-sectional structure of the color polarization filter regions 3701 and 3702 inside the aperture. In this example, a metallic wire grid layer 3801 is used as the polarization filters. The wire grid layer 3801 may be obtained by arranging metallic wires at a pitch of about 100 nm, for example, on a transparent substrate 3802. Under the wire grid layer 3801, arranged are color filters 3803. An objective lens 3502 is arranged on the stage next to those color filters 3803. In this case, the order of stacking of the color filters, the wire grid layer and the objective lens and the gap left with respect to the lens may be determined arbitrarily. Also, as the polarizers, not just the wire grids but also polymer-based polarizers, polarizers which use a photonic crystal, polarizers which use form birefringence, or any other existent polarizers may be used as well.

Figure 39:
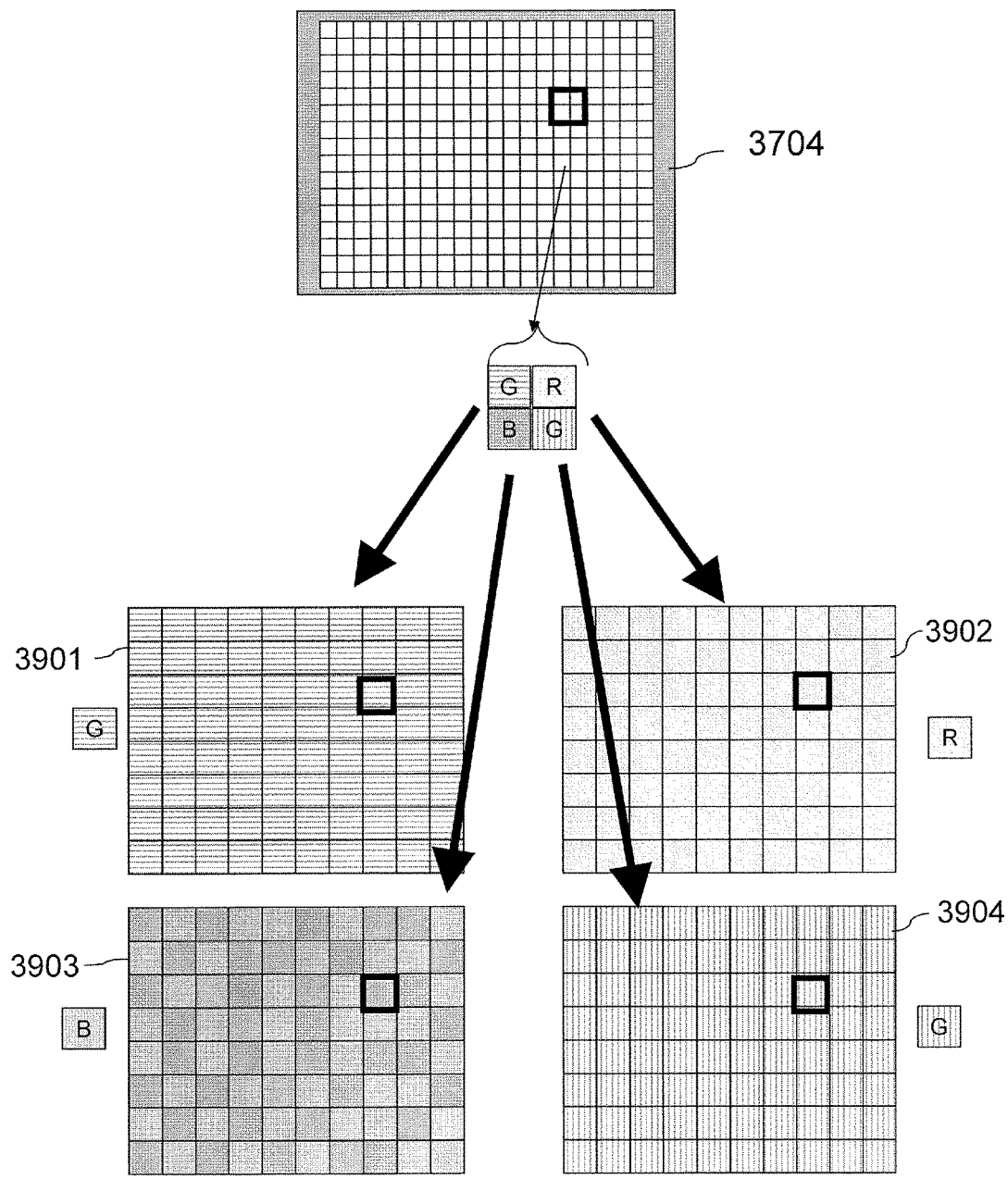
FIG. 39 illustrates how a pixel selecting and re-integrating section 210 operates according to the third embodiment of the present disclosure.

FIG. 39 illustrates how the pixel selecting and re-integrating section 210 performs the processing of generating a color polarization image based on the image that has been captured using this micro lens array type color polarization image sensor. By selecting upper left, upper right, lower left and lower right pixels from the entire image on the image sensor 3704 on a 2×2 pixel unit basis and integrating those pixels together again, the resolution decreases to a quarter (=½×½) but a G P (0 degree)-polarized image 3901, an R non-polarized image 3902, a B non-polarized image 3903 and a G S (90 degree)-polarized image 3904 can be separated. Based on these images, RGB non-polarization color images and a P/S polarization image falling within the G wavelength range can be obtained.

Figure 40:
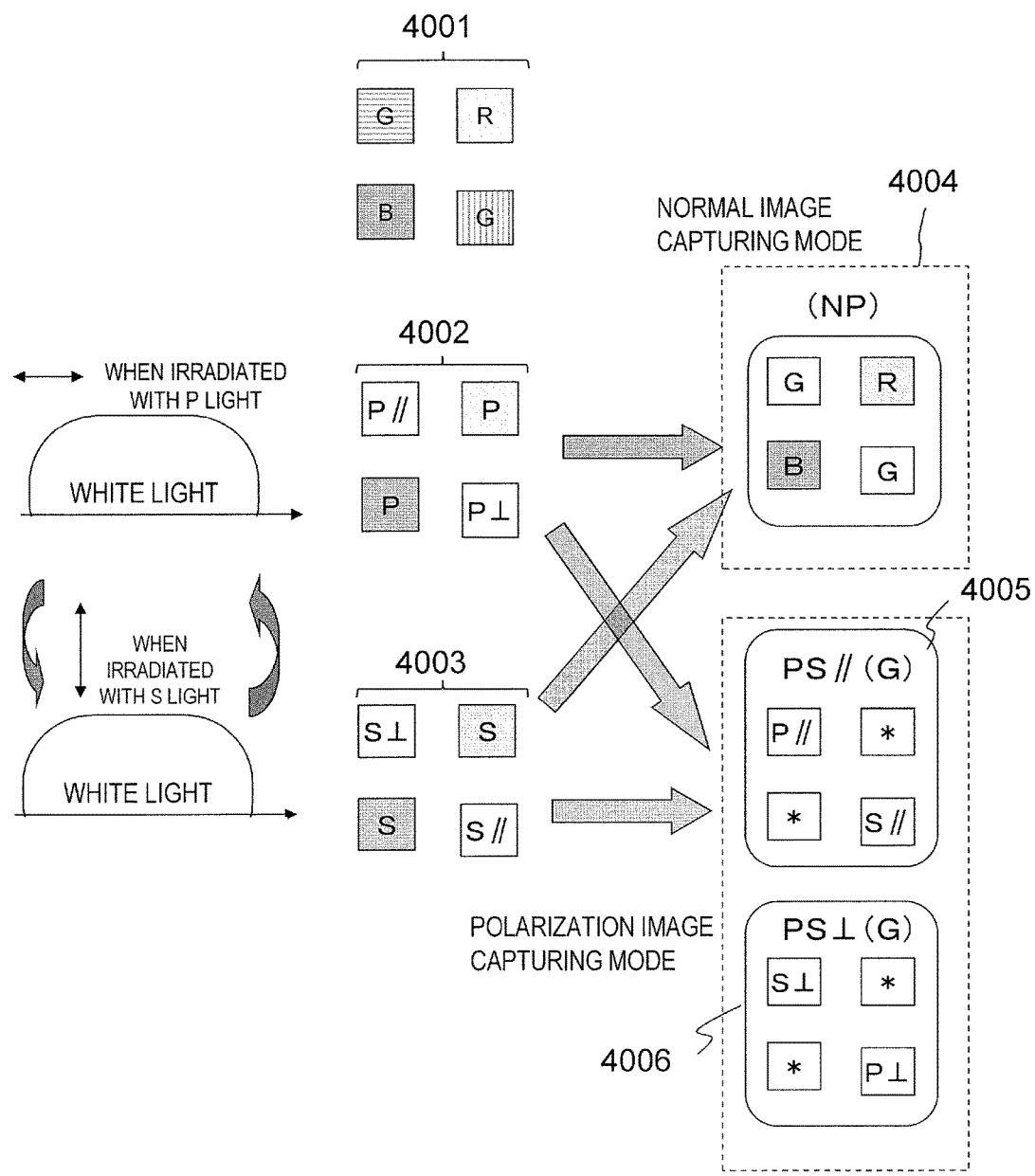
FIG. 40 illustrates what images are obtained in the normal image capturing mode and polarization image capturing mode according to the third embodiment of the present disclosure.

FIG. 40 illustrates images to be obtained by the endoscope of this embodiment in the normal image capturing mode and in the polarization image capturing mode. In both of the normal image capturing mode and the polarization image capturing mode, the object is alternately irradiated with a white P-polarized illuminating light beam and a white S-polarized illuminating light beam, an image is obtained every time the object is irradiated with such a polarized light beam, and the processing shown in FIG. 39 is carried out to obtain four kinds of color polarization images separately each time the same scene is shot. These four kinds of color polarization images thus obtained separately are displayed as indicated by the reference numeral 4001. According to this display method, respective pixels are not represented unlike the conventional technique but four entire images are represented. When the object is irradiated with a P-polarized light beam, the polarization image 4002 is obtained. On the other hand, when the object is irradiated with an S-polarized light beam, the polarization image 4003 is obtained. In FIG. 40, P//, P⊥, S// and S⊥ have the same meanings as what has already been described but P or S indicates an image which has been captured as a non-polarization image under either a P-polarized illuminating light beam or an S-polarized illuminating light beam without using any special polarization filter. In the normal image capturing mode, these images 4002 and 4003 are added together and their average is calculated on a pixel-by-pixel basis. In this adding and averaging processing, the pixels in the parallel Nicols state and the pixels in the crossed Nicols state would be mixed together uniformly as represented by Equations (7). And this result becomes approximately a non-polarization image.

$$(NP)=(P\perp+S//)/2$$

$$(NP)=(P//+S\perp)/2$$

$$(NP)=P+S \qquad (7)$$

As a result V of this adding and averaging processing, a non-polarization color mosaic image 4004 is obtained. The processing of generating a full-color image based on this non-polarization color mosaic image may be carried out by normal color mosaic interpolation.

In the polarization image capturing mode, the images 4002 and 4003 are also obtained alternately. However, by collecting parallel Nicols and crossed Nicols images using only G images, two kinds of polarization images that are PS// 4005 and PS⊥ 4006 can be generated in the G wavelength range. As a result, the output image will be a monochrome image as in the first embodiment shown in FIG. 13.

By adopting a micro lens array type polarization image sensor as is done in this embodiment, polarizers can be arranged inside the aperture of a lens, and therefore, the size of each polarization mosaic element can be increased compared to a situation where the polarizers are arranged over the image sensor, which is one of the advantages achieved by this embodiment. For example, in the polarization mosaic type image sensor adopted in the first and second embodiments described above, the length of the metallic wires that form each polarization mosaic unit is 2 to 3 μm, which is equal to the size of each pixel of the image sensor. If such fine-line metallic wires are used, those metallic wires that form the wire grids can be certainly arranged at a very small pitch but the length of the wire grids and the number of the wires arranged iteratively will be limited. As a result, it is said that the extinction ratio will decrease to about 10 to 1. On the other hand, according to this embodiment, a wire grid polarizer, of which the lens aperture has a relatively large size of approximately 0.5 mm=500 μm, can be used, and therefore, a high extinction ratio of approximately 100 to 1 can be achieved, which contributes greatly to observing a micro-geometric surface texture clearly through an endoscope.

(Embodiment 4)

Figure 41:
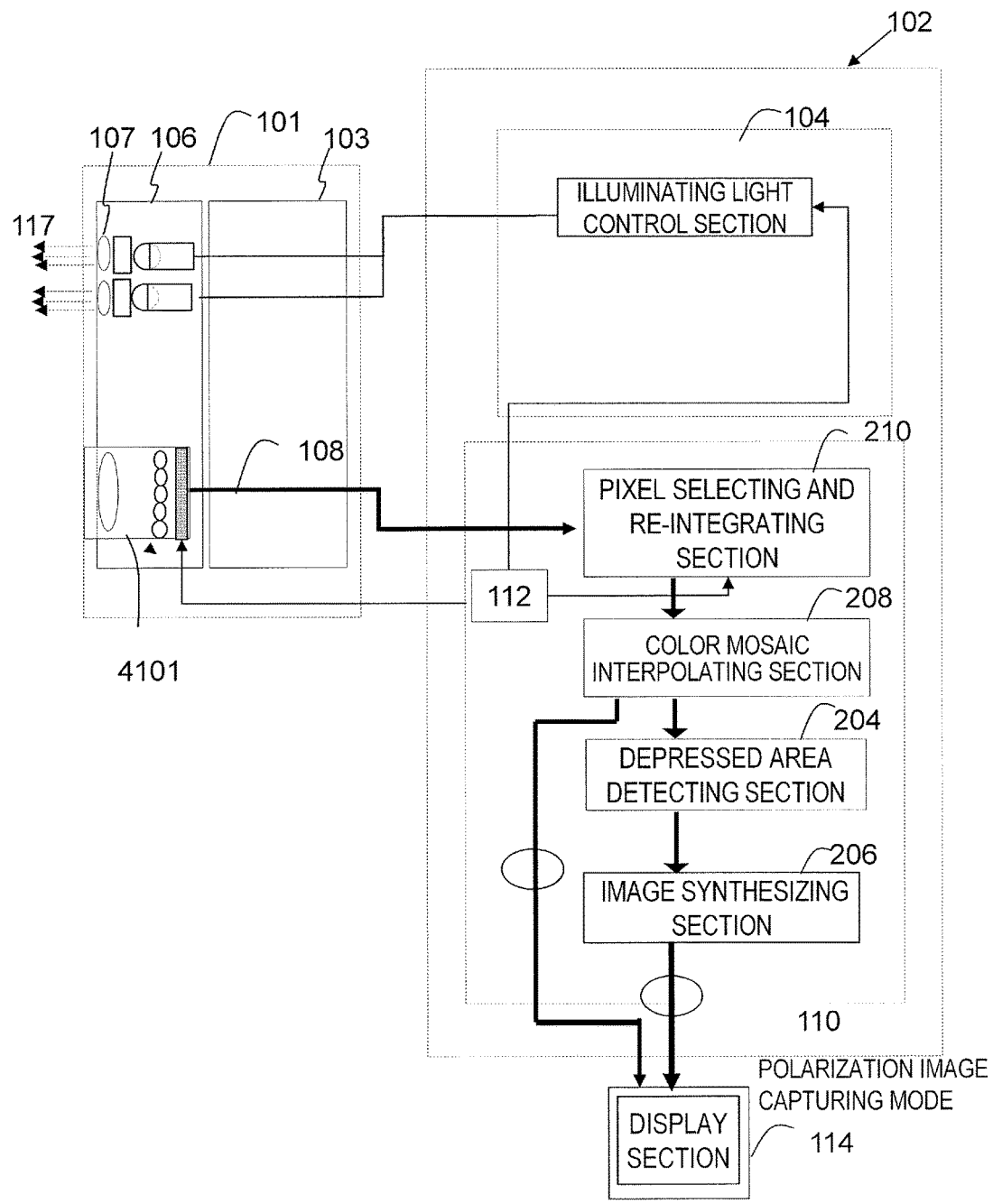
FIG. 41 illustrates a configuration for a fourth embodiment of the present disclosure.

FIG. 41 illustrates a fourth embodiment of the present invention. In this embodiment, a color image is also captured by a single-panel color image sensor with the object irradiated with white light, as in the second embodiment described above. However, unlike the second embodiment, a micro lens array type color polarization image capturing section 4101 is used in this embodiment. The micro lens array type color polarization image capturing section 4101 of this embodiment is different from the counterpart of the third embodiment in the following respects.

Figure 42A:
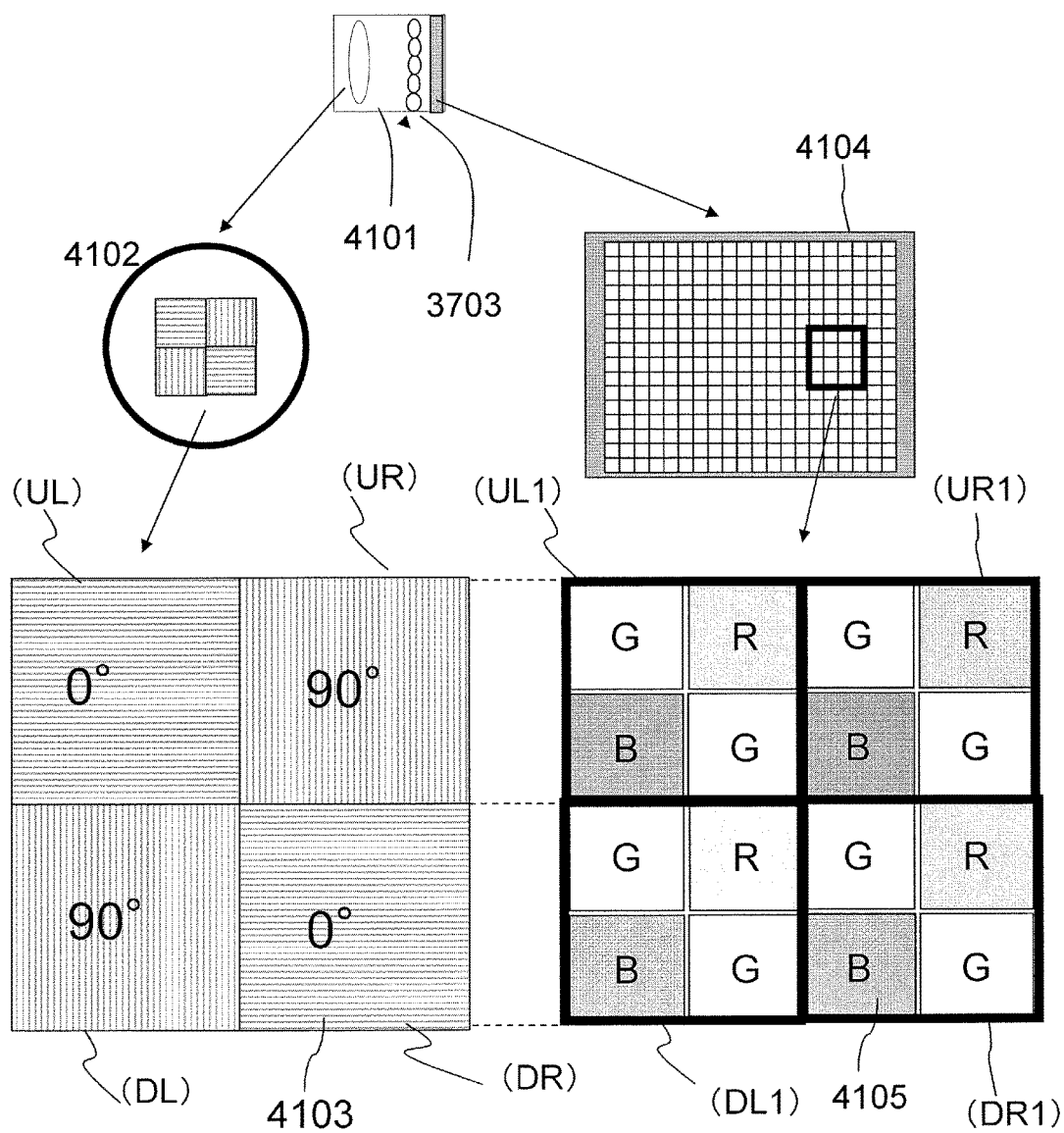
FIG. 42A illustrates a configuration for a micro lens array type color polarization image sensor according to the fourth embodiment of the present disclosure.

FIG. 42A illustrates an exemplary configuration for this micro lens array type color polarization image capturing section 4101. In the aperture of the lens, arranged is only a polarization filter 4103 of a broadband type, which has a 0 degree (P) transmission axis and a 90 degree (S) transmission axis. And the colorization is carried out by a single-panel color image sensor 4104 including a Bayer mosaic 4105. By adopting such a configuration, the polarization image capturing operation and the color image capturing operation are separated from each other. As a result, RGB full-color parallel Nicols and crossed Nicols images can be obtained. As will be described later, the light beams that have been transmitted through the four regions UL, UR, DL and DR of the polarization filter 4103 due to the function of a micro lens array (i.e., an array of optical elements) 3703 are respectively imaged on the four regions UL1, UR1, DL1 and DR1 of the color mosaic filter 4105.

Figure 42B:
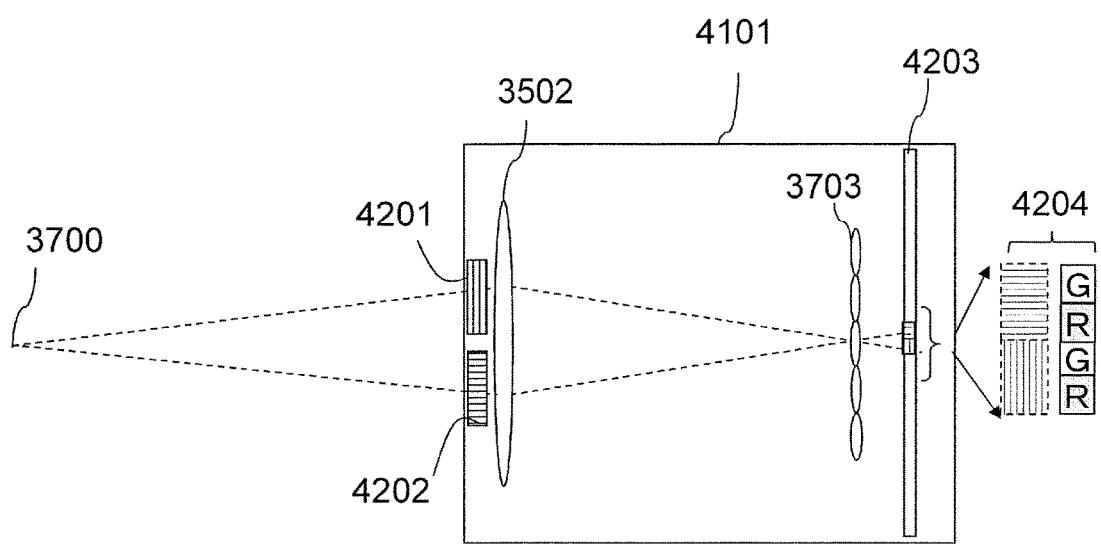
FIG. 42B illustrates a cross-sectional structure of a micro lens array type color polarization image capturing section according to the fourth embodiment of the present disclosure.

FIG. 42B schematically illustrates an exemplary cross-sectional structure for this micro lens array type color polarization image capturing section 4101. In FIG. 42B, shown are only two of the four regions on the objective lens 3502, i.e., the region 4201 where a 90 degree polarization filter is arranged and the region 4202 where a 0 degree polarization filter is arranged as shown in FIG. 41. The light that has diverged from a point 3700 on the object is transmitted through the two regions 4201 and 4202 on the objective lens 3502, passes through the array of optical elements 3703, and reaches the image capturing plane 4203 of the color image sensor where a color mosaic is arranged. In this case, the images produced by the light beams that have been transmitted through the two regions 4201 and 4202 on the objective lens reach two different pixels 4204. That is why the image produced on the image capturing plane 4203 generally looks an object image but is specifically comprised of two images that have come from two different regions where the 0 degree and 90 degree polarization filters are arranged. The images of the respective regions 4201 and 4202 are associated with two pixels of the color mosaic on the color image sensor 4203.

Figure 43:
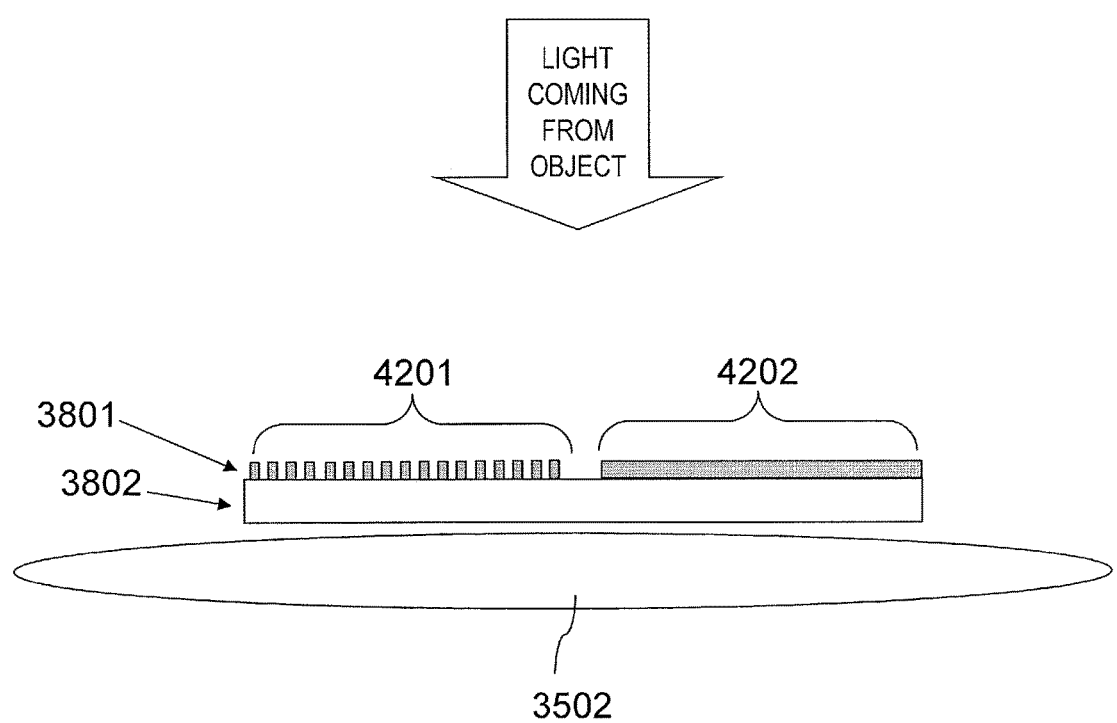
FIG. 43 illustrates a configuration for a polarization filter area inside an aperture according to the fourth embodiment of the present disclosure.

FIG. 43 illustrates a cross-sectional structure of the polarization filter regions 4201 and 4202 inside the aperture according to this embodiment. In this example, a metallic wire grid layer 3801 is used as the polarization filters. The wire grid layer 3801 may be obtained by arranging metallic wires at a pitch of about 100 nm, for example, on a transparent substrate 3802. By using such a wire grid layer 3801, a polarization operation can be carried out in a broad range of the visible light wavelength range.

An objective lens 3502 is arranged on the next stage. In this case, the order of stacking of the wire grid layer 3801 and the objective lens 3502 and the gap left between the wire grid layer 3801 and the objective lens 3502 may be determined arbitrarily. Also, as the polarizers, not just the wire grids but also polymer-based polarizers may be used as well as long as the polarizers can perform a polarization operation in broad range of the visible light wavelength range.

Figure 44:
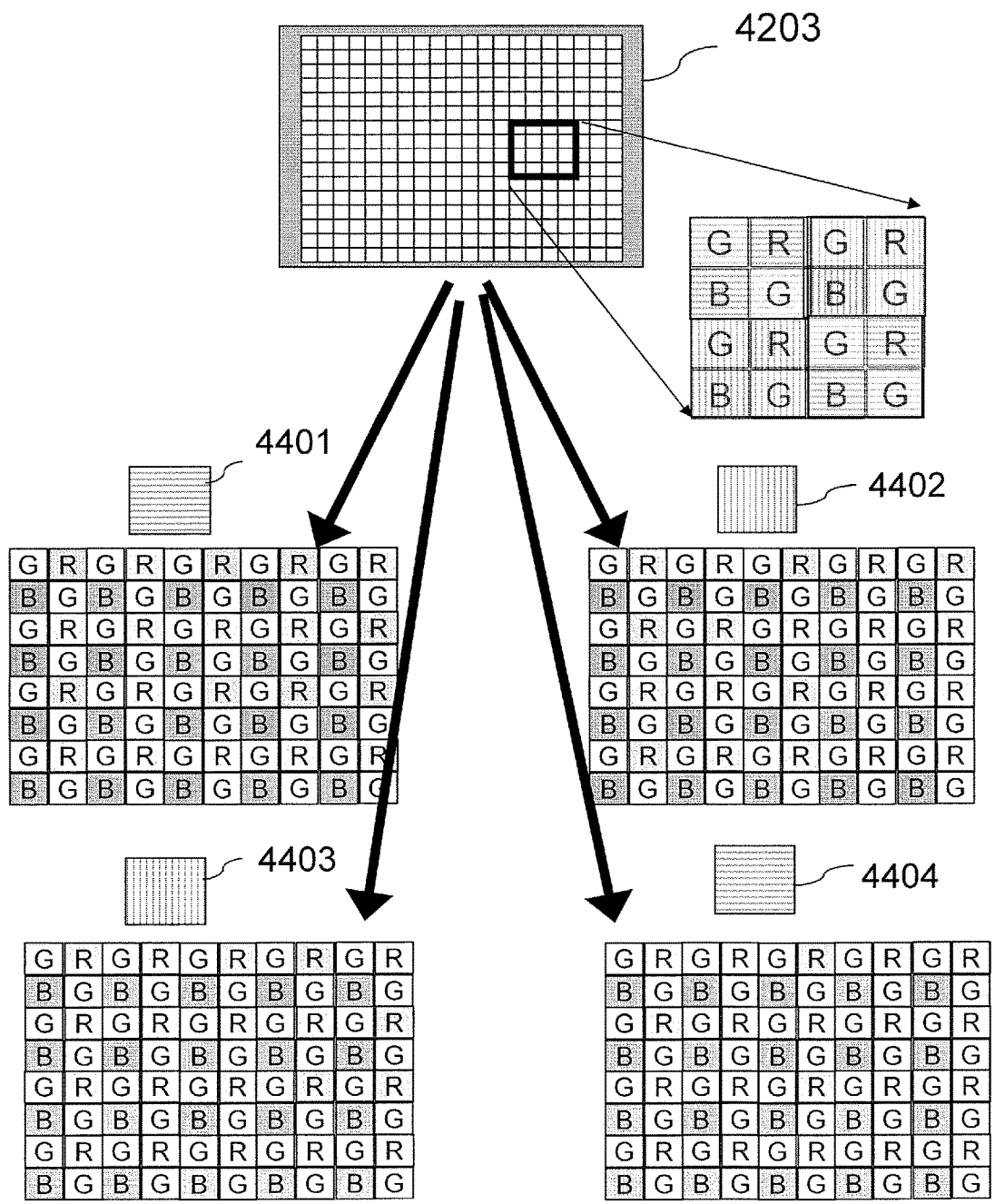
FIG. 44 illustrates how a pixel selecting and re-integrating section 210 operates according to the fourth embodiment of the present disclosure.

FIG. 44 illustrates how the pixel selecting and re-integrating section 210 performs its processing. By selecting upper left, upper right, lower left and lower right pixels from the entire image on the image sensor 4203 on a 2×2 pixel unit basis and integrating those pixels together again, the resolution decreases to a quarter ($=\frac{1}{2}\times\frac{1}{2}$) but a P (0 degree)-polarized color image 4401, an S (90 degree)-polarized color image 4402, another S (90 degree)-polarized color image 4403 and another P (0 degree)-polarized color image 4404 can be separated. After that, the color mosaic interpolation section 208 performs its processing.

Since a 2×2 color Bayer mosaic unit that is RGBG is included within a single polarization filter, the same information as the one obtained in the second modified example of the second embodiment can also be obtained. In addition, by adopting such a micro lens array type polarization image sensor, polarizers can be arranged inside the aperture of the lens, and therefore, wire grid polarization elements of a large size can be used and an extinction ratio as high as approximately 100 to 1 can be achieved.

Embodiments of the present disclosure are broadly applicable to the field of image processing that needs observing, checking, or recognizing the object's surface topography using a medical endoscope camera for digestive organs, a medical camera for dermatologists, dentists, internists or surgeons, an industrial endoscope camera, a fingerprint scanner, or an optical surface analyzer for use in a factory, for example. According to an embodiment of the present disclosure, even the surface topography of a smooth transparent object or semi-transparent object can also be detected accurately, and can be presented in an enhanced form so as to be easily sensible to a human viewer. As a result, the surface topography which is difficult to check just by measuring the light intensity can be checked out very effectively according to an embodiment of the present disclosure.

An image processing apparatus according to the present disclosure is also applicable to digital cameras, camcorders and surveillance cameras, and can be used extensively to increase the contrast ratio when shooting on the surface of water or in the air or when shooting through glass.

While the present invention has been described with respect to exemplary embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. An image processing apparatus selectively operable in either a polarization image capturing mode or a non-polarization image capturing mode based on a signal designating either the polarization image capturing mode or the non-polarization image capturing mode, the apparatus comprising:

an illuminating section which in the polarization image capturing mode sequentially irradiates an object with a first illuminating light beam that is polarized in a first direction and with a second illuminating light beam that is polarized in a second direction that intersects at a right angle with the first direction, and in the non-polarization image capturing mode irradiates the object with a non-polarized illuminating light beam, the illuminating section including an illuminating filter having a transmission characteristic in which a light beam that is polarized in the first direction and a light beam that is polarized in the second direction are transmitted alternately in a series of consecutive wavelength ranges, the illuminating section emitting the first and second illuminating light beams sequentially so that the wavelength range of the first illuminating light beam does not overlap with the wavelength range of the second illuminating light beam somewhere;

an image sensor including a polarization mosaic array in which a plurality of polarizers with mutually different polarization transmission axis directions are arranged and a photosensing element array which receives light that has irradiated the object and has been transmitted through each said polarizer and which outputs a signal;

a polarization mosaic processing section which obtains, in the polarization image capturing mode, a first polarization image to be generated based on a signal representing light that has been transmitted through a polarizer that has the polarization transmission axis in a direction intersecting with the first direction at a right angle while the object is being irradiated with the first illuminating light beam and a second polarization image to be generated based on a signal representing light that has been transmitted through a polarizer that has the polarization transmission axis in a direction intersecting with the second direction at a right angle while the object is being irradiated with the second illuminating light beam, and which obtains, in the non-polarization image capturing mode, a non-polarization image to be generated based on a signal representing light that has been transmitted through each said polarizer while the object is being irradiated with the non-polarized illuminating light beam;

a depressed area detecting section which detects a depressed area on the surface of the object based on at least one of the first and second polarization images by detecting through a differentiation processing a pixel region that is brighter than a surrounding area; and an image forming section which forms an image that represents the depressed area on the object's surface in an enhanced form wherein the polarization mosaic array of the image sensor comprises a first layer and a second layer stacked one upon the other, the first layer and the second layer each including a plurality of polarizers with mutually different polarization transmission axis directions;

wherein each of the plurality of polarizers of each of the first layer and the second layer is a wire grid polarizer having metallic wires which are spaced apart in parallel arrangement.

2. The image processing apparatus of claim 1, wherein the wavelength range of the first illuminating light beam is included in at least one of B (blue) and G (green) wavelength ranges, and the wavelength range of the second illuminating light beam is included in at least one of the B (blue) and G (green) wavelength ranges.

3. The image processing apparatus of claim 1, wherein the wavelength range of the first illuminating light beam is included in a part of a B (blue) wavelength range and in a part of a G (green) wavelength range, and the wavelength range of the second illuminating light beam is included in another part of the B (blue) wavelength range and in another part of the G (green) wavelength range.

4. The image processing apparatus of claim 1, wherein the wavelength range of the first illuminating light beam is included in a part of a B (blue) wavelength range, in a part of a G (green) wavelength range, and in a part of an R (red) wavelength range, and the wavelength range of the second illuminating light beam is included in another part of the B (blue)

wavelength range, in another part of the G (green) wavelength range, and in another part of the R (red) wavelength range.

5. The image processing apparatus of claim 4, wherein the illuminating section emits, as the first illuminating light beam, a light beam included in the part of the B (blue) wavelength range, a light beam included in the part of the G (green) wavelength range, and a light beam included in the part of the R (red) wavelength range at respectively different timings, and also emits, as the second illuminating light beam, a light beam included in that another part of the B (blue) wavelength range, a light beam included in that another part of the G (green) wavelength range, and a light beam included in that another part of the R (red) wavelength range at respectively different timings.

6. The image processing apparatus of claim 5, wherein the illuminating section alternately emits the first and second illuminating light beams and sequentially emits light beams which are included in the R (red), G (green) and B (blue) wavelength ranges.

7. The image processing apparatus of claim 6, wherein the polarization mosaic processing section forms a non-polarization full-color image based on the first and second polarization images to be obtained when the object is illuminated with light beams which are included in the R (red), G (green) and B (blue) wavelength ranges in the polarization image capturing mode.

8. The image processing apparatus of claim 1, further comprising an endoscope including the illuminating section and the image sensor.

9. The image processing apparatus of claim 1, wherein the image formed by the image forming section comprises an image of a brightness of the object's surface.

10. An image processing apparatus selectively operable in either a polarization image capturing mode or a non-polarization image capturing mode based on a signal designating either the polarization image capturing mode or the non-polarization image capturing mode, the apparatus comprising:
an illuminating section which in the polarization image capturing mode sequentially irradiates an object with a first illuminating light beam that is polarized in a first direction and with a second illuminating light beam that is polarized in a second direction that intersects at a right angle with the first direction, and in the non-polarization image capturing mode irradiates the object with a non-polarized illuminating light beam, the illuminating section emitting the first and second illuminating light beams sequentially so that the wavelength range of the first illuminating light beam does not overlap with the wavelength range of the second illuminating light beam somewhere;
an image sensor including a polarization mosaic array in which a plurality of polarizers with mutually different polarization transmission axis directions are arranged and a photosensing element array which receives light that has irradiated the object and has been transmitted through each said polarizer and which outputs a signal, each of the plurality of polarizers being a wire grid polarizer having metallic wires which are spaced apart in parallel arrangement;
a polarization mosaic processing section which obtains, in the polarization image capturing mode, a first polarization image to be generated based on a signal representing light that has been transmitted through a polarizer that has the polarization transmission axis in a direction intersecting with the first direction at a right angle while the object is being irradiated with the first illuminating light beam and a second polarization image to be generated based on a signal representing light that has been transmitted through a polarizer that has the polarization transmission axis in a direction intersecting with the second direction at a right angle while the object is being irradiated with the second illuminating light beam, and which obtains, in the non-polarization image capturing mode, a non-polarization image to be generated based on a signal representing light that has been transmitted through each said polarizer while the object is being irradiated with the non-polarized illuminating light beam;
a depressed area detecting section which detects a depressed area on the surface of the object based on at least one of the first and second polarization images by detecting through a differentiation processing a pixel region that is brighter than a surrounding area; and
an image forming section which forms an image that represents the depressed area on the object's surface in an enhanced form
wherein the polarization mosaic array of the image sensor comprises a first layer and a second layer stacked one upon the other, the first layer and the second layer each including a plurality of polarizers with mutually different polarization transmission axis directions;
wherein each of the plurality of polarizers of each of the first layer and the second layer is a wire grid polarizer having metallic wires which are spaced apart in parallel arrangement.

11. The image processing apparatus of claim 10, wherein the wavelength range of the first illuminating light beam is included in at least one of B (blue) and G (green) wavelength ranges, and
the wavelength range of the second illuminating light beam is included in at least one of the B (blue) and G (green) wavelength ranges.

12. The image processing apparatus of claim 10, wherein the wavelength range of the first illuminating light beam is included in a part of a B (blue) wavelength range and in a part of a G (green) wavelength range, and
the wavelength range of the second illuminating light beam is included in another part of the B (blue) wavelength range and in another part of the G (green) wavelength range.

13. The image processing apparatus of claim 10, wherein the wavelength range of the first illuminating light beam is included in a part of a B (blue) wavelength range, in a part of a G (green) wavelength range, and in a part of an R (red) wavelength range, and
the wavelength range of the second illuminating light beam is included in another part of the B (blue) wavelength range, in another part of the G (green) wavelength range, and in another part of the R (red) wavelength range.

14. The image processing apparatus of claim 13, wherein the illuminating section emits, as the first illuminating light beam, a light beam included in the part of the B (blue) wavelength range, a light beam included in the part of the G (green) wavelength range, and a light beam included in the part of the R (red) wavelength range at respectively different timings, and also emits, as the second illuminating light beam, a light beam included in that another part of the B (blue) wavelength range, a light beam included in that another part of the G (green) wavelength range, and a light beam included in that another part of the R (red) wavelength range at respectively different timings.

15. The image processing apparatus of claim 14, wherein the illuminating section alternately emits the first and second illuminating light beams and sequentially emits light beams which are included in the R (red), G (green) and B (blue) wavelength ranges.

16. The image processing apparatus of claim 15, wherein the polarization mosaic processing section forms a non-polarization full-color image based on the first and second polarization images to be obtained when the object is illuminated with light beams which are included in the R (red), G (green) and B (blue) wavelength ranges in the polarization image capturing mode.

17. The image processing apparatus of claim 10, further comprising an endoscope including the illuminating section and the image sensor.

* * * * *